US007109317B1

(12) United States Patent
Clemons et al.

(10) Patent No.: US 7,109,317 B1
(45) Date of Patent: Sep. 19, 2006

(54) FK506-BASED REGULATION OF BIOLOGICAL EVENTS

(75) Inventors: Paul A. Clemons, Somerville, MA (US); Brian G. Gladstone, Dorchester, MA (US); Abhinav Seth, Tenafly, NJ (US); Stuart L. Schreiber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/435,257

(22) Filed: Nov. 5, 1999

Related U.S. Application Data

(60) Provisional application No. 60/107,473, filed on Nov. 6, 1998.

(51) Int. Cl.
C07H 21/04 (2006.01)
C12N 15/74 (2006.01)
C12N 5/00 (2006.01)

(52) U.S. Cl. ............... 536/23.4; 435/320.1; 435/325

(58) Field of Classification Search ............... 536/23.1, 536/23.4; 438/320.1, 325, 455; 514/44; 800/3, 8, 13, 18
See application file for complete search history.

(56) References Cited

U.S. PATENT DOCUMENTS 5,830,462 A 11/1998 Crabtree et al. ......... 424/93.21
6,165,787 A * 12/2000 Crabtree et al. ......... 435/372.3

FOREIGN PATENT DOCUMENTS

| EP | 0 618 227 | 10/1994 |
|---|---|---|
| WO | WO 94 18317 | 8/1994 |
| WO | WO 96 12806 | 5/1996 |
| WO | WO 96 16172 | 5/1996 |
| WO | WO 96/41865 | 12/1996 |
| WO | WO 97 06246 | 2/1997 |

OTHER PUBLICATIONS

B Chaudhuri et al.,Biochemical and Biophysical Research Communications, "Only in the Presence of Immunophilins can Cyclosporin . . . Autoinhibitory domain yet strengthen interaction between Calcineurin A and B Subunits,"Oct. 1995, vol. 215, No. 2, 781-790.*
D Guerini et al.,Proc.Natl.Acad. Sci USA "Cloning of human calcineurin A: Evidence for two isozymes and identification of a polyproline structural domain,"Dec. 1989, vol. 86, pp. 9183-9187.*
Mondragon A, Overexpression and purification of human calcineurin alpha from *Escherichia coli* and assessment of catalytic functions of residues surrounding the binuclear metal center, 1997, Biochemistry, 36, 4934-42.*
Li R, Materials for immunoisolated cell transplantation, 1998, advanced drug delivery reviews, 33, 87-109.*
Deonarain M, Ligand-targeted receptor-mediated vectors for gene delivery, 1998, Expert Opinion on Therapeutic Patents, 8(1), 53-69.*
Wall RJ, Transgenic livestock: progress and prospects for the future, 1996, Theriogenology, 45, 57-68.*
Houdebine LM, Production of pharmaceutical proteins from transgenic animals, 1994, J. of Biotechnology, 34, 269-87.*
Hammer RE, Genetic engineering of mammalian embryos, 1986, J. of Animal Science, 63, 269-78.*
Mullins LJ, Transgenesis in the rat and larger mammals, 1996, J. Clin Invest., 97(7), 1557-60.*
Verma IM, Gene therapy-promises, problems, and prospects, 1997, Nature, 389, 239-42.*
Miller N, Targeted vectors for gene therapy, 1995, FASEB, 9, 190-99.*
Sigmund CD, Viewpoint: are studies of genetically altered mice out of control?, 2000, Aterioscler Thromb Vasc Biol., 20, 1425-29.*
Cameron ER, Recent advances in transgenic technology, 1997, Mol Biotechnol, vol. 7 (3), 253-65.*
Niemann II, Transgenic farm animals get off the ground, Transgenic Res., 1998, 7(1), 73-5.*
Crystal RG, Transfer of genes to humans: early lessons and obstacles to success, 1995, Science 270, 404-10.*
Anderson FW, Human gene therapy, 1998, Nature, 392, 25-30.*
Kappel C.A. et al. Regulating Gene Expression in Transgenic Animals. Current Opinion Biotech. 1992, vol. 3, pp. 548-553.*
Houdebine LM, The methods to generate transgenic animals and to control transgene expression, 2002, J. of Biotechnology, vol. 98, pp. 145-160.*
Ristevski S, Making better transgenic models, 2005, Molecular Biotechnology, vol. 29, pp. 153-163.*
Smith KR, Gene transfer in higher animals: theoretical considerations and key concepts, J. of Biotechnology, vol. 99, pp. 1-22.*
Montoliu L, Gene transfer strategies in animal transgenesis, 2002, Cloning and Stem Cells, vol. 4, pp. 39-46.*
Griffith et al., (1995). Cell 82:507-522.
Braun et al., (1995) FASEB J., 9:63-72.
Bierer et al., (1993) Current Opinion in Immunology 5:763-773.
Alberg and Schreiber (1993) Science 262:248-250.
Clipstone et al., (1994) J. Biol. Chem 269:26431-26437.
Sigal and Dumont (1992) Ann. Rev. Immunol. 10:519-560.
Pruschy et al., (1994) Chemistry and Biology 1:163-172.
Bram et al., (1993) Mol Cell Biol 13:4760-4769.
Liu et al., (1991) Cell 66:807-815.
Belshaw et al., (1996) Chemistry and Biology 3:731-738.
Kennedy, M.T., et al. "Contributions of Myristoylation to Calcineurin Structure/Function", J. Biol. Chem., vol. 271, No. 43, Oct. 25, 1996, pp. 26517-26521.
Wei, Q. and Lee, E.Y. "Expression and reconstitution of calcineurin A and B subunits", Biochem. Mol. Biol. Int., vol. 41, No. 1, Jan. 1997, pp. 169-177.

* cited by examiner

*Primary Examiner*—Ram R. Shukla
*Assistant Examiner*—David A. Montanari
(74) *Attorney, Agent, or Firm*—Fish & Neave IP Group Ropes & Gray LLP

(57) ABSTRACT

Materials and methods are disclosed for regulation of biological events such as target gene transcription and growth, proliferation or differentiation of engineered cells.

19 Claims, 10 Drawing Sheets

FKBP₃-VE: | NLS | FKBP | FKBP | FKBP | VP16 | Flu |

FULL CAB-VE: | NLS | CNA 12-394 | CNB | VP16 | Flu |

MINI CAB-VE: | NLS | CNA | CNB | VP16 | Flu | CNA 340-394

FKBP₃-GE: | GAL4 | FKBP | FKBP | FKBP | Flag |

FULL CAB-GE: | GAL4 | CNA 12-394 | CNB | Flag |

MINI CAB-VE: | GAL4 | CNA | CNB | Flag | CNA 340-394

FULL CAB-p65: | NLS | CNA 12-394 | CNB | p65 | Flu |

MINI CAB-p65: | NLS | CNA | CNB | p65 | Flu | CNA 340-394

Fig. 1

FK506-BASED REGULATION OF BIOLOGICAL EVENTS

This application claims priority from provisional application 60/107,473 filed Nov. 6, 1998.

This work was supported in part by grant number GM-52067 from the National Institute of General Medical Sciences. Accordingly, the US government has certain rights in this invention.

BACKGROUND OF THE INVENTION

FK506 is a natural product which binds to an FK506-binding protein, FKBP, with high affinity to form an FK506:FKBP complex. Reported Kd values for that interaction are as low as 400 pM. The FK506:FKBP complex binds with high affinity to the protein phosphatase calcineurin to form a tripartite, [FKBP:FK506]:[calcineurin], complex. Calcineurin is a heterodimer of a catalytic subunit (calcineurin A) and a regulatory subunit (calcineurin B.) In this tripartite complex FK506 acts as a dimerizer or adapter to join FKBP to calcineurin.

Numerous naturally occurring FK506 binding proteins (FKBPs) are known. See e.g. Kay, 1996, Biochem. J. 314:361–385 (review). FKBP proteins have been used for their ligand-binding properties in biological switches based on ligand-mediated multimerization of immunophilin-based recombinant proteins as disclosed e.g. in Spencer et al, 1993, Science 262:1019–1024 and in WO 94/18317.

Cyclosporin A is another macrocyclic natural product of interest. It binds to the protein cyclophilin to form a complex which also binds to calcineurin to form an immunosuppressive complex. Cyclosporin thus also acts as a dimerizer. While the potent immunosuppressive activity of FK506 and cyclosporin would limit their utility as a dimerizer, especially in animals, this invention harnesses their dimerizing potential (and that of related compounds) while avoiding their profound, inherent limitations.

SUMMARY OF THE INVENTION

This invention concerns new configurations for biological switches and provides new methods and materials for regulating biological events, particularly in animal cells. Those biological events include, for example, gene transcription, activation of an intracellular signal transduction pathway (leading, for example, to gene expression, cell proliferation or apoptotic cell death), gene knock-out, blockade of expression of a gene, and inhibition of the function of a gene product. The invention relies upon two types of fusion proteins which when complexed through mutual binding to a common ligand, are capable of actuating, directly or indirectly, the desired event.

This invention encompasses recombinant DNA constructs encoding those fusion proteins; DNA vectors containing one or more of those constructs; the fusion proteins encoded by the foregoing constructs; cells, especially animal cells, transduced with (i.e., containing and capable of expressing) one or more of the DNA constructs described herein; small molecules (bivalent or multivalent multimerizing agents) which bind to and are capable of inducing multimerization of the fusion protein molecules; and methods for preparing and using the foregoing.

More specifically, this invention provides methods and materials for making and using genetically engineered cells which are responsive to the presence of an FKBP/CAB ligand or a cyclophilin/CAB ligand. The invention relies upon the introduction into cells of recombinant DNAs encoding a set of fusion proteins which are capable of forming a complex with each other in the presence of ligand. Contacting such genetically engineered cells with a ligand results in complex formation between the fusion proteins and initiation of a biological response. One of the fusion proteins contains one or more copies of a calcineurin A/calcineurin B domain (CAB) and at least one heterologous protein domain. The second fusion protein contains one or more copies of a domain derived from an FKBP protein which is capable of binding to an FKBP/CAB ligand and forming a complex with a CAB-containing protein. The second fusion protein may alternatively contain one or more copies of a cyclophilin domain which is capable of binding cyclosporin or other cyclophilin/CAB ligand and forming a complex with a CAB-containing protein. The second fusion protein also contains at least one heterologous domain which may be the same or different from a heterologous domain of the first fusion protein. CAB and FKBP domains for use in fusion proteins of this invention may be selected from naturally occurring proteins and may be variously modified, as is discussed in detail below. While CAB, FKBP and heterologous domains derived from various species may be used, human peptide sequences or variants thereof are preferred for human gene therapy applications. Operationally, the CAB and FKBP domains serve as receptor (or "ligand-binding") domains and direct the complex formation between the fusion proteins under the mediation of ligand molecules. The nature of the biological response triggered by ligand-mediated complexes is determined by the heterologous domains of the fusion proteins. The heterologous domains are therefore also referred to as "action" domains.

Various heterologous protein domains may be used in these fusion proteins, including, among others, DNA binding domains, transcription regulatory domains and cellular signaling domains. In one aspect of the invention, the two fusion proteins (one of which contains at least one CAB domain, the other contains at least one FKBP or cyclophilin domain) each contain at least one different heterologous domain, i.e., a heterologous domain not contained in the other fusion protein. For example, in certain embodiments, one of the fusion proteins contains at least one DNA binding domain and the other fusion protein contains at least one transcription activation domain. Ligand-mediated association of the fusion proteins represents the formation of a transcription factor complex and leads to initiation of transcription of a target gene linked to a DNA sequence recognized by (i.e., capable of binding with) a DNA-binding domain on one of the fusion proteins. In other embodiments, one of the fusion proteins contains at least one domain capable of directing the fusion protein to a particular cellular location such as the cell membrane, nucleus, etc. Localization domains which target the cell membrane include domains such as a myristoylation site or a transmembrane region of a receptor protein or other membrane-spanning protein. The other fusion protein contains a signalling domain capable, upon membrane localization and/or clustering, of activating a cellular signal transduction pathway. Examples of signalling domains include an intracellular domain of a growth factor or cytokine receptor, an apoptosis triggering domain such as the intracellular domain of FAS or TNF-R1, and domains derived from other intracellular signalling proteins such as SOS, Raf, lck, ZAP-70, caspases, etc. A number of illustrative signalling proteins are disclosed in WO 94/18317 (see e.g. pages 23–26). In still other embodiments, each of the fusion proteins contains at least one CAB domain and at least one FKBP domain and/or a cyclophilin domain, as well as one or more heterologous domains. Such fusion proteins are capable of homodimerization in the presence of ligand. In general, domains containing peptide sequence endogenous to the host cell are preferred. Thus, for human gene therapy applications, domains of human origin are of particular interest.

Recombinant DNA molecules encoding the fusion proteins are also provided, as are vectors capable of directing their expression, particularly in eukaryotic cells, of which yeast and animal cells are of particular interest. In view of the constituent components of the fusion proteins, the recombinant DNA molecules which encode them are capable of selectively hybridizing (a) to a DNA molecule encoding a given fusion protein's ligand-binding domain (CAB domain, FKBP domain or cyclophilin domain) or a protein containing such a domain and (b) to a DNA molecule encoding the heterologous domain or a protein from which the heterologous protein domain was derived. DNAs are also encompassed which would be capable of so hybridizing but for the degeneracy of the genetic code.

Using DNA sequences encoding the fusion proteins of this invention and vectors capable of directing their expression in eukaryotic cells, one may genetically engineer cells for a number of important uses. To do so, one first provides an expression vector or DNA construct for directing the expression in a eukaryotic (preferably animal) cell of the desired fusion protein and then introduces the recombinant DNA into the cells in a manner permitting DNA uptake and expression of the introduced DNA in at least a portion of the cells. One may use any of the various methods and materials for introducing DNA into cells for heterologous gene expression, a variety of which are well known and/or commercially available.

One object of this invention is thus to provide an animal cell containing recombinant DNAs encoding two fusion proteins as described herein. One of the fusion proteins is capable of binding to ligand and contains at least one FKBP or cyclophilin domain and at least one domain that is heterologous thereto. The second fusion protein contains at least one CAB domain and at least one domain heterologous thereto and is capable of forming a tripartite complex with the first fusion protein and one or more molecules of ligand. In some embodiments one or more of the heterologous domains present on one of the fusion proteins are also present on the other fusion protein, i.e., the two fusion proteins have one or more common heterologous domains. In other embodiments, each fusion protein contains one or more different heterologous domains.

A specific object of this invention is to provide animal cells engineered such that contacting the cells with ligand leads to transcription of a target gene. Such cells contain, in addition to recombinant DNAs encoding the two fusion proteins, a target gene construct which comprises a target gene operably linked to a DNA sequence which is responsive to the presence of a complex of the fusion proteins with the ligand. In certain embodiments the cells are responsive to contact with a ligand which binds to the FKBP fusion protein and CAB fusion protein with a detectable preference over binding to endogenous FKBP or CAB-containing proteins of the host cell. Similarly, ligands which bind cyclophilin-containing fusion proteins with greater affinity than their binding to endogenous cyclophilin may be desirable.

Another specific object of this invention is to provide animal cells engineered such that contacting the cells with the ligand stimulates cell growth, differentiation or proliferation. In such cells, at least one of the heterologous domains on at least one of the fusion proteins is a domain such as the intracellular domain of a receptor for a hormone which mediates cell growth, differentiation or proliferation. Cell growth, differentiation and/or proliferation follow clustering of the receptor intracellular signalling domains. Such clustering occurs in nature following hormone binding, and in engineered cells of this invention following contact with ligand.

Cells of human origin are preferred for human gene therapy applications, although cell types of various origins (human or other species) may be used, and may, if desired, be encapsulated within a biocompatible material for use in human subjects.

Another object of the invention is to provide materials and methods for producing the foregoing engineered cells. This object is met by providing recombinant DNAs encoding the fusion proteins, together with any ancillary recombinant DNAs such as a target gene construct, and introducing the recombinant DNAs into the host cells under conditions permitting DNA uptake by cells. Such transduction may be effected ex vivo, using host cells maintained in culture. Cells that are engineered in culture may subsequently be introduced into a host organism, e.g. in ex vivo gene therapy applications. Doing so thus constitutes a method for providing a host organism, preferably a human or non-human mammal, which is responsive (as described herein) to the presence of ligand. Alternatively transduction may be effected in vivo, using host cells present in a human or non-human host organism. In such cases, the DNA molecules are introduced directly into the host organism under conditions permitting uptake of the DNA by one or more of the host organism's cells. This approach thus constitutes an alternative method for providing a host organism, preferably a human or non-human mammal, which is responsive (as described herein) to the presence of ligand. Various materials and methods for the introduction of DNA into cells in culture or in whole organisms are known in the art and may be adapted for use in practicing this invention.

Other objects are achieved using the engineered cells described herein. For instance, a method is provided for multimerizing the fusion proteins of this invention by contacting cells engineered as described herein with an effective amount of ligand, permitting the ligand to form a complex with the fusion proteins. In embodiments in which multimerization of the fusion proteins triggers transcription of a target gene, this constitutes a method for activating the expression of the target gene. In embodiments in which the fusion proteins contain one or more signalling domains, this constitutes a method for activating a cellular signal transduction pathway. These methods may be carried out in cell culture or in whole organisms, including human patients. In the former case, the ligand is added to the culture medium. In the latter case, the ligand (which may be in the form of a pharmaceutical or veterinary composition) is administered to the whole organism, e.g., orally, parenterally, etc. Preferably, the dose or ligand administered to an animal is below the dosage level that would cause undue immunosuppression in the recipient.

A further object of this invention is to provide kits for use in the genetic engineering of cells or human or non-human animals as described herein. One such kit contains recombinant DNA constructs encoding a pair of fusion proteins of this invention. The recombinant DNA constructs will generally be in the form of eukaryotic expression vectors suitable for introduction into animal cells and capable of directing the expression of the fusion proteins therein. The kit may also contain a sample of ligand capable of forming a complex with the encoded fusion proteins. The kit may further contain a multimerization antagonist such as rapamycin or some other compound capable of binding to one of the fusion proteins but incapable of forming a complex with both. In certain embodiments, the recombinant DNA constructs encoding the fusion proteins will contain a cloning site in place of DNA encoding one or more of the heterologous domains, thus permitting the practitioner to introduce DNA encoding a heterologous domain of choice. In some embodiments the kit may also contain a target gene construct containing a target gene or cloning site linked to a DNA sequence responsive to the presence of the complexed fusion proteins, as described in more detail elsewhere.

BRIEF DESCRIPTION OF THE FIGURES

FIG. 1: Constructs used in the CAB dimerization system.

DETAILED DESCRIPTION OF THE INVENTION

Definitions

Figure 2:
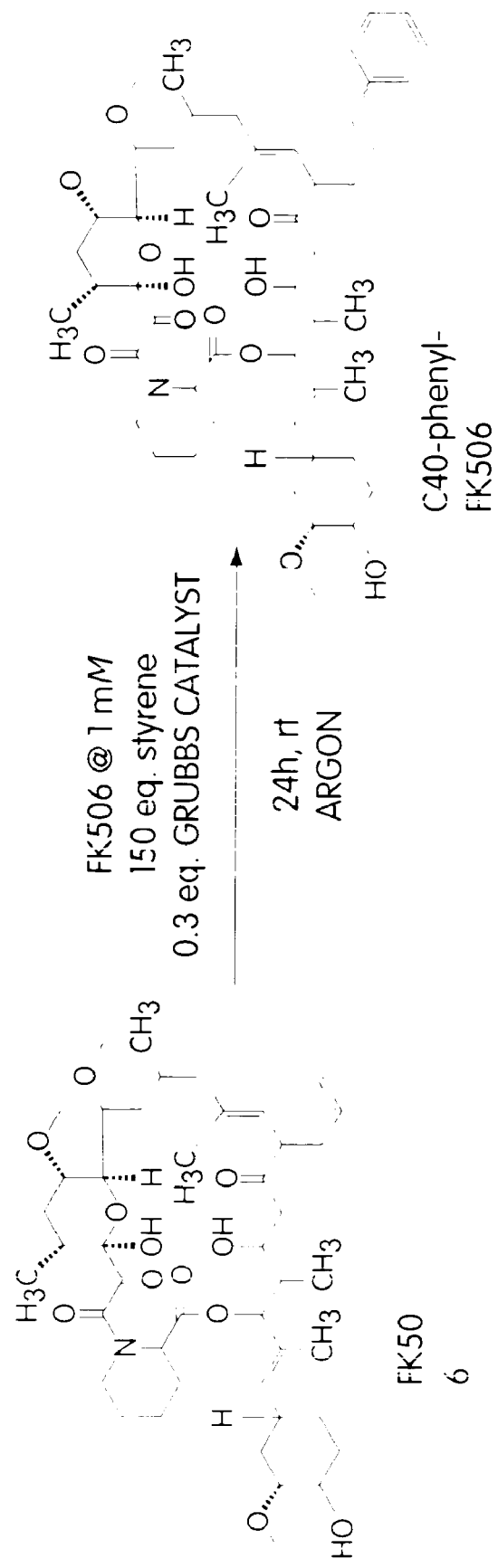
FIG. 2: Reaction scheme for synthesis of E/Z C40-phenyl-FK506.

The definitions of terms as they are used herein will be helpful for a full understanding of the present disclosure.

"Activate" as applied to the expression or transcription of a gene denotes a directly or indirectly observable increase in the production of a gene product, e.g., an RNA or polypeptide encoded by the gene.

"Capable of selectively hybridizing" as that phrase is used herein means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

"Cells", "host cells" or "recombinant host cells" refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

A "cloning site", also sometimes referred to as a "multiple cloning site" or a "polylinker" is a region within a vector which contains multiple sites for restriction enzyme cleavage, thus rendering the vector suitable for cloning of exogenous genes.

A "coding sequence" or a sequence which "encodes" a particular polypeptide or RNA, is a nucleic acid sequence which is transcribed (in the case of DNA) and translated (in the case of mRNA) into a polypeptide in vitro or in vivo when placed under the control of an appropriate expression control sequence. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

"Composite", "fusion", and "recombinant" denote a material such as a nucleic acid, nucleic acid sequence or polypeptide which contains at least two constituent portions which are mutually heterologous in the sense that they are not otherwise found directly (covalently) linked in nature, e.g. are not found in the same continuous polypeptide or gene in nature, at least not in the same order or orientation or with the same spacing present in the composite, fusion or recombinant product. Such materials contain components derived from at least two different proteins or genes or from at least two non-adjacent portions of the same protein or gene. In general, "composite" refers to portions of different proteins or nucleic acids which are joined together to form a single functional unit, while "fusion" generally refers to two or more functional units which are linked together. "Recombinant" is generally used in the context of nucleic acids or nucleic acid sequences.

The term "conjoint", with respect to administration of two or more viruses, refers to the simultaneous, sequential or separate dosing of the individual virus provided that some overlap occurs in the simultaneous presence of the viruses in one or more cells of the animal.

A "construct", e.g., a "nucleic acid construct" or "DNA construct" refers to a nucleic acid or nucleic acid sequence.

"Derived from" denotes a peptide or nucleotide sequence selected from within a given sequence. A peptide or nucleotide sequence derived from a named sequence may further contain a small number of modifications relative to the parent sequence, in most cases representing deletion, replacement or insertion of less than about 15%, preferably less than about 10%, and in many cases less than about 5%, of amino acid residues or bases present in the parent sequence. In the case of DNAs, one DNA molecule is also considered to be derived from another if the two are capable of selectively hybridizing to one another. Polypeptides or polypeptide sequences are also considered to be derived from a reference polypeptide or polypeptide sequence if any DNAs encoding the two polypeptides or sequences are capable of selectively hybridizing to one another. Typically, a derived peptide sequence will differ from a parent sequence by the replacement of up to 5 amino acids, in many cases up to 3 amino acids, and very often by 0 or 1 amino acids. A derived nucleic acid sequence will differ from a parent sequence by the replacement of up to 15 bases, in many cases up to 9 bases, and very often by 0–3 bases. In some cases the amino acid(s) or base(s) is/are added or deleted rather than replaced.

"Dimerization", "oligomerization" and "multimerization" are used interchangeably herein and refer to the association or clustering of two or more protein molecules, mediated by the binding of a drug to at least one of the proteins. In preferred embodiments, the multimerization is mediated by the binding of two or more such protein molecules to a common divalent or multivalent drug. The formation of a complex comprising two or more protein molecules, each of which containing one or more FKBP domains, together with one or more molecules of an FKBP ligand which is at least divalent (e.g. FK1012 or AP1510) is an example of such association or clustering. In cases where at least one of the proteins contains more than one drug binding domain, e.g., where at least one of the proteins contains three FKBP domains, the presence of a divalent drug leads to the clustering of more than two protein molecules. Embodiments in which the drug is more than divalent (e.g. trivalent) in its ability to bind to proteins bearing drug binding domains also can result in clustering of more than two protein molecules. The formation of a tripartite complex comprising a protein containing at least one CAB domain, a protein containing at least one FKBP domain and a ligand molecule is another example of such protein clustering. In certain embodiments of this invention, fusion proteins contain multiple CAB and/or FKBP domains. Complexes of such proteins may contain more than one molecule of ligand or other dimerizing agent and more than one copy of one or more of the constituent proteins. Again, such multimeric complexes are still referred to herein as tripartite complexes to indicate the presence of the three types of constituent molecules, even if one or more are represented by multiple copies. The formation of complexes containing at least one divalent drug and at least two protein molecules, each of which contains at least one drug binding domain, may be referred to as "oligomerization" or "multimerization", or simply as "dimerization", "clustering" or association".

"Dimerizer" denotes a compound which brings together two or more proteins in a multimeric complex.

"Divalent", as that term is applied to ligands in this document, denotes a ligand which is capable of complexing with at least two protein molecules which contain ligand binding domains, to form a three (or greater number)-component complex.

"Domain" refers to a portion of a protein or polypeptide. In the art, the term "domain" may refer to a portion of a protein having a discrete secondary structure. However, as will be apparent from the context used herein, the term "domain" as used in this document does not necessariy connote a given secondary structure. Rather, a peptide sequence is referred to herein as a "domain" simply to denote a polypeptide sequence from a defined source, or having or conferring an intended or observed activity. Domains can be derived from naturally occurring proteins or may comprise non-naturally-occurring sequence.

"DNA recognition sequence" means a DNA sequence which is capable of binding to one or more DNA-binding domains, e.g., of a transcription factor or an engineered polypeptide.

"Endogenous" refers to molecules which are naturally occurring in a cell, i.e. prior to the genetic engineering or infection of the cell.

"Exogenous" refers to molecules which are not naturally present in the cell, and which have been, e.g., introduced by transfection or transduction of the cell (or the parent cell thereof).

FKBPs (FK506 binding proteins) are the cytosolic receptors for macrolides such as FK506, FK520 and rapamycin and are highly conserved across species lines. For the purpose of this disclosure, FKBPs are proteins or protein domains which are capable of binding to an FKBP/CAB ligand and further forming a tripartite complex with calcineurin or a CAB-containing protein. An FKBP domain may also be referred to as a "FK506 binding domain". Information concerning the nucleotide sequences, cloning, and other aspects of various FKBP species is already known in the art, permitting the synthesis or cloning of DNA encoding the desired FKBP peptide sequence, e.g., using well known methods and PCR primers based on published sequences. See e.g. Staendart et al, 1990, Nature 346, 671–674 (human FKBP12); Kay, 1996, Biochem. J. 314, 361–385 (review). Homologous FKBP proteins in other mammalian species, in yeast, and in other organsims are also known in the art and may be used in the fusion proteins disclosed herein. See e.g. Kay, 1996, Biochem. J. 314, 361–385 (review). The size of FKBP domains for use in this invention are usually 90–100 amino acids, although this varies, depending on which FKBP protein is employed. An FKBP domain of a fusion protein of this invention will be capable of binding to an FKBP/CAB ligand and participating in a tripartite complex with calcineurin or a CAB-containing protein (as may be determined by any means, direct or indirect, for detecting such binding). The peptide sequence of an FKBP domain of an FKBP fusion protein of this invention comprises (a) a naturally occurring FKBP peptide sequence, preferably derived from the human FKBP12 protein (exemplified below) or a peptide sequence derived from another human FKBP, from a murine or other mammalian FKBP, or from some other animal, yeast or fungal FKBP; (b) a variant of a naturally occurring FKBP sequence in which up to about ten (preferably 1–5, more preferably 1–3, and in some embodiments just one) amino acids of the naturally-occurring peptide sequence have been deleted, inserted, or replaced with substitute amino acids; or (c) a peptide sequence encoded by a DNA sequence capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

An "FKBP/CAB ligand" is a compound, e.g. FK506 or an analog, homolog, derivative or mimetic of any of the foregoing, which binds to an FKBP protein to form a complex which binds to calcineurin or a CAB protein. Similarly, a "cyclophilin/CAB ligand" is a compound, e.g. cyclosporin or an analog, homolog, derivative or mimetic of any of the foregoing, which binds to a cyclophilin protein to form a complex which binds to calcineurin or a CAB protein.

"Gene" refers to a nucleic acid molecule or sequence comprising an open reading frame and including at least one exon and (optionally) an intron sequence. The term "intron" refers to a DNA sequence present in a given gene which is not translated into protein and is generally found between exons.

"Genetically engineered cells" denotes cells which have been modified by the introduction of recombinant or heterologous nucleic acids (e.g. one or more DNA constructs or their RNA counterparts) and further includes the progeny of such cells which retain part or all of such genetic modification.

"Heterologous" as it relates to nucleic acid sequences such as coding sequences and control sequences, denotes sequences that are not normally joined together, and/or are not normally associated with a particular cell. Thus, a "heterologous" region of a nucleic acid construct is a segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, in the case of a cell transduced with a nucleic acid construct which is not normally present in the cell, the cell and the construct would be considered mutually heterologous for purposes of this invention. Allelic variation or naturally occurring mutational events do not give rise to heterologous DNA, as used herein.

"Interact" as used herein is meant to include detectable interactions between molecules, such as can be detected using, for example, a yeast or mammalian two hybrid assay or by immunoprecipitation. The term interact is also meant to include "binding" interactions between molecules. Interactions may be, for example, protein—protein, protein-nucleic acid, protein-small molecule or small molecule-nucleic acid in nature.

"Ligand" refers to any molecule which is capable of interacting with a corresponding protein or protein domain. A ligand can be naturally occurring, or the ligand can be partially or wholly synthetic. The term "modified ligand" refers to a ligand which has been modified such that it does not significantly interact with the naturally occurring receptor of the ligand in its non modified form. As used herein, ligand refers to an FKBP/CAB ligand.

"Minimal promoter" refers to the minimal expression control sequence that is necessary for initiating transcription of a selected DNA sequence to which it is operably linked.

The terms "promoter" and "expression control sequence" further encompass "tissue specific" promoters and expression control sequences, i.e., promoters and expression control sequences which effect expression of the selected DNA sequence preferentially in specific cells (e.g., cells of a specific tissue). Gene expression occurs preferentially in a specific cell if expression in this cell type is significantly higher than expression in other cell types. The terms "promoter" and "expression control sequence" also encompass so-called "leaky" promoters and "expression control sequences", which regulate expression of a selected DNA primarily in one tissue, but cause expression in other tissues as well. These terms also encompass non-tissue specific promoters and expression control sequences which are active in most cell types. Furthermore, a promoter or expression control sequence can be constitutive i.e. one which is active basally or inducible, i.e., a promoter or expression control sequence which is active primarily in response to a stimulus. A stimulus can be, e.g., a molecule, such as a hormone, a cytokine, a heavy metal, phorbol esters, cyclic AMP (cAMP), or retinoic acid.

"Nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. For simplicity, the term DNA is often used herein to refer to any nucleic acid.

A "nucleic acid binding domain" refers to a polypeptide which interacts, or binds, with a higher affinity to a nucleic acid having a specific nucleotide sequence relative to a nucleic acid having a nucleotide sequence which is essentially unrelated to the specific nucleotide sequence. In a preferred embodiment, a nucleic acid binding domain is a "DNA binding domain".

"Operably linked" refers to an arrangement of elements wherein the components so described are configured so as to perform their usual function. Thus, an expression control sequence operably linked to a coding sequence permits expression of the coding sequence. The control sequence need not be contiguous with the coding sequence, so long as it functions to direct the expression thereof. Thus, for example, intervening untranslated yet transcribed sequences can be present between a promoter sequence and the coding sequence and the promoter sequence can still be considered "operably linked" to the coding sequence.

"Protein", "polypeptide" and "peptide" are used interchangeably herein when referring to a gene product, e.g., as may be encoded by a coding sequence.

A "recombinant virus" is a complete virus particle in which the packaged nucleic acid contains a heterologous portion.

"Subunit", when referring to the subunit of an activation domain, refers to a portion of the transcription activation domain.

A "target gene" is a nucleic acid of interest, the expression of which is modulated according to the methods of the invention. The target gene can be endogenous or exogenous and can integrate into a cell's genome, or remain episomal. The target gene can encode a protein or be a non coding nucleic acid, e.g, a nucleic acid which is transcribed into an antisense RNA or a ribozyme.

A "therapeutically effective dose" of ligand denotes a treatment- or prophylaxis-effective dose, e.g., a dose which yields detectable target gene transcription or cell growth, proliferation, differentiation, death, etc. in the genetically engineered cell, or a dose which is predicted to be treatment- or prophylaxis-effective by extrapolation from data obtained in animal or cell culture models. A therapeutically effective dose is ususally preferred for the treatment of a human or non-human mammal.

"Transcription control element" denotes a regulatory DNA sequence, such as initiation signals, enhancers, and promoters, which induce or control transcription of protein coding sequences with which they are operably linked. The term "enhancer" is intended to include regulatory elements capable of increasing, stimulating, or enhancing transcription from a promoter. Such transcription regulatory components can be present upstream of a coding region, or in certain cases (e.g. enhancers), in other locations as well, such as in introns, exons, coding regions, and 3' flanking sequences.

"Transcription factor" refers to any protein or modified form thereof that is involved in the initiation of transcription but which is not itself a part of the polymerase. Transcription factors are proteins or modified forms thereof, which interact preferentially with specific nucleic acid sequences, i.e., regulatory elements. Some transcription factors are active when they are in the form of a monomer. Alternatively, other transcription factors are active in the form of oligomers consisting of two or more identical proteins or different proteins (heterodimer). The factors have different actions during the transcription initiation: they may interact with other factors, with the RNA polymerase, with the entire complex, with activators, or with DNA. Transcription factors usually contain one or more transcription regulatory domains.

"Transcription regulatory domain" refers to any domain which regulates transcription, and includes both activation and repression domains. The term "transcription activation domain" denotes a domain in a transcription factor which positively regulates (increases) the rate of gene transcription. The term "transcription repression domain" denotes a domain in a transcription factor which negatively regulates (inhibits or decreases) the rate of gene transcription.

"Transfection" means the introduction of a naked nucleic acid molecule into a recipient cell. "Infection" refers to the process wherein a virus enters the cell in a manner whereby the genetic material of the virus can be expressed in the cell. A "productive infection" refers to the process wherein a virus enters the cell, is replicated, and then released from the cell (sometimes referred to as a "lytic" infection). "Transduction" encompasses the introduction of nucleic acid into cells by any means.

"Transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous to the animal or cell into which it is introduced, or comprises or is derived from an endogenous gene of the animal or cell into which it is introduced, but which is designed to be inserted, or is inserted, into the recipient's genome in such a way as to alter that genome. (e.g., it is inserted at a location which differs from that of the natural gene). Alternatively, a transgene can also be present in an episome. A transgene can include one or more expression control sequences and any other nucleic acid, (e.g. intron), that may be necessary or desirable for optimal expression of a selected coding sequence.

"Transient transfection" refers to cases where exogenous DNA does not integrate into the genome of a transfected cell, e.g., where episomal DNA is transcribed into mRNA and translated into protein. A cell has been "stably transfected" with a nucleic acid construct when the nucleic acid construct has been integrated into the genome of that cell.

By "virus" is meant a complete virus, such as a wild-type (wt) virus particle comprising a nucleic acid genome associated with a capsid protein coat, or a recombinant virus particle as described above. For example, an adenovirus is a complete virus particle, comprising an Ad nucleic acid genome associated with an Ad capsid protein coat.

"Wild-type" means naturally occurring in a normal cell.

This invention involves methods and materials for multimerizing fusion proteins in genetically engineered cells using a novel dimerization-based biological switch. The design and implementation of various dimerization-based biological switches has been reported, inter alia, in Spencer et al and in various international patent applications cited herein. Other accounts of successful application of this general approach have also been reported. Fusion proteins containing a domain from human FRAP fused to an effector domain have been disclosed in Rivera et al, 1996, Nature Medicine 2, 1028–1032 and in WO 96/41865 (Clackson et al) and WO 95/33052 (Berlin et al). As noted previously, the fusion proteins are designed such that association of the effector domains, through ligand-mediated "dimerization" or "multimerization" of the fusion proteins which contain them, triggers a desired biological event such as transcription of a desired gene, cell death, cell proliferation, etc. For example, clustering of fusion proteins containing an action domain derived from the intracellular portion of the T cell receptor CD3 zeta domain triggers transcription of a gene under the transcription control of the IL-2 promoter or promoter elements derived therefrom. In other embodiments, the action domain comprises a domain derived from the intracellular portion of a protein such as FAS or the TNF-alpha receptor (TNFalpha-R1), which are capable, upon oligomerization, of triggering apoptosis of the cell. In still other embodiments, the action domains comprise a DNA-binding domain such as GAL4 or ZFHD1 and a transcription activation domain such as VP16 or p65, paired such that oligomerization of the fusion proteins represents assembly of a transcription factor complex which triggers transcription of a gene linked to a DNA sequence recognized by (capable of specific binding interaction with) the DNA binding domain.

Fusion proteins containing one or more ligand-binding domains and one or more action domains, e.g. for activation of transcription of a target gene, triggering cell death or other signal transduction pathway, cellular localization, cell proliferation etc., are disclosed in WO 94/18317, PCT/US94/08008, Spencer et al, supra and Blau et al. (PNAS 1997 94:3076). The design and use of such fusion proteins for ligand-mediated gene-knock out and for ligand-mediated blockade of gene expression or inhibition of gene product function are disclosed in PCT/US95/10591. Novel DNA binding domains and DNA sequences to which they bind which are useful in embodiments involving regulated transcription of a target gene are disclosed, e.g., in Pomeranz et al, 1995, Science 267:93–96. Those references provide substantial information, guidance and examples relating to the design, construction and use of DNA constructs encoding analogous fusion proteins, target gene constructs, and other aspects which may also be useful to the practitioner of the subject invention.

By appropriate choice of fusion proteins, this invention permits one to activate the transcription of a desired gene; actuate cell growth, proliferation, differentiation or apoptosis, or trigger other biological events in engineered cells in an FK506-dependent manner analogous to the systems described in the patent documents and other references cited above. The engineered cells, preferably animal cells, may be growing or maintained in culture or may be present within whole organisms, as in the case of human gene therapy, transgenic animals, and other such applications. An FKBP/CAB ligand is administered to the cell culture or to the organism containing the engineered cells, as the case may be, in an amount effective to multimerize the FKBP fusion proteins and CAB fusion proteins (as may be observed indirectly by monitoring target gene transcription, apoptosis or other biological process so triggered). In the case of administration to whole organisms, the ligand may be administered in a composition containing the ligand and one or more acceptable veterinary or pharmaceutical diluents and/or excipients.

A compound which binds to one of the fusion proteins but does not form tripartite complexes with both fusion proteins may be used as a multimerization antagonist. As such it may be administered to the engineered cells, or to organisms containing them (preferably in a composition as described above in the case of administration to whole animals), in an amount effective for blocking or reversing the effect of the ligand, i.e. for preventing, inhibiting or disrupting multimerization of the fusion proteins. For instance, rapamycin, a rapalog, or any of the many synthetic FKBP ligands which do not form tripartite complexes with FKBP and CAB may be used as an antagonist.

One important aspect of this invention provides materials and methods for ligand-dependent, direct activation of transcription of a desired gene. In one such embodiment, a set of two or more different fusion proteins, and corresponding DNA constructs capable of directing their expression, is provided. One such fusion protein contains as its action domain(s) one or more transcription activation domains. The other fusion protein contains as its action domain(s) one or more DNA-binding domains. The selected ligand is capable of binding to both fusion proteins to form a dimeric or multimeric complex thus containing at least one DNA binding domain and at least one transcription activation domain. Formation of such complexes leads to activation of transcription of a target gene linked to, and under the transcription control of, a DNA sequence to which the DNA-binding domain is capable of binding, as can be observed by monitoring directly or indirectly the presence or concentration of the target gene product.

Preferably the DNA binding domain, and a fusion protein containing it, binds to its recognized DNA sequence with sufficient selectivity so that binding to the selected DNA sequence can be observed (directly or indirectly) despite the presence of other, often numerous other, DNA sequences. Preferably, binding of the fusion protein comprising the DNA-binding domain to the selected DNA sequence is at least two, more preferably three and even more preferably more than four orders of magnitude greater than binding to any one alternative DNA sequence, as measured by in vitro binding studies or by measuring relative rates or levels of transcription of genes associated with the selected DNA sequence as compared with any alternative DNA sequences.

Cells which have been genetically engineered to contain such a set of constructs, together with any desired accessory constructs, may be used in applications involving ligand-mediated, regulated actuation of the desired biological event, be it regulated transcription of a desired gene, regulated triggering of a signal transduction pathway such as the triggering of apoptosis, or another event. Cells engineered for regulatable expression of a target gene, for instance, can be used for regulated production of a desired protein (or other gene product) encoded by the target gene. Such cells may be grown in culture by conventional means. Addition of ligand to the culture medium containing the cells leads to expression of the target gene by the cells and production of the protein encoded by that gene. Expression of the gene and production of the protein can be turned off by withholding further ligand from the medium, by removing residual ligand from the medium, or by adding to the medium a multimerization antagonist reagent.

Engineered cells of this invention can also be produced and/or used in vivo, to modify whole organisms, preferably animals, especially humans, e.g. such that the cells produce a desired protein or other result within the animal containing them. Such uses include gene therapy applications.

Embodiments involving regulatable actuation of apoptosis provide engineered cells susceptible to FK506-inducible cell death. Such engineered cells can be eliminated from a cell culture or host organism after they have served their intended purposed (e.g. production of a desired protein or other product), if they have or develop unwanted properties, or if they are no longer useful, safe or desired. Elimination is effected by adding ligand to the medium or administering it to the host organism. In such cases, the action domains of the fusion proteins are protein domains such as the intracellular domains of FAS or TNF-R1, downstream components of their signaling pathways or other protein domains which upon oligomerization trigger apoptosis.

Said differently, this invention provides a method for achieving any of those objectives, e.g. activation of transcription of a target gene (typically a heterologous gene for a therapeutic protein), cell growth or proliferation, cell death or some other selected biological event, in an animal, preferably a human patient, in need thereof and containing engineered cells of this invention. That method involves administering to the animal a pharmaceutical composition containing the ligand by a route of administration and in an amount effective to cause multimerization of the fusion proteins in at least a portion of the engineered cells. Multimerization may be detected indirectly by detecting the occurrence of target gene expression, cell growth, proliferation or death, or other objective for which the fusion proteins were designed and the cells genetically engineered.

This invention further encompasses a pharmaceutical composition comprising a multimerization antagonist of this invention in admixture with a pharmaceutically acceptable carrier and optionally with one or more pharmaceutically acceptable excipients for inhibiting or otherwise reducing, in whole or part, the extent of multimerization of fusion proteins in engineered cells of this invention in a subject, and thus for de-activating the transcription of a target gene, for example, or turning off another biological result of this invention. Thus, the use of the multimerizing ligands and of the multimerization antagonist reagents to prepare pharmaceutical compositions and achieve their pharmacologic results is encompassed by this invention.

Also disclosed is a method for providing a host organism, preferably an animal, typically a non-human mammal or a human subject, responsive to a ligand of this invention. The method involves introducing into the organism cells which have been engineered in accordance with this invention, i.e. containing one or more nucleic acid constructs encoding the fusion proteins, and so forth. The engineered cells may be encapsulated using any of a variety of materials and methods before being introduced into the host organism. Alternatively, one can introduce the nucleic acid constructs of this invention into a host organism, e.g. a mammal, under conditions permitting incorporation thereof into one or more cells of the host mammal, e.g. using viral vectors, introduction of DNA by injection or via catheter, etc.

Also provided are kits for producing cells responsive to a ligand of this invention. One such kit contains one or more nucleic acid constructs encoding and capable of directing the expression of fusion proteins which, upon ligand-mediated oligomerization, trigger the desired biological response. The kit may contain a quantity of a ligand capable of multimerizing the fusion protein molecules encoded by the construct(s) of the kit, and may contain in addition a quantity of a multimerization antagonist. The kit may further contain a nucleic acid construct encoding a target gene (or cloning site) linked to a cognate DNA sequence which is recognized by the dimerized fusion proteins permitting transcription of a gene linked to that cognate DNA sequence in the presence of multimerized fusion protein molecules. The constructs may be associated with one or more selection markers for convenient selection of transfectants, as well as other conventional vector elements useful for replication in prokaryotes, for expression in eukaryotes, and the like. The selection markers may be the same or different for each different construct, permitting the selection of cells which contain each such construct(s).

The accessory construct for introducing into cells a target gene in association with a cognate DNA sequence may contain a cloning site in place of a target gene. A kit containing such a construct permits the engineering of cells for regulatable expression of a gene to be provided by the practitioner.

Other kits of this invention may contain one or two (or more) nucleic acid constructs for fusion proteins in which one or more contain a cloning site in place of the transcription activator or DNA binding protein, permitting the user to insert whichever such domain s/he wishes. Such a kit may optionally include other elements as described above, e.g. a nucleic acid construct for a target gene with or without a cognate DNA sequence for a pre-selected DNA binding domain.

Any of the kits may also contain positive control cells which were stably transformed with constructs of this invention such that they express a reporter gene (for CAT, beta-galactosidase or any conveniently detectable gene product) in response to exposure of the cells to the ligand. Reagents for detecting and/or quantifying the expression of the reporter gene may also be provided.

For further information and guidance on the design, construction and use of such systems or components thereof which may be adapted for use in practising the subject invention, reference to the following publications is suggested: Spencer et al, 1993, supra; Rivera et al, 1996, supra; Spencer et al, 1996, Current Biology 6, 839–847; Luo et al, 1996, Nature, 383, 181–185; Ho et al, 1996, Nature 382, 822–826; Belshaw et al, 1996, Proc. Natl. Acad. Sci. USA 93, 4604–4607; Spencer, 1996, TIG 12(5), 181–187; Spencer et al, 1995, Proc., Natl. Acad. Sci. USA 92, 9805–9809; Holsinger et al, 1995, Proc. Natl. Acad. Sci. USA 92, 9810–9814; Pruschy et al, 1994, Chemistry & Biology 1(3), 163–172; and published international patent applications WO 94/18317, WO 95/02684, WO 95/33052, WO 96/20951 and WO 96/41865.

FKBP Domains and Fusion Proteins

The FKBP fusion protein comprises at least one FKBP domain containing all or part of the peptide sequence of an FKBP domain and at least one heterologous action domain. This fusion protein must be capable of binding to ligand, preferably with a Kd value below about 100 nM, more preferably below about 10 nM and even more preferably below about 1 nM, as measured by direct binding measurement (e.g. fluorescence quenching), competition binding measurement (e.g. versus FK506), inhibition of FKBP enzyme activity (rotamase), or other assay methodology. Typically the fusion protein will contain one or more protein domains comprising peptide sequence selected from that of a naturally occurring FKBP protein such as human FKBP12, e.g. as described in International Patent Application PCT/US94/01617. That peptide sequence may be modified to adjust the binding specificity, usually with replacement, insertion or deletion of 10 or fewer, preferably 5 or fewer, in some cases 1–3, and often 1, amino acid residue. Such modifications are elected in certain embodiments to yield one or both of the following binding profiles: (a) binding of a ligand to the modified FKBP domain, or fusion protein containing it, preferably at least one, and more preferably at least two, and even more preferably three or four or more, orders of magnitude better (by any measure) than to FKBP12 or the FKBP endogenous to the host cells to be engineered; and (b) binding of the FKBP:ligand complex to the CAB fusion protein, preferably at least one, and more preferably at least two, and even more preferably at least three, orders of magnitude better (by any measure) than to the calcineurin endogenous to the host cell to be engineered.

The FKBP fusion protein also contains at least one heterologous action domain, i.e., a protein domain containing non-FKBP peptide sequence. The action domain may be a DNA-binding domain, transcription activation domain, transcription repression domain, cellular localization domain, intracellular signal transduction domain, etc., e.g. as described elsewhere herein or in PCT/US94/01617 or the other cited references. Generally speaking, the action domain is capable of directing the fusion protein to a selected cellular location or of initiating a biological effect upon association or aggregation with another action domain, for instance, upon multimerization of proteins containing the same or different action domains.

A recombinant nucleic acid encoding such a fusion protein will be capable of selectively hybridizing to a DNA encoding the parent FKBP protein, e.g. human FKBP12, or would be capable of such hybridization but for the degeneracy of the genetic code. Since these fusion proteins contain an action domain derived from another protein, e.g. Gal4, ZFHD1, p65, VP16, FAS, CD3 zeta chain, etc., the recombinant DNA encoding the fusion protein will also be capable of selectively hybridizing to a DNA encoding that other protein, or would be capable of such hybridization but for the degeneracy of the genetic code.

FKBP fusion proteins of this invention, as well as CAB fusion proteins discussed in further detail below, may contain one or more copies of one or more different ligand binding domains and one or more copies of one or more action domains. The ligand binding domain(s) (i.e., FKBP and CAB domains) may be N-terminal, C-terminal, or interspersed with respect to the action domain(s). Embodiments involving multiple copies of a ligand binding domain usually have 2, 3 or 4 such copies. For example, an FKBP fusion protein may contain 2, 3 or 4 FKBP domains. The various domains of the FKBP fusion proteins (and of the CAB fusion proteins discussed below) are optionally separated by linking peptide regions which may be derived from one of the adjacent domains or may be heterologous.

Illustrative examples of FKBP fusion proteins useful in the practice of this invention include the FKBP fusion proteins disclosed in PCT/US94/01617 (Stanford & Harvard), PCT/US94/08008 (Stanford & Harvard), Spencer et al (supra), PCT/US95/10591 (ARIAD), PCT/US95/06722 (Mitotix, Inc.) and other references cited herein; the FKBP fusion proteins disclosed in the examples which follow; variants of any of the foregoing FKBP fusion proteins which contain up to 10 (preferably 1–5) amino acid insertions, deletions or substitutions in one or more of the FKBP domains and which are still capable of binding to a ligand; variants of any of the foregoing FKBP fusion proteins which contain one or more copies of an FKBP domain which is encoded by a DNA sequence capable of selectively hybridizing to a DNA sequence encoding a naturally occurring FKBP domain and which are still capable of binding to a ligand; variants of any of the foregoing in which one or more heterologous action domains are deleted, replaced or supplemented with a different heterologous action domain; variants of any of the foregoing FKBP fusion proteins which are capable of binding to an FKBP/CAB ligand and which contain an FKBP domain derived from a non-human source; and variants of any of the foregoing FKBP fusion proteins which contain one or more amino acid residues corresponding to Tyr26, Phe36, Asp37, Arg42, Phe46, Phe48, Glu54, Val55, or Phe99 of human FKBP12 in which one or more of those amino acid residues is replaced by a different amino acid, the variant being capable of binding to a ligand.

For instance, in a number of cases the FKBP fusion proteins comprise multiple copies of an FKBP domain containing amino acids 1–107 of human FKBP12, separated by the 2-amino acid linker Thr-Arg encoded by ACTAGA, the ligation product of DNAs digested respectively with the restriction endonucleases SpeI and XbaI. The following table provides illustrative subsets of mutant FKBP domains based on the foregoing FKBP12 sequence:

| Illustrative Mutant FKBPs | | | |
|---|---|---|---|
| F36A | Y26V | F46A | W59A |
| F36V | Y26S | F48H | H87W |
| F36M | D37A | F48L | H87R |
| F36S | I90A | F48A | F36V/F99A |
| F99A | I91A | E54A | F36V/F99G |
| F99G | F46H | E54K | F36M/F99A |
| Y26A | F46L | V55A | F36M/F99G | note: Entries identify the native amino acid by single letter code and sequence position, followed by the replacement amino acid in the mutant. Thus, F36V designates a human FKBP12 sequence in which phenylalanine at position 36 is replaced by valine. F36V/F99A indicates a double mutation in which phenylalanine at positions 36 and 99 are replaced by valine and alanine, respectively.

Cyclophilin Domains and Fusion Proteins

Cyclophilin fusion proteins may contain all or part of murine cyclophilin C (e.g. residues 36–212; Freidman et al., Cell 664(1991) 799–806) or human cyclophilin C (Genbank Accession number S71018; Schneider et al., Biochemistry 33 (27), 8218–8224 (1994)). These fusion proteins contain a heterologous action domain and form complexes with a cyclophilin/CAB ligand, such as cyclosporin, as described above for FKBP fusion proteins. Cyclophilin domains may also be modified to adjust the binding specificity, usually with replacement, insertion or deletion of 10 or fewer, preferably 5 or fewer, in some cases 1–3, and often 1, amino acid residue, again as described in detail above for FKBP domains. In general, any description of FKBP domains and fusion proteins and their use in this invention is applicable to cyclophilin domains as well. Cyclophilin domains and their use in chimeric proteins are described in U.S. Pat. No. 5,830,462, in particular example 4c, the full contents of which are incorporated herein by reference.

CAB Domains and Fusion Proteins

The structure of FKBP-FK506 complexed to calcineurin phosphatase (Griffith et al., Cell, 82:507–522, 1995) has been reported. Calcineurin A (residues 12–394) was shown to be effective as a dimerization domain using a three hybrid system in yeast using three FKBPs fused to Gal4 and residues 12–394 of murine calcineurin A fused C-terminally to the Gal4 activation domain (Ho, 1996 Nature. 382: 822–826). Addition of FK506 activated transcription of a reporter gene in these cells. This system is not optimal, however, because it requires a complex to form between endogenous calcineurin B and the calcineurin A fusion protein. In addition, the calcineurin fusion protein might interfere with the calcineurin signaling pathway.

The present invention provides a "minimal" calcineurin domain, termed a CAB, which is a smaller, more manipulatable domain that can be used in a general way to control dimerization of proteins for the purposes of regulating biological processes. A CAB domain of this invention must be able to form a complex with FKBP in the presence of an FKBP/CAB ligand. In other embodiments, the CAB domain can form a tripartite complex with a cyclophilin domain and cyclosporin. Thus, one of the most compelling potential features of the CAB as a dimerization domain is its ability to dock with two different partners under the control of two different ligands. With this system, a single dimerization domain (i.e. the CAB) can interact with two other protein partners simultaneously or competitively, depending on the particular drug added. The same is also true for FKBP which is now capable of being recruited to either FRAP in the presence of rapamycin or a rapalog or to CAB in the presence of an FKBP/CAB ligand.

Figure 6A:
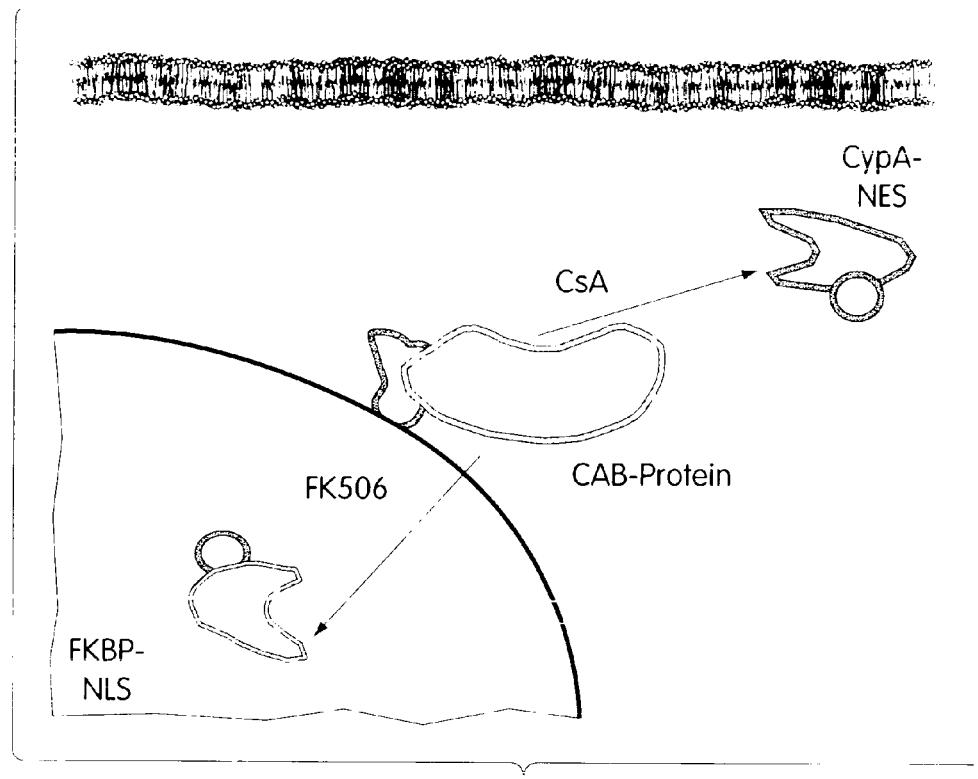
FIG. 6: Schematic depictions of three-construct systems involving the CAB dimerization domain. A Recruitment of a CAB fusion protein to either FKBP in the context of a nuclear localization signal (NLS) or cyclophilin A (CypA) in the context of a nuclear export signal (NES). B. Recruitment of kinases fused to either the CAB domain or the FRB domain to FKBP localized to the plasma membrane by virtue of a CaaX isoprenylation signal.

Since the CAB should bind both the FK506:FKBP complex and the cyclosporin:cyclophilin complex, one can engineer cells or animals in which a fusion of the CAB to a heterologous action domain is present in the same cell as two other fusion proteins, one containing FKBP and one containing cyclophilin. Addition of FK506 to these cells results in the formation of an FKBP/FK506/CAB complex, while addition of cyclosporin to the same cell would result in a cyclophilin/cyclosporin/CAB complex. An example of this situation is illustrated in FIG. 6A.

Figure 6B:
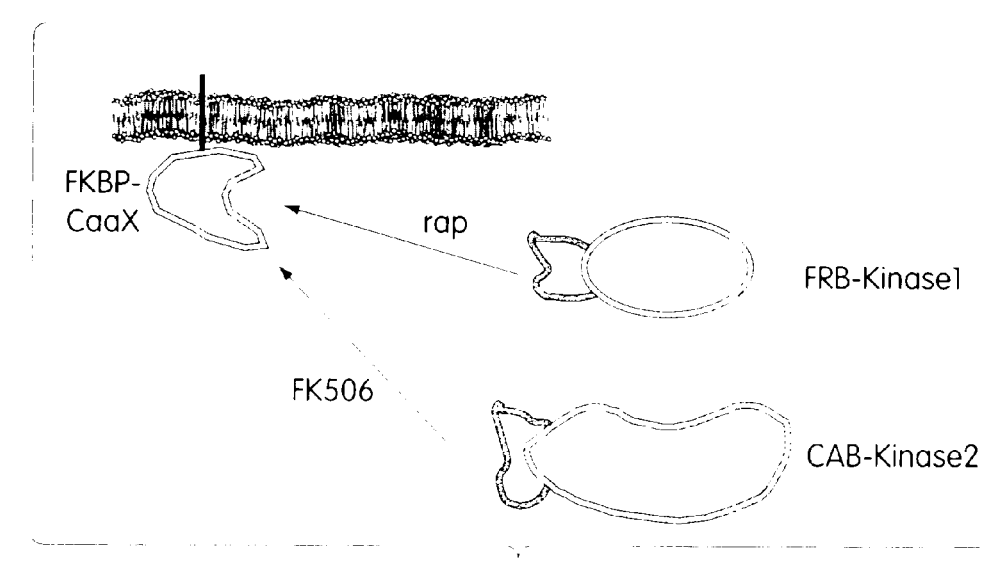

Furthermore, since FKBP is required to mediate the interactions between both FK506 or rapamycin and their cellular targets, one can engineer cells or animals in which a fusion of the CAB to a heterologous action domain is present in the same cell as a fusion protein containing an FRB domain. FRB domains are described in detail in WO 95/33052 and in WO 96/41865. In this embodiment, addition of FK506 to the cell induces the formation of an FKBP/FK506/CAB complex, while addition of rapamycin should result in the formation of an FKBP/rapamycin/FRB complex. This allows for complex order of addition experiments in cell culture or for more complex control over signal transduction processes that require localization or protein association for function. An example of this situation is illustrated in FIG. 6B.

CAB domains of this invention are composite ligand binding domains, comprising a portion of calcineurin A and a portion of calcineurin B, such that the resulting composite ligand binding domain contains the surface of calcineurin phosphatase that contacts the FKBP-FK506 complex. The region of calcineurin that has been truncated contains the autoregulatory and calmodulin domains, which are not involved in FKBP binding. By way of example, the nucleic acid and amino acid sequences of human calcineurin A are provided in SEQ ID NO: 32 and SEQ ID NO: 33, respectively, and the nucleic acid and amino acid sequences of human calcineurin B are provided in SEQ ID NO: 34 and SEQ ID NO: 35, respectively. The portion of calcineurin A used in the examples includes residues 12 to 394 or residues 12 to 370 of human calcineurin A in the full length CABS, however, equivalent regions of the calcineurin gene from other species could also be used. For example, one may desire to use the sequence of the mouse or rat genes for the construction of transgenic animals. The N or C terminus of the calcineurin A portion could also be shortened or extended, if desired. The 12–394 CABSs contain an active phosphatase domain, while the 12–370 CABs have an H151A mutation in calcineurin A that abolishes the phosphatase activity.

The calcineurin B portion of the CABs described in the examples contains residues 2 or 3 to 170 of human calcineurin B. The N-terminal methionine (residue 1) or methionine and glycine (residue 1 and residue 2) can be removed to prevent processing or myristoylation of calcineurin B at its N-terminus and to remove an alternative start site for translation. The calcineurin B portion of the composite domain may also be shortened, if desired. Literature references and Genbank accession numbers for various calcineurin genes are given in the table below:

| Species | Calcineurin A Genbank # | Reference | Calcineurin B Genbank # | Reference |
|---|---|---|---|---|
| Human | M29550 | Guerini and Klee, PNAS USA 86, 9183–9187 (1989). | M30773 | Guerini et al., DNA 8(9), 675–682 (1989). |
| Rat | D90035 | Ito et al., BBRC 163(3), 1492–1497 (1989). | D14568 | Chang et al., BBA 1217(2), 174–180 (1994). |
| Bovine | U33868 | Griffith et al., Cell, 82:507–522, (1995) | X71666 | Nargang et al., DNA seq 4(5), 313–318 (1994). |
| Mouse | M81483 | Guerini and Klee, PNAS USA 86, 9183–9187 (1989). | S43864 | Ueki et al., BBRC 187(1), 537–543 (1992) |

The distance between residue 370 of calcineurin A and the N-terminus of calcineurin B is 17.5 Angstroms, as determined from the crystal structure. Thus, when the CAB domain is constructed in such a way that the calcineurin A portion is N-terminal to the calcineurin B portion, only a small linker region is necessary to connect the two. In fact, since the structure indicates that calcineurin A maintains a rigid structure only as far as residue 370, the C-terminus of calcineurin A can be linked directly to the N-terminus of calcineurin B, thereby using residues 370–394 of calcineurin A as the linker region. Hence, a preferred embodiment of the invention comprises a CAB domain composed of residues 12–394 of calcineurin A fused N-terminally to residues 3–170 of calcineurin B.

The CAB fusion protein comprises at least one CAB domain and at least one heterologous action domain, i.e., a protein domain containing non-CAB peptide sequence. The action domain may be a DNA-binding domain, transcription activation domain, transcription repression domain, cellular localization domain, intracellular signal transduction domain, etc., e.g. as described elsewhere herein or in PCT/US94/01617 or the other cited references. Generally speaking, the action domain is capable of directing the fusion protein to a selected cellular location or of initiating a biological effect upon association or aggregation with another action domain, for instance, upon multimerization of proteins containing the same or different action domains. As described in the examples, both CAB-VP16 fusion proteins and CAB-GAL4 fusion proteins are functional in SEAP reporter assays. As in the case of FKBP fusion proteins, the CAB domains should be able to hybridize with either calcineurin A or calcineurin B or portions thereof, or would be able to but for the degeneracy of the genetic code.

A shorter version of the CAB domain, termed the mini CAB, comprises residues 340–394 of calcineurin A fused N-terminally to residues 3–170 of calcineurin B. This construct eliminates the phosphatase domain of calcineurin and provides a less bulky protein for use in the dimerization system. Example 8 shows that the mini CAB can work as well as the full length CABs in reporter assays. As described above for FKBPs, CAB fusion proteins of this invention may contain one or more copies of the ligand binding domain and one or more copies of one or more action domains. The CAB domain may be N-terminal, C-terminal, or interspersed with respect to the action domain(s). Embodiments involving multiple copies of a ligand binding domain usually have 2, 3 or 4 such copies. For example, a CAB fusion protein may contain 2, 3, or 4 CAB domains, although currently, the preferred embodiment for regulated transcription contains 2 CAB domains.

Mixed Fusion Proteins

A third type of fusion protein comprises one or more FKBP domains, one or more heterologous action domains, and one or more CAB domains as described for the CAB fusion proteins.

Mixed fusion protein molecules are capable of forming homodimeric or homomultimeric protein complexes in the presence of an FKBP/CAB ligand to which they bind. Embodiments involving mixed fusion proteins have the advantage of requiring the introduction into cells of a single recombinant nucleic acid construct in place of two recombinant nucleic acid constructs otherwise required to direct the expression of both an FKBP fusion protein and a CAB fusion protein.

A recombinant DNA encoding a mixed fusion protein will be capable of selectively hybridizing to a DNA encoding an FKBP protein, a DNA encoding calcineurin A or B, and a heterologous DNA sequence encoding the protein from which one or more effector domains is derived (e.g. Gal4, VP16, Fas, CD3 zeta chain, etc.), or would be capable of such hybridization but for the degeneracy of the genetic code.

Heterologous Domains

As mentioned above, the heterologous action domains of the fusion proteins are protein domains which, upon mutual association of the fusion proteins bearing them, are capable of triggering (or inhibiting) events such as DNA-binding and/or transcription of a target gene; actuating cell growth, differentiation, proliferation or apoptosis; directing proteins to a particular cellular location; or actuating other biological events.

Embodiments involving regulatable gene transcription involve the use of target gene constructs which comprise a target gene (which encodes a polypeptide, antisense RNA, ribozyme, etc. of interest) under the transcription control of a DNA element responsive to the association or multimerization of the heterologous domains of the 1st and 2d fusion proteins.

In embodiments of the invention involving direct activation of transcription, the heterologous domains of the 1st and 2nd fusion proteins comprise a DNA binding domain such as Gal4 or a fusion DNA binding domain such as ZFHD1, and a transcription activation domain such as those derived from VP16 or p65, respectively. The multimerization of a fusion protein containing such a transcription activation domain to a fusion protein containing a DNA binding domain targets the transcription factor to the expression control sequence to which the DNA binding domain binds, and thus activates the transcription of a target gene linked to that expression control sequence. Foregoing the transcription activation domain or substituting a repressor domain (see PCT/US94/01617) in place of a transcription activation domain provides an analogous fusion protein useful for inhibiting transcription of a target gene. Composite DNA binding domains and DNA sequences to which they bind are disclosed in Pomerantz et al, 1995, supra, the contents of which are incorporated herein by reference. Such composite DNA binding domains may be used as DNA binding domains in the practice of this invention, together with a target gene construct containing the cognate DNA sequences to which the composite DBD binds.

In embodiments involving indirect activation of transcription, the heterologous domains of the fusion proteins are action domains of signaling proteins which upon aggregation or multimerization trigger the activation of transcription under the control of a responsive promoter. For example, the signaling domain may be the intracellular domain of the zeta subunit of the T cell receptor, which, upon aggregation, triggers transcription of a gene linked to the IL-2 promoter or a derivative thereof (e.g. iterated NF-AT binding sites). Alternatively, the signaling domain may be a cell surface receptor such as the erythropoietin receptor, which can initiate cell proliferation upon multimerization.

In another aspect of the invention, the heterologous domains are protein domains which upon mutual association are capable of triggering cell death. Examples of such domains are the intracellular domains of the Fas antigen or of the TNF R1. Fusion proteins containing a Fas domain can be designed and prepared by analogy to the disclosure of PCT/US94/01617.

Engineered Receptor Domains

As noted previously, the FKBP and CAB domains may contain peptide sequence selected from the peptide sequences of naturally occurring FKBP and CAB domains. Naturally occurring sequences include those of human FKBP12 and portions of human calcineurin A or calcineurin B. Alternatively, the peptide sequences may be derived from such naturally occurring peptide sequences but contain generally up to 10, and preferably 1–5, mutations in one or both such peptide sequences. As disclosed in greater detail elswhere herein, such mutations can confer a number of important features. For instance, an FKBP domain may be modified such that it is capable of binding an improved ligand preferentially, i.e. at least one, preferably two, and even more preferably three or four or more orders of magnitude more effectively, with respect to ligand binding by the unmodified FKBP domain. A CAB domain may be modified such that it is capable of binding a (modified or unmodified) FKBP:ligand complex preferentially, i.e. at least one, preferably two, and even more preferably three orders of magnitude more effectively, with respect to the unmodified CAB domain. FKBP and CAB domains may be modified such that they are capable of forming a tripartite complex with an improved ligand, preferentially, i.e. at least one, preferably two, and even more preferably three orders of magnitude more effectively, with respect to unmodified FKBP and CAB domains.

Methods for identifying FKBP mutations that confer enhanced ability to bind derivatives of FK506 containing various substituents ("bumps") were disclosed in U.S. Pat. No. 5,830,462. In this approach, molecular modelling is used to identify candidate amino acid substitutions in the FKBP domain that would accommodate the ligand substituent(s), and site-directed mutagenesis may then be used to engineer the protein mutations so identified. The mutants are expressed by standard methods and their binding affinity for the ligands measured, for example by inhibition of rotamase activity, or by competition for binding with a molecule such as FK506, if the mutant retains appropriate activity/affinity.

A similar strategy can be used to identify bump-hole pairs for the CAB domain. An exemplary FKBP/CAB ligand is C40-phenyl-FK506. This compound appears to be at least 30-fold less immunosuppressive than FK506 as measured by its dose-dependent suppression of PMA/ionomycin-induced activation of an NFAT-SEAP reporter in transient transfection experiments.

Without being bound by a particular theory, the inability of C40-phenyl-FK506 to inhibit NFAT-SEAP activity can be understood as a failure of the FKBP12/C40-phenyl-FK506 complex to bind endogenous calcineurin. The inhibition of NFAT-SEAP activity by FK506 is known to require binding of the FKBP12/FK506 complex to calcineurin, which results in a loss of calcineurin phosphatase activity (J. Liu, et al. Cell, 1991; 66: 807–815. J. Liu et al., Biochemistry, 1992; 31: 3896–3901). Indeed, the crystal structure of FKBP12/FK506 with the calcineurin heterodimer reveals that the terminal C39–C40 olefin of FK506 protrudes into the protein—protein interface between calcineurin A and calcineurin B (J. P. Griffith, et al Cell, 1995; 82(3): 507–522.) Grafting a model of the phenyl group of C40-phenyl-FK506 onto this structure allows the identification of several residues of calcineurin (W352, S353, and F356 from calcineurin A; L116, M119, and V120 from calcineurin B) whose side chains might be responsible for the steric interference which abrogates binding. Each of the residues in question is part of the CAB minimal binding domain structure. Thus, these residues may be mutated randomly or rationally to obtain a "holed" CAB which accommodates bumped FK506. These mutations may be inserted randomly or in a directed fashion, as described above for FKBP.

An alternative to iterative engineering and testing of single or multiple mutants is to co-randomize structurally-identified residues that are or would be in contact with or near one or more ligand or FK506 substituents. A collection of polypeptides containing FKBP or CAB domains randomized at the identified positions (such as are noted in the foregoing paragraph) is prepared e.g. using conventional synthetic or genetic methods. Such a collection represents a set of receptor domains containing replacement amino acids at one or more of such positions. The collection is screened and variants are selected which possess the desired ligand binding properties. In general, randomizing several residues simultaneously is expected to yield compensating mutants of higher affinity and specificity for a given bumped ligand as it maximizes the likelihood of beneficial cooperative interactions between sidechains. Techniques for preparing libraries randomized at discrete positions are known and include primer-directed mutagenesis using degenerate oligonucleotides, PCR with degenerate oligonucleotides, and cassette mutagenesis with degenerate oligonucleotides (see for example Lowman, H. B, and Wells, J. A. Methods: Comp. Methods Enzymol. 1991. 3, 205–216; Dennis, M. S. and Lazarus, R. A. 1994. J. Biol. Chem. 269, 22129–22136; and references therein).

We further contemplate that in many cases, randomization of only the few residues in or near direct contact with a given position in FK506 may not completely explore all the possible variations in FKBP or CAB conformation that could optimally accommodate a ligand substituent (bump). Thus the construction is also envisaged of unbiased libraries containing random substitutions that are not based on structural considerations, to identify subtle mutations or combinations thereof that confer preferential binding to bumped ligands. Several suitable mutagenesis schemes have been described, including alanine-scanning mutagenesis (Cunningham and Wells (1989) Science 244, 1081–1085), PCR misincorporation mutagenesis (see eg. Cadwell and Joyce, 1992, PCR Meth. Applic. 2, 28–33), and 'DNA shuffling' (Stemmer, 1994, Nature 370, 389–391 and Crameri et al, 1996, Nature Medicine 2, 100–103). These techniques produce libraries of random mutants, or sets of single mutants, that are then searched by screening or selection approaches.

In many cases, an effective strategy to identify the best mutants for preferential binding of a given bump is a combination of structure-based and unbiased approaches. See Clackson and Wells, 1994, Trends Biotechnology 12, 173–184 (review). For example we contemplate the construction of libraries in which key contact residues are randomized by PCR with degenerate oligonucleotides, but with amplification performed using error-promoting conditions to introduce further mutations at random sites. A further example is the combination of component DNA fragments from structure-based and unbiased random libraries using DNA shuffling.

Screening of libraries for desirable mutations may be performed by use of a yeast 2-hybrid system (Fields and Song (1989) Nature 340, 245–246). For example, a CAB-VP16 fusion may be introduced into one vector, and a library of randomized FKBP sequences cloned into a separate GAL4 fusion vector. Yeast co-transformants are treated with ligand, and those harboring complementary FKBP mutants are identified by for example beta-galactosidase or luciferase production (a screen), or survival on plates lacking an essential nutrient (a selection), as appropriate for the vectors used. The requirement for bumped FK506 to bridge the FKBP-CAB interaction is a useful screen to eliminate false positives.

A further strategy for isolating modified ligand-binding domains from libraries of FKBP (or cyclophilin or CAB) mutants utilizes a genetic selection for functional dimer formation described by Hu et. al. (Hu, J. C., et al. 1990. Science. 250:1400–1403; for review see Hu, J. C. 1995. Structure. 3:431–433). This strategy utilizes the fact that the bacteriophage lambda repressor cI binds to DNA as a homodimer and that binding of such homodimers to operator DNA prevents transcription of phage genes involved in the lytic pathway of the phage life cycle. Thus, bacterial cells expressing functional lambda repressor are immune to lysis by superinfecting phage lambda. Repressor protein comprises an amino terminal DNA binding domain (amino acids 1–92), joined by a 40 amino acid flexible linker to a carboxy terminal dimerization domain. The isolated N-terminal domain binds to DNA with low affinity due to inefficient dimer formation. High affinity DNA binding can be restored with heterologous dimerization domains such as the GCN4 "leucine zipper". Hu et al have described a system in which phage immunity is used as a genetic selection to isolate GCN4 leucine zipper mutants capable of mediating lambda repressor dimer formation from a large population of sequences (Hu et. al., 1990).

For example, to use the lambda repressor system to identify FRAP mutants complementary to bumped ligands, lambda repressor-FRAP libraries bearing mutant FRAP sequences are transformed into E. coli cells expressing wildtype lambda repressor-FKBP protein. Plasmids expressing FRAP mutants are isolated from those colonies that survive lysis on bacterial plates containing high titres of lambda phage and "bumped" FK506 compounds. Alternatively, to isolate FKBP mutants, the above strategy is repeated with lambda repressor-FKBP libraries bearing mutant FKBP sequences transformed into E. coli cells expressing wildtype lambda repressor-FRAP protein.

A further alternative is to clone the randomized FKBP sequences into a vector for phage display, allowing in vitro selection of the variants that bind best to the ligand. Affinity selection in vitro may be performed in a number of ways. For example, ligand is mixed with the library phage pool in solution in the presence of CAB tagged with an affinity handle (for example a hexa-histidine tag, or GST), and the resultant complexes are captured on the appropriate affinity matrix to enrich for phage displaying FKBP harboring complementary mutations. Techniques for phage display have been described, and other in vitro selection selection systems can also be contemplated (for example display on lambda phage, display on plasmids, display on baculovirus). Furthermore, selection and screening strategies can also be used to improve other properties of benefit in the application of this invention, such as enhanced stability in vivo. For a review see Clackson, T. & Wells, J. A. 1994. Trends Biotechnol. 12, 173–184.

Additionally, in optimizing the receptor domains of this invention, it should be appreciated that immunogenicity of a polypeptide sequence is thought to require the binding of peptides by MHC proteins and the recognition of the presented peptides as foreign by endogenous T-cell receptors. It may be preferable, at least in human gene therapy applications, to tailor a given foreign peptide sequence, including junction peptide sequences, to minimize the probability of its being immunologically presented in humans. For example, peptide binding to human MHC class I molecules has strict requirements for certain residues at key 'anchor' positions in the bound peptide: eg. HLA-A2 requires leucine, methionine or isoleucine at position 2 and leucine or valine at the C-terminus (for review see Stern and Wiley (1994) Structure 2, 145–251). Thus in engineering proteins in the practice of this invention, this periodicity of these residues is preferably avoided, especially in human gene therapy applications. The foregoing applies to all protein engineering aspects of the invention, including without limitation the engineering of point mutations into receptor domains, and to the choice or design of boundaries between the various protein domains.

Ligands

Modified FKBP ligands for use with engineered FKBP domains have been extensively described in the scientific literature and in published patent applications, including WO 94/18317 and U.S. Pat. No. 5,830,462. A number of modified FKBP/CAB ligands have been identified and synthesized, including C40-phenyl-FK506, C40-p-phenoxyphenyl-FK506, C40-p-biphenyl-FK506, C40-beta-naphthyl-FK506, C40-m-fluorophenyl-FK506, C40-p-iodophenyl-FK506, and "C41"-trimethylsilyl-FK506. The synthesis of FKBP/CAB ligands is described in Example 9.

Figure 3:
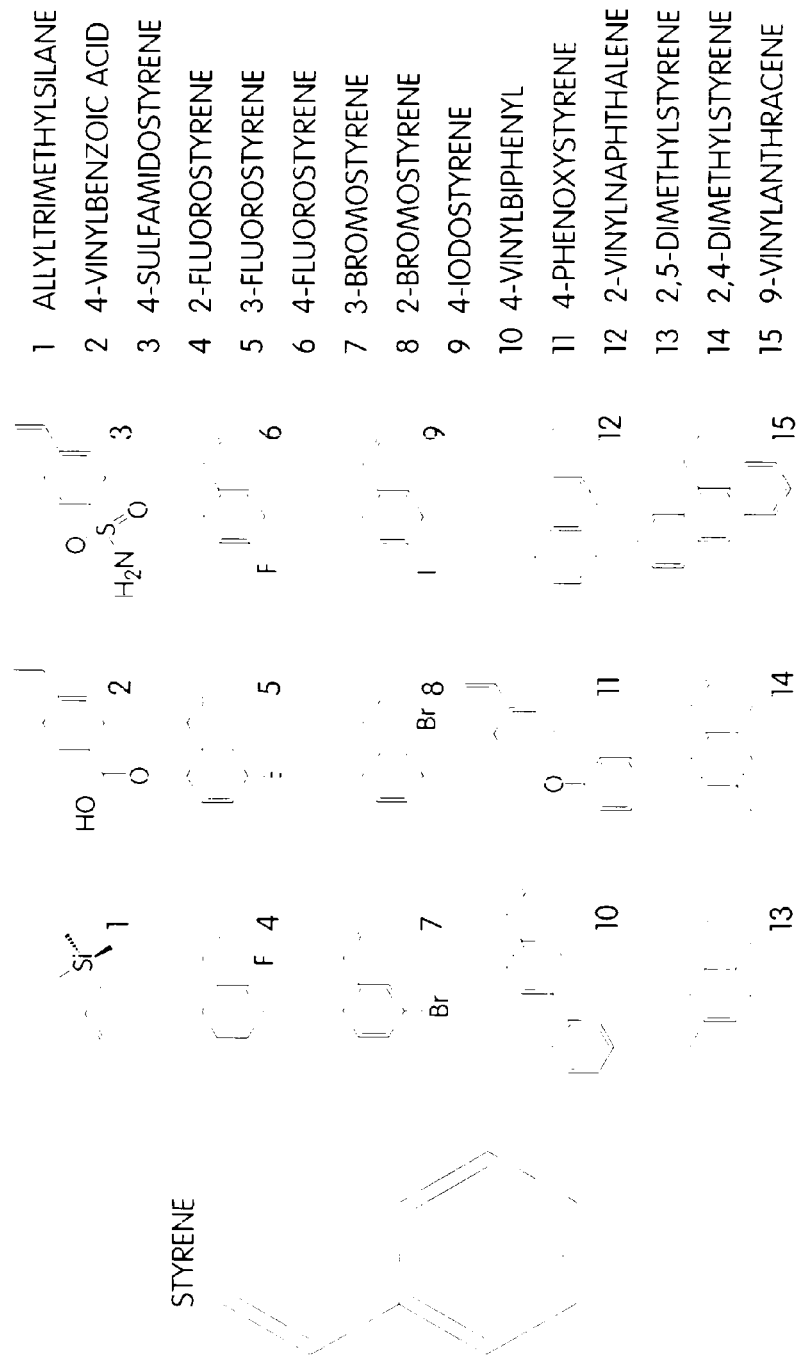
FIG. 3: Styrene analogs to be used in cross-metathesis reaction with FK506.

Each of these compounds is made using the appropriate styrene derivative, except for "C41"-trimethylsilyl-FK506 which uses allyltrimethylsilane, coupled to FK506's terminal olefin using the Grubbs catalyst to facilitate the olefin metathesis chemistry. As shown in FIG. 3, any styrene derivative may be added at the C40 position of FK506 using the methods described in Example 9. By such means one may prepare a wide variety of aryl- and heteroaryl-substituted C40 FK506 derivatives which can be used in the practice of this invention.

Modified cyclosporin A derivatives have also been prepared and are described in detail in U.S. Pat. No. 5,830,462, especially example 22, and in WO 98/08956, example 1, the full contents of which are incorporated herein by reference.

Other Components, Design Features and Applications

The fusion proteins may contain as a heterologous domain a cellular localization domain such as a membrane retention domain. See e.g. PCT/US94/01617, especially pages 26–27. Briefly, a membrane retention domain can be isolated from any convenient membrane-bound protein, whether endogenous to the host cell or not. The membrane retention domain may be a transmembrane retention domain, i.e., an amino acid sequence which extends across the membrane as in the case of cell surface proteins, including many receptors. The transmembrane peptide sequence may be extended to span part or all of an extracellular and/or intracellular domain as well. Alternatively, the membrane retention domain may be a lipid membrane retention domain such as a myristoylation or palmitoylation site which permits association with the lipids of the cell surface membrane. Lipid membrane retention domains will usually be added at the 5' end of the coding sequence for N-terminal binding to the membrane and, proximal to the 3' end for C-terminal binding. Peptide sequences involving post-translational processing to provide for lipid membrane binding are described by Carr, et al., PNAS USA (1988) 79, 6128; Aitken, et al., FEBS Lett. (1982) 150, 314; Henderson, et al., PNAS USA (1983) 80, 319; Schulz, et al., Virology (1984), 123, 2131; Dellman, et al., Nature (1985) 314, 374; and reviewed in Ann. Rev. of Biochem. (1988) 57, 69. An amino acid sequence of interest includes the sequence M-G-S-S-K-S-K-P-K-D-P-S-Q-R (SEQ ID NO 1). Various DNA sequences can be used to encode such sequences in the various fusion proteins of this invention. Other localization domains include organelle-targeting domains and sequences such as—K-D-E-L (SEQ ID NO 2) and -H-D-E-L (SEQ ID NO 3) which target proteins bearing them to the endoplasmic reticulum, as well as nuclear localization sequences which are particularly useful for fusion proteins designed for (direct) transcription regulation. Various cellular localization sequences and signals are well known in the art.

Other fusion proteins may contain a bundling domain as a heterologous domain. These domains, such as the lac repressor tetramerization domain constitutively oligomerize proteins containing such domains. Bundling domains may be used to deliver additional copies of activation domains or DNA binding domains to a given promoter.

Further details which may be used in the practice of the subject invention relating to the design, assembly and use of constructs encoding fusion proteins containing various action domains including cytoplasmic signal initiation domains such as the CD3 zeta chain, nuclear transcription factor domains including among others VP16 and GAL4, domains capable of triggering apoptosis including the Fas cytoplasmic domain and others are disclosed in PCT/US94/01617 and PCT/US95/10591. The latter international application further discloses additional features particularly applicable to the creation of genetically engineered animals which may be used as disease models in biopharmaceutical research. Those features include the use of tissue specific regulatory elements in the constructs for expression of the fusion proteins and the application of regulated transcription to the expression of Cre recombinase as the target gene leading to the elimination of a gene of interest flanked by loxP sequences. Alternatively, flp and its cognate recognition sequences may be used instead of Cre and lox. Those features may be adapted to the subject invention.

In various cases, especially in embodiments involving whole animals containing cells engineered in accordance with this invention, it will often be preferred, and in some cases required, that the various domains of the fusion proteins be derived from proteins of the same species as the host cell. Thus, for genetic engineering of human cells, it is often preferred that the heterologous domains (as well as the FKBP and CAB domains) be of human origin, rather than of bacterial, yeast or other non-human source.

We also note that epitope tags may also be incorporated into fusion proteins of this invention to permit convenient detection.

Tissue-Specific or Cell-Type Specific Expression

It will be preferred in certain embodiments, that the fusion proteins be expressed in a cell-specific or tissue-specific manner. Such specificity of expression may be achieved by operably linking one ore more of the DNA sequences encoding the fusion protein(s) to a cell-type specific transcription regulatory sequence (e.g. promoter/enhancer). Numerous cell-type specific transcription regulatory sequences are known. Others may be obtained from genes which are expressed in a cell-specific manner. See e.g. PCT/US95/10591, especially pp. 36–37.

For example, constructs for expressing the fusion proteins may contain regulatory sequences derived from known genes for specific expression in selected tissues. Representative examples are tabulated below:

| Tissue | Gene | Reference |
| --- | --- | --- |
| lens | g2-crystallin | Breitman, M. L., Clapoff, S., Rossant, J., Tsui, L. C., Golde, L. M., Maxwell, I. H., Bernstin, A. (1987) Genetic Ablation: targeted expression of a toxin gene causes microphthalmia in transgenic mice. Science 238: 1563–1565 |
| | aA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–1178<br>Kaur, S., key, B., Stock, J., McNeish, J. D., Akeson, R., Potter, S. S. (1989) Targeted ablation of alpha-crystallin-synthesizing cells produces lens-deficient eyes in transgenic mice. Development 105: 613–619 |
| pituitary-somatrophic cells | Growth hormone | Behringer, R. R., Mathews, L. S., Palmiter, R. D., Brinster, R. L. (1988) Dwarf mice produced by genetic ablation of growth hormone-expressing cells. Genes Dev. 2: 453–461 |
| pancreas | Insulin-Elastase-acinar cell specific | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603<br>Palmiter, R. D., Behringer, R. R., Quaife, C. J., Maxwell, F., Maxwell, I. H., Brinster, R. L. (1987) Cell lineage ablation in transgeneic mice by cell-specific expression of a toxin gene. Cell 50: 435–443 |
| T cells | lck promoter | Chaffin, K. E., Beals, C. R., Wilkie, T. M., Forbush, K. A., Simon, M. I., Perlmutter, R. M. (1990) EMBO Journal 9: 3821–3829 |
| B cells | Immunoglobulin kappa light chain | Borelli, E., Heyman, R., Hsi, M., Evans, R. M. (1988) Targeting of an inducible toxic phenotype in animal cells. Proc. Natl. Acad. Sci. USA 85: 7572–7576<br>Heyman, R. A., Borrelli, E., Lesley, J., Anderson, D., Richmond, D. D., Baird, S. M., Hyman, R., Evans, R. M. (1989) Thymidine kinase obliteration: creation of transgenic mice with controlled immunodeficiencies. Proc. Natl. Acad. Sci. USA 86: 2698–2702 |
| Schwann cells | $P_0$ promoter | Messing, A., Behringer, R. R., Hammang, J. P. Palmiter, R D, Brinster, R L, Lemke, G., P0 promoter directs espression of reporter and toxin genes to Schwann cells of transgenic mice. Neuron 8: 507–520 1992 |
| | Myelin basic protein | Miskimins, R. Knapp, L., Dewey, M J, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M. L., Rombola, H., Maxwell, I. H., Klintworth, G. K., Bernstein, A. (1990) Genetic ablation in transgenic mice with attenuated diphtheria toxin A gene. Mol. Cell. Biol. 10: 474–479 |
| lung | Lung surfacant gene | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603 |
| adipocyte P2 | | Ross, S. R., Braves, R A, Spiegelman, B M Targeted expression of a toxin gene to adipose tissue: transgenic mice resistant to obesity Genes and Dev 7: 1318–24 1993 |
| muscle | myosin light chain | Lee, K J, Ross, R S, Rockman, H A, Harris, A N, O'Brien, T X, van-Bilsen, M., Shubeita, H E, Kandolf, R., Brem, G., Prices et al J. BIol. Chem. Aug. 5, 1992, 267: 15875–85 |
| | Alpha actin | Muscat, G E., Perry, S., Prentice, H. Kedes, L. The human skeletal alpha-actin gene is regulated by a muscle-specific enhancer that binds three nuclear factors. Gene Expression 2, 111–26, 1992 |
| neurons | neurofilament proteins | Reeben, M. Halmekyto, M. Alhonen, L. Sinervirta, R. Saarma, M. Janne, J. Tissue-specific expression of rat light neurofilament promoter-driven reporter gene in transgenic mice. BBRC 1993: 192: 465–70 |
| liver | tyrosine aminotransferase, albumin, apolipoproteins | |

Target Genes

As used herein, the term "target gene" refers to a gene, whose transcription is stimulated according to the method of the invention. In one preferred embodiment, the gene is integrated in the chromosomal DNA of a cell. Alternatively, the gene is episomal. A cell comprising a target gene is referred to herein as a "target cell".

In a preferred embodiment of the invention, the target gene is an endogenous gene. As used herein, the term "endogenous gene" refers to a gene which is naturally present in a cell, in its natural environment, i.e., not a gene which has been introduced into the cell by genetic engineering. The endogenous gene can be any gene having a promoter that is recognized by at least one transcription factor. In a preferred embodiment, the promoter or any regulatory element thereof, of the endogenous gene ("endogenous promoter" and "endogenous regulatory element", respectively), is recognized by a known, preferably cloned, DNA binding protein, whether it is a transcription activator or repressor. Alternatively, if no DNA binding protein is known to interact with a target promoter, it is possible to clone such a factor using techniques well known in the art without undue experimentation, such as screening of expression libraries with at least a portion of the target promoter. Furthermore, the affinity of binding of a DNA binding domain to a target sequence can be improved according to methods known in the art. Such methods comprise, e.g., introducing mutations into the DNA binding domain and screening for mutants having increased DNA binding affinity.

In another embodiment of the invention, the target gene is an endogenous gene, which contains an exogenous target sequence. The exogenous target sequence can be inserted into the endogenous promoter or substitute at least a portion of the endogenous promoter. In preferred embodiments, the exogenous promoter or regulatory element introduced into the endogenous target promoter is recognized by a DNA binding protein, capable of binding with high affinity and specificity to a target sequence. In a preferred embodiment, the DNA binding protein is human. However, the DNA binding protein can be from any other species. For example, the DNA binding protein can be from the yeast GAL4 protein.

In yet another embodiment, the target gene is an exogenous gene. In a preferred embodiment, the exogenous gene is integrated into the chromosomal DNA of a cell. The exogenous gene can be inserted into the chromosomal DNA, or the exogenous gene can substitute for at least a portion of an endogenous gene. The target gene can be present in a single copy or in multiple copies. In view of the experimental results described herein, it is not necessary that the target gene be present in more than one copy. However, if even higher levels of protein encoded by the target gene is desired, multiple copies of the gene can be used.

In one embodiment, the taget gene construct enables transcription of a target gene to be regulated by a transcription factor in accordance with this invention comprises a DNA molecule which includes a synthetic transcription unit typically consisting of: (1) one copy or multiple copies of a DNA sequence recognized with high-affinity by the DNA binding domain of a fusion protein which includes a transcription activator, or of a protein which recruits the transcription activator; (2) a promoter sequence consisting minimally of a TATA box and initiator sequence but optionally including other transcription factor binding sites; (3) a coding sequence for a desired gene product, including sequences that promote the initiation and termination of translation, if appropriate; (4) an optional sequence consisting of a splice donor, splice acceptor, and intervening intron DNA; and (5) a sequence directing cleavage and polyadenylation of the resulting RNA transcript.

A wide variety of genes can be employed as the target gene, including genes that encode a therapeutic protein, antisense sequence or ribozyme of interest. The target gene can be any sequence of interest which provides a desired phenotype. It can encode a surface membrane protein, a secreted protein, a cytoplasmic protein, or there can be a plurality of target genes encoding different products. The target gene may be an antisense sequence which can modulate a particular pathway by inhibiting a transcription regulation protein or turn on a particular pathway by inhibiting the translation of an inhibitor of the pathway. The target gene can encode a ribozyme which may modulate a particular pathway by interfering, at the RNA level, with the expression of a relevant transcription regulator or with the expression of an inhibitor of a particular pathway. The proteins which are expressed, singly or in combination, can involve homing, cytotoxicity, proliferation, immune response, inflammatory response, clotting or dissolving of clots, hormonal regulation, etc. The proteins expressed may be naturally-occurring proteins, mutants of naturally-occurring proteins, unique sequences, or combinations thereof.

Various secreted products include hormones, such as insulin, human growth hormone, glucagon, pituitary releasing factor, ACTH, melanotropin, relaxin, etc.; growth factors, such as EGF, IGF-1, TGF-α or -β, PDGF, G-CSF, M-CSF, GM-CSF, FGF, erythropoietin, thrombopoietin, megakaryocytic stimulating and growth factors, etc.; interleukins, such as IL-1 to -13; TNF-α and -β, etc.; and enzymes and other factors, such as tissue plasminogen activator, members of the complement cascade, perforins, superoxide dismutase, coagulation factors, antithrombin-III, Factor VIIIc, Factor VIIIvW, Factor IX, a-antitrypsin, protein C, protein S, endorphins, dynorphin, bone morphogenetic protein, etc.

The gene can encode a naturally-occurring surface membrane protein or a protein made so by introduction of an appropriate signal peptide and transmembrane sequence. Various such proteins include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, B-cell receptor, TCR subunits α, β, γ, δ, CD10, CD19, CD28, CD33, CD38, CD41, etc., receptors, such as the interleukin receptors IL-2R, IL-4R, etc., channel proteins for influx or efflux of ions, e.g. Ca+2, K+, Na+, Cl− and the like; CFTR, tyrosine activation motif, zap-70, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the fusion proteins for exocytosis allows for rapid transfer of the proteins to the extracellular medium and a relatively high localized concentration.

Also, intracellular proteins can be of interest, such as proteins in metabolic pathways, regulatory proteins, steroid receptors, transcription factors, etc., depending upon the nature of the host cell. Some of the proteins indicated above can also serve as intracellular proteins.

By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cell keratinocytes, one could provide for protection against infection, by secreting, or -interferon, antichemotactic factors, proteases specific for bacterial cell wall proteins, etc.

In addition to providing for expression of a gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-selectin, GMP140, CLAM-1, etc., or addressing, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

For use in gene therapy, the target gene can encode any gene product that is beneficial to a subject. The gene product can be a secreted protein, a membraneous protein, or a cytoplasmic protein. Preferred secreted proteins include growth factors, differentiation factors, cytokines, interleukins, tPA, and erythropoietin. Preferred membraneous proteins include receptors, e.g, growth factor or cytokine receptors or proteins mediating apoptosis, e.g., Fas receptor. Other candidate therapeutic genes are disclosed in PCT/US93/01617.

In yet another embodiment, a "gene activation" construct which, by homologous recombination with a genomic DNA, alters the transcription regulatory sequences of an endogenous gene, can be used to introduce recognition elements for a DNA binding activity of one of the subject engineered proteins. A vareity of different formats for the gene activation constructs are available. See, for example, the Transkaryotic Therapies, Inc PCT publications WO93/09222, WO95/31560, WO96/29411, WO95/31560 and WO94/12650.

Design and Assembly of the DNA Constructs

Constructs may be designed in accordance with the principles, illustrative examples and materials and methods disclosed in the patent documents and scientific literature cited herein, each of which is incorporated herein by reference, with modifications and further exemplification as described herein. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector that directs the expression of the protein in the appropriate cell type(s). For biochemical analysis of the encoded fusion protein, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

Constructs encoding the fusion proteins and target genes of this invention can be introduced into the cells as one or more DNA molecules or constructs, in many cases in association with one or more markers to allow for selection of host cells which contain the construct(s). The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Viral delivery systems are discussed in greater detail below. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct(s). The cells will then be expanded and screened by virtue of a marker present in the constructs. Various markers which may be used successfully include hprt, neomycin resistance, thymidine kinase, hygromycin resistance, etc., and various cell surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, Cell (1987) 51, 503–512; Mansour, et al., Nature (1988) 336, 348–352; and Joyner, et al., Nature (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, and mammalian expression control elements, etc. which may be used to prepare stocks of construct DNAs and for carrying out transfections are well known in the art, and many are commercially available.

Delivery of Nucleic Acid: Ex Vivo and In Vivo

Any means for the introduction of heterologous nucleic acids into host cells, especially eucaryotic cells, an in particular animal cells, preferably human or non-human mammalian cells, may be adapted to the practice of this invention. For the purpose of this discussion, the various nucleic acid constructs described herein may together be referred to as the transgene. Ex vivo approaches for delivery of DNA include calcium phosphate precipitation, electroporation, lipofection and infection via viral vectors. Two general in vivo gene therapy approaches include (a) the delivery of "naked", lipid-complexed or liposome-formulated or otherwise formulated DNA and (b) the delivery of the heterologous nucleic acids via viral vectors. In the former approach, prior to formulation of DNA, e.g. with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal.

While various viral vectors may be used in the practice of this invention, retroviral, AAV, and adenovirus-based approaches are of particular interest. See, for example, Dubensky et al. (1984) Proc. Natl. Acad. Sci. USA 81, 7529–7533; Kaneda et al., (1989) Science 243, 375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. When using viral vectors, the recombinant nucleic acids may be delivered in a single virus, or may be divided into two or more viruses. For example, the fusion protein constructs could be delivered by one virus, while the target gene could be on a second virus. The target gene virus may further comprise an additional transcription regulatory domain construct. The following additional guidance on the choice and use of viral vectors may be helpful to the practitioner.

Viral Vectors:

Adenoviral Vectors

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), at the 3' and 5' terminal regions of the adenovirus genome which are cis elements necessary for viral DNA replication and packaging. See, e.g., Gingeras et al. (1982) J. Biol. Chem. 257: 13475–13491. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan (1990) Radiotherap. Oncol. 19:197). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviruses derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584).

Adenoviruses have also been used in vaccine development (Grunhaus and Horwitz (1992) Siminar in Virology 3:237; Graham and Prevec (1992) Biotechnology 20:363). Experiments in administering recombinant adenovirus to different tissues include trachea instillation (Rosenfeld et al. (1991); Rosenfeld et al. (1992) Cell 68:143), muscle injection (Ragot et al. (1993) Nature 361:647), peripheral intravenous injection (Herz and Gerard (1993) Proc. Natl. Acad. Sci. U.S.A. 90:2812), and stereotactic inoculation into the brain (Le Gal La Salle et al. (1993) Science 254:988).

Furthermore, the virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267).

The invention provides recombinant adenoviruses, pAdΔ, which have been deleted of adenovirus cis-elements necessary for replication and virion encapsidation and which contains a target gene and/or one or more genes encoding fusion proteins of the invention. Productive viral infection with pAdD requires a helper adenovirus, which alone or with a packaging cell line, supplies sufficient gene sequences necessary for a productive viral infection. Preferred helper viruses are altered in one or more native gene sequences which direct efficient packaging, to thereby produce a helper virus whose packaging function or ability to replicate is "crippled" or disabled. Such recombinant adenoviruses are further described in published PCT application No. PCT/US95/14017 having publication No. WO 96/13597 by Wilson et al.

Most replication-defective adenoviruses currently in use and favored by the present invention are deleted for all or parts of the viral E1 and E3 genes but may retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N. J., 1991) vol. 7. pp. 109–127). Accordingly, a preferred adenovirus of the invention is an adenovirus in which the E1 and E3 genes have been deleted or mutated, and in which the E1 gene has been replaced with a gene encoding a fusion protein and/or reporter gene of the invention. An E1/E3 deleted adenovirus allows for an insert of up to 8 kb. A preferred viral backbone is dl327 which is deleted in E1a, E1b, and E3. Deletion within adenovirus genes other than E1 and E3 region genes may also be useful to further reduce viral genome size, allowing thereby the insertion of larger genes of interest. In addition, since replication and viral protein expression in these viruses is reduced or eliminated in vivo, the immune response of the infected host to the virus and viral protein is also reduced. By decreasing the host immune response, the persistence of expression of the inserted gene is increased. Such vectors are further described in published PCT application No. PCT/US94/06338 having publication No. WO 94/28938 by Wilson and Engelhardt.

Other than the requirement that the adenovirus be replication defective, or at least conditionally defective, the nature of the adenovirus is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus for use in the method of the present invention. This is because Adenovirus type 5 is a human adenovirus about which a great deal of biochemical and genetic information is known, and it has historically been used for most constructions employing adenovirus. As stated above, the typical virus according to the present invention is replication defective and will not have an adenovirus E1 region. Thus, it will be most convenient to introduce the nucleic acid of interest at the position from which the E1 coding sequences have been removed. However, the position of insertion of the nucleic acid of interest in a region within the adenovirus sequences is not critical to the present invention. For example, the nucleic acid of interest may also be inserted in lieu of the deleted E3 region in E3 replacement viruses as described previously by Karlsson et. al. (1986) or in the E4 region where a helper cell line or helper virus complements the E4 defect.

Various adenoviruses have been shown to be of use in the transfer of genes to mammals, including humans. Replication-deficient adenovirus has been used to express marker proteins and CFTR in the pulmonary epithelium. Because of their ability to efficiently infect dividing cells, their tropism for the lung, and the relative ease of generation of high titer stocks, adenoviruses have been the subject of much research in the last few years, and various viruses have been used to deliver genes to the lungs of human subjects (Zabner et al., Cell 75:207–216, 1993; Crystal, et al., Nat Genet. 8:42–51, 1994; Boucher, et al., Hum Gene Ther 5:615–639, 1994). The first generation E1a deleted adenovirus has been improved upon with a second generation that includes a temperature-sensitive E2a viral protein, designed to express less viral protein and thereby make the virally infected cell less of a target for the immune system (Goldman et al., Human Gene Therapy 6:839–851, 1995). More recently, a viral vector deleted of all viral open reading frames has been reported (Fisher et al., Virology 217:11–22, 1996). Moreover, it has been shown that expression of viral IL-10 inhibits the immune response to adenoviral antigen (Qin et al., Human Gene Therapy 8:1365–1374, 1997).

Adenoviruses can also be cell type specific, i.e., infect only restricted types of cells and/or express a transgene only in restricted types of cells. For example, the viruses comprise a gene under the transcription control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

Techniques for introducing viruses into a variety of cells including hepatocytes, pancreatic and biliary eptithelial cells, endothelial cells and described in the following published PCT applications: PCT/US96/03041 (WO 96/26286) by Wilson et al. (hepatocytes); PCT/US91/09700 (WO 92/12242) by Mulligan and Wilson (hepatocytes); and PCT/US89/00422 (WO 89/07136) by Wilson and Mulligan (hepatocytes); PCT/US94/05187 (WO 94/26915) by J. M. Wilson (pancreatic cells); and PCT/US91/08127 (WO 92/07573) by Rafield et al. and PCT/US88/04383 (WO 89/05345) by Wilson and Mulligan (endothelial cells).

DNA sequences of a number of adenovirus types are available from Genbank. For example, human adenovirus type 5 has GenBank Accession No. M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenovirus and delivery protocol, by the same methods (restriction digest, linker ligation or filling in of ends, and ligation) used to insert the CFTR or other genes into the vectors.

In another embodiment, the invention provides a virus, e.g, adenovirus, which is a recombinant replication defective virus comprising the DNA of, or corresponding to, at least a portion of the genome of said virus, capable of infecting a mammalian cell, and a first expression sequence comprising a gene of interest operably linked to an expression control sequence, flanked on each side by the cis-acting terminal repeat sequence of a transposon, said expression sequence flanked by the DNA of the virus. The recombinant virus is capable of infecting a mammalian cell and capable of expressing the gene of interest and tansferring it to the chromatin of said cell in vivo or in vitro in the presence of a transposase. The virus can further comprise a gene encoding a suitable trans-acting transposase operably linked to an expression control sequence. Such a recombinant virus is capable of infecting a mammalian cell and capable of expressing the selected gene and transferring it to the chromatin of the infected cell in vivo or in vitro, when in the presence of a transposase. These viruses are further described in published PCT application No. WO 97/15679 by Kelley and Wilson.

The viruses of the invention can be administered to a host animal in such a manner that a potential immune reaction to the viruses is reduced. This can be achieved, e.g., by administering together with the virus a selected immune modulator, which substantially reduces the occurrence of neutralizing antibody responses directed against the virus encoded antigens and/or cytolytic T cell elimination of the viral protein containing cell. The immune modulator can be administered simultaneously or prior to administration of the viruses. The immune modulator can be, e.g., selected from the group consisting of a cytokine, an agent capable of depleting or inhibiting CD4+ T cells, and anti-T cell antibody, an agent capable of bloking the interaction between CD40 ligand on a T cell and CD40 on a B cell, an agent capable of bloking the interaction between the CD28 or CTLA4 ligand on a T cell and B7 on a B cell, and cyclphosphamide. This technique is further described in published PCT application No. WO 96/26285 by Wilson et al.

A preferred helper cell line is 293 (ATCC Accession No. CRL1573). This helper cell line, also termed a "packaging cell line" was developed by Frank Graham (Graham et al. (1987) J. Gen. Virol. 36:59–72 and Graham (1977) J. General Virology 68:937–940) and provides E1A and E1B in trans. However, helper cell lines may also be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

Adenovirus producer cell lines can include one or more of the adenoviral genes E1, E2a, and E4 DNA sequence, for packaging adenovirus in which one or more of these genes have been mutated or deleted are described, e.g., in WO 96/18418 by Kadan et al.; WO 95/346671 by Kovesdi et al.; WO94/28152 by Imler et al.; WO 95/02697 by Perrocaudet et al., WO96/14061 by Wang et al.

AAV

Yet another viral system useful for delivery of the subject fusion genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349–356; Samulski et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. By "adeno-associated virus inverted terminal repeats" or "AAV ITRs" is meant the palindromic regions which comprise the terminal repeats at the 3' and 5' ends of the AAV genome. The AAV ITR regions provide sequences for packaging the AAV provirus (i.e., the AAV genome) into the AAV viral capsid. The ITR regions also form secondary structures which act as self-primers for AAV replication. Samulski et al. (J. Virol. 63:3822, 1989), for example, describes AAV ITR sequences and structures. The nucleotide sequences of AAV ITR regions are known. See, e.g., Kotin, R. M. (1994) Human Gene Therapy 5:793–801; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when the rep gene is present in the cell (either on the same or on a different vector).

The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the recombinant DNA encoding the fusion protein(s), e.g. fusion proteins comprising an activation domain or DNA-binding domain, an AAV promoter can be used (ITR itself or AAV p5 (Flotte, et al. J. Biol. Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap (which are obligatory for replication and packaging of the recombinant viral construct) under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Typically, three days after transfection, recombinant AAV is harvested from the cells along with adenoviurs and the contaminating adenovirus is then inactivated by heat treatment.

Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Alternatively, a cell can be infected with a first AAV including a 5' ITR, a 3' ITR flanking a heterologous gene, and a second AAV vector which includes an inducible origin of replication, e.g., SV40 origin of replication, which is capable of being induced by an agent, such as the SV40 T antigen and which includes DNA sequences encoding the AAV rep and cap proteins. Upon induction by an agent, the second AAV vector may replicate to a high copy number, and thereby increased numbers of infectious AAV particles may be generated (see, e.g, U.S. Pat. No. 5,693,531 by Chiorini et al., issued Dec. 2, 1997. In yet another method for producing large amounts of recombinant AAV, a fusion plasmid is used which incorporate the Epstein Barr Nuclear Antigen (EBNA) gene, the latent origin of replication of Epstein Barr virus (orip) and an AAV genome. These plasmids are maintained as a multicopy extra-chromosomal elements in cells, such as in 293 cells. Upon addition of wild-type helper functions, these cells will produce high amounts of recombinant AAV (U.S. Pat. No. 5,691,176 by Lebkowski et al., issued Nov. 25, 1997). In another system, an AAV packaging plasmid is provided that allows expression of the rep gene, wherein the p5 promoter, which normally controls rep expression, is replaced with a heterologous promoter (U.S. Pat. No. 5,658,776, by Flotte et al., issued Aug. 19, 1997). Additionally, one may increase the efficiency of AAV transduction by treating the cells with an agent that facilitates the conversion of the single stranded form to the double stranded form, as described in Wilson et al., WO96/39530.

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV expression in vivo (Flotte, et al. J. Biol. Chem. 268:3781–3790, 1993) or chromatographic purification, as described in O'Riordan et al., WO97/08298.

Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

For additional detailed guidance on AAV technology which may be useful in the practice of the subject invention, including methods and materials for the incorporation of a transgene, the propagation and purification of the recombinant AAV containing the transgene, and its use in transfecting cells and mammals, see e.g. Carter et al, U.S. Pat. No. 4,797,368 (10 Jan. 1989); Muzyczka et al, U.S. Pat. No. 5,139,941 (18 Aug. 1992); Lebkowski et al, U.S. Pat. No. 5,173,414 (22 Dec. 1992); Srivastava, U.S. Pat. No. 5,252,479 (12 Oct. 1993); Lebkowski et al, U.S. Pat. No. 5,354,678 (11 Oct. 1994); Shenk et al, U.S. Pat. No. 5,436,146 (25 Jul. 1995); Chatterjee et al, U.S. Pat. No. 5,454,935 (12 Dec. 1995), Carter et al WO 93/24641 (published 9 Dec. 1993), and Natsoulis, U.S. Pat. No. 5,622,856 (Apr. 22, 1997). Further information regarding AAVs and the adenovirus or herpes helper functions required can be found in the following articles. Berns and Bohensky (1987), "Adeno-Associated Viruses: An Update", Advanced in Virus Research, Academic Press, 33:243–306. The genome of AAV is described in Laughlin et al. (1983) "Cloning of infectious adeno-associated virus genomes in bacterial plasmids", Gene, 23: 65–73. Expression of AAV is described in Beaton et al. (1989) "Expression from the Adeno-associated virus p5 and p19 promoters is negatively regulated in trans by the rep protein", J. Virol., 63:4450–4454. Construction of rAAV is described in a number of publications: Tratschin et al. (1984) "Adeno-associated virus vector for high frequency integration, expression and rescue of genes in mammalian cells", Mol. Cell. Biol., 4:2072–2081; Hermonat and Muzyczka (1984) "Use of adeno-associated virus as a mammalian DNA cloning vector: Transduction of neomycin resistance into mammalian tissue culture cells", Proc. Natl. Acad. Sci. USA, 81:6466–6470; McLaughlin et al. (1988) "Adeno-associated virus general transduction vectors: Analysis of Proviral Structures", J. Virol., 62:1963–1973; and Samulski et al. (1989) "Helper-free stocks of recombinant adeno-associated viruses: normal integration does not require viral gene expression", J. Virol., 63:3822–3828. Cell lines that can be infected by rAAV are those described in Lebkowski et al. (1988) "Adeno-associated virus: a vector system for efficient introduction and integration of DNA into a variety of mammalian cell types", Mol. Cell. Biol., 8:3988–3996. "Producer" or "packaging" cell lines used in manufacturing recombinant retroviruses are described in Dougherty et al. (1989) J. Virol., 63:3209–3212; and Markowitz et al. (1988) J. Virol., 62:1120–1124.

Hybrid Adenovirus-AAV

Hybrid Adenovirus-AAV is represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid virus is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in the this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0–1) and includes the 5' ITR and the packaging/enhancer domain. The 3' adenovirus sequences of the hybrid virus include the right terminal 3' ITR sequence which is about 580 nucleotides (about bp 35,353—end of the adenovirus, referred to as about map units 98.4–100.

The AAV sequences useful in the hybrid vector are viral sequences from which the rep and cap polypeptide encoding sequences are deleted and are usually the cis acting 5' and 3' ITR sequences. Thus, the AAV ITR sequences are flanked by the selected adenovirus sequences and the AAV ITR sequences themselves flank a selected transgene. The preparation of the hybrid vector is further described in detail in published PCT application entitled "Hybrid Adenovirus-AAV Virus and Method of Use Thereof", WO 96/13598 by Wilson et al.

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

Retroviruses

The retroviruses are a group of single-stranded RNA viruses characterized by an ability to convert their RNA to double-stranded DNA in infected cells by a process of reverse-transcription (Coffin (1990) Retroviridae and their Replication" In Fields, Knipe ed. Virology. New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol and env that code for capsial proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viruses, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham: Butterworth; Temin, (1986) "Retrovirus Vectors for Gene Transfer: Efficient Integration into and Exprssion of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviruses are able to infect a broad variety of cell types. However, integration and stable expression require the division of host cells (Paskind et al. (1975) Virology 67:242).

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181:307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150: 4104–4115; U.S. Pat. No. 4,868,116; U.S. Pat. No. 4,980, 286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the virus (see, for example PCT publications WO93/25234, WO94/06920, and WO94/11524). For instance, strategies for the modification of the infection spectrum of retroviruses include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem. 266:14143–14146). Coupling can be in the form of the chemical cross-linking with a protein or other variety (e.g. lactose to convert the env protein to an asialoglyco-protein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Other Viral Systems

Other viral systems that may have application in gene therapy have been derived from herpes virus, e.g., Herpes Simplex Virus (U.S. Pat. No. 5,631,236 by Woo et al., issued May 20, 1997), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth, Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1–10), and several RNA viruses. Preferred viruses include an alphavirus, a poxivirus, an arena virus, a vaccinia virus, a polio virus, and the like. In particular, herpes virus may provide a unique strategy for persistence of the recombinant gene in cells of the central nervous system and ocular tissue (Pepose et al., (1994) Invest Ophthalmol Vis Sci 35:2662–2666). They offer several attractive features for various mammalian cells (Friedmann (1989) Science, 244:1275–1281; Ridgeway, 1988, supra; Baichwal and Sugden, 1986, supra; Coupar et al., 1988; Horwich et al. (1990) J. Virol., 64:642–650).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, supra). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al. (1991) Hepatology, 14:124A).

Administration of Viral Vectors

Generally the viral particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles. Delivery of the recombinant viral vector can be carried out via any of several routes of administration, including intramuscular injection, intravenous administration, subcutaneous injection, intrahepatic administration, catheterization (including cardiac catheterization), intracranial injection, nebulization/inhalation or by instillation via bronchoscopy.

Preferably, the DNA or recombinant virus is administered in sufficient amounts to transfect cells within the recipient's target cells, including without limitation, muscle cells, liver cells, various airway epithelial cells and smooth muscle cells, neurons, cardiac muscle cells, etc. and provide sufficient levels of transgene expression to provide for observable ligand-responsive secretion of a target protein, preferably at a level providing therapeutic benefit without undue adverse effects.

Optimal dosages of DNA or virus depends on a variety of factors, as discussed previously, and may thus vary somewhat from patient to patient. Again, therapeutically effective doses of viruses are considered to be in the range of about 20 to about 50 ml of saline solution containing concentrations of from about $1\times10^7$ to about $1\times10^{10}$ pfu of virus/ml, e.g. from $1\times10^8$ to $1\times10^9$ pfu of virus/ml.

Host Cells

This invention is particularly useful for the engineering of animal cells and in applications involving the use of such engineered animal cells. The animal cells may be insect, worm or mammalian cells. While various mammalian cells may be used, including, by way of example, equine, bovine, ovine, canine, feline, murine, and non-human primate cells, human cells are of particular interest. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Of particular interest are hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells The cells may be autologous cells, syngeneic cells, allogeneic cells and even in some cases, xenogeneic cells with respect to an intended host organism. The cells may be modified by changing the major histocompatibility complex ("MHC") profile, by inactivating β2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

In some instances specific clones or oligoclonal cells may be of interest, where the cells have a particular specificity, such as T cells and B cells having a specific antigen specificity or homing target site specificity.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about 104 and not more than about 109 and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10): 1213–24 (HepG2 cells/hydroxyethyl methacrylate-methyl methacrylate membranes); Chang et al, 1993, Hum Gene Ther 4(4):433–40 (mouse Ltk-cells expressing hGH/immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more fusion proteins containing component domains derived from proteins of the host species and/or from viral proteins or proteins from species other than the host species. For example in such cases the fusion proteins may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as adenovirus, adeno-associated virus, and retroviruses, as discussed above, which allow for transfection and, in some cases, integration of the virus into the host. See, for example, Dubensky et al. (1984) Proc. Natl. Acad. Sci. USA 81, 7529–7533; Kaneda et al., (1989) Science 243, 375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcription initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

Binding Properties, Assays

FK506 is known to bind to the human protein, FKBP12 and to form a tripartite complex with the serine/threonine phosphatase, calcineurin. FK506 analogs may be characterized and compared to FK506 with respect to their ability to bind to human FKBP12 and/or to form tripartite complexes with fusion proteins containing human FKBP12 and CABs. See, for example, WO 96/41865 (Clackson et al). That application discloses various materials and methods which can be used to quantify the ability of a compound to bind to human FKBP12 or to form a tripartite complex with (i.e., "heterodimerize") proteins comprising human FKBP12 and the FRB domain of human FRAP, respectively. Such assays include fluorescence polarization assays to measure binding. Also included are cell based transcription assays in which the ability of a compound to form the tripartite complex is measured indirectly by correlation with the observed level of reporter gene product produced by engineered mammalian cells in the presence of the compound. Corresponding cell-based assays may also be conducted in engineered yeast cells. See e.g. WO 95/33052 (Berlin et al).

It will often be preferred that the ligands of this invention be physiologically acceptable (i.e., lack undue toxicity toward the cell or organism with which it is to be used), can be taken orally by animals (i.e., is orally active in applications in whole animals, including gene therapy), and/or can cross cellular and other membranes, as necessary for a particular application.

In addition, preferred ligands are those which bind preferentially to mutant immunophilins (by way of non-limiting example, a human FKBP in which Phe36 is replaced with a different amino acid, preferably an amino acid with a less bulky R group such as valine or alanine) over native or naturally-ocurring immunophilins. For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12, as determined by any scientifically valid or art-accepted assay methodology.

Binding affinities of various ligands of this invention with respect to human FKBP12, variants thereof or other immunophilin proteins may be determined by adaptation of known methods used in the case of FKBP. For instance, the practitioner may measure the ability of a compound of this invention to compete with the binding of a known ligand to the protein of interest. See e.g. Sierkierka et al, 1989, Nature 341, 755–757 (test compound competes with binding of labeled FK506 derivative to FKBP).

One set of preferred ligands of this invention which binds, to human FKBP12, to a mutant thereof as discussed above, or to a fusion protein containing such FKBP domains, with a Kd value below about 200 nM, more preferably below about 50 nM, even more preferably below about 10 nM, and even more preferably below about 1 nM, as measured by direct binding measurement (e.g. fluorescence quenching), competition binding measurement (e.g. versus FK506), inhibition of FKBP enzyme activity (rotamase), or other assay methodology. In one subset of such compounds, the FKBP domain is one in which phenylalanine at position 36 has been replaced with an amino acid having a less bulky side chain, e.g. alanine, valine, methionine or serine.

A Competitive Binding FP Assay is described in detail in the examples which follow. That assay permits the in vitro measurement of an IC50 value for a given compound which reflects its ability to bind to an FKBP protein in competition with a labeled FKBP ligand, such as, for example, FK506.

One preferred class of compounds of this invention are those ligands which have an IC50 value in the Competitive Binding FP Assay better than 1000 nM, preferably better than 300 nM, more preferably better than 100 nM, and even more preferably better than 10 nM with respect to a given FKBP domain and ligand pair, e.g. human FKBP12 or a variant thereof with up to 10, preferably up to 5 amino acid replacements, with a flouresceinated FK506 standard. In one subset of that class, the FKBP domain has one of the abovementioned modifications at position 36.

The ability of the ligands to multimerize fusion proteins may be measured in cell-based assays by measuring the occurrence of an event triggered by such multimerization. For instance, one may use cells containing and capable of expressing DNA encoding a first fusion protein comprising one or more FKBP-domains and one or more action domains as well as DNA encoding a second fusion protein containing an CAB domain and one or more action domains capable, upon multimerization, of actuating a biological response. We prefer to use cells which further contain a reporter gene under the transcription control of a regulatory element (i.e., promoter) which is responsive to the multimerization of the fusion proteins. The design and preparation of illustrative components and their use in so engineered cells is described in WO96/41865 and the other international patent applications referred to in this and the foregoing section. The cells are grown or maintained in culture. A ligand is added to the culture medium and after a suitable incubation period (to permit gene expression and secretion, e.g. several hours or overnight) the presence of the reporter gene product is measured. Positive results, i.e., multimerization, correlates with transcription of the reporter gene as observed by the appearance of the reporter gene product. The reporter gene product may be a conveniently detectable protein (e.g. by ELISA) or may catalyze the production of a conveniently detectable product (e.g. colored). Materials and methods for producing appropriate cell lines for conducting such assays are disclosed in the international patent applications cited above in this section. Typically used target genes include by way of example SEAP, hGH, beta-galactosidase, Green Fluorescent Protein and luciferase, for which convenient assays are commercially available.

Another preferred class of compounds of this invention are those which are capable of inducing a detectable signal in a 2-hybrid transcription assay based on fusion proteins containing an FKBP domain. Preferably, the FKBP domain is an FKBP domain other than wild-type human FKBP12.

Another assay for measuring the ability of the ligands to multimerize fusion proteins, like the FKBP-based transcription assay, is a cell-based assay which measures the occurrence of an event triggered by such multimerization. In this case, one uses cells which constitutively express a detectable product. The cells also contain and are capable of expressing DNAs encoding fusion proteins comprising one or more immunophilin-derived ligand binding domains and one or more action domains, such as the intracellular domain of FAS, capable, upon multimerization, of triggering cell death. The design and preparation of illustrative components and their use in so engineering cells is described in WO95/02684. See also WO96/41865. The cells are maintained or cultured in a culture medium permitting cell growth or continued viability. The cells or medium are assayed for the presence of the constitutive cellular product, and a baseline level of reporter is thus established. One may use cells engineered for constitutive production of hGH or any other conveniently detectable product to serve as the reporter. The compound to be tested is added to the medium, the cells are incubated, and the cell lysate or medium is tested for the presence of reporter at one or more time points. Decrease in reporter production indicates cell death, an indirect measure of multimerization of the fusion proteins.

Another preferred class of compounds of this invention are those which are capable of inducing a detectable signal in such an FKBP/CAB-based apoptosis assay. Preferably, the FKBP domain is an FKBP domain other than wild-type human FKBP12. In some cases, the FKBP domain is modified, as discussed above. Also preferably, the CAB domain is a CAB domain other than wild-type CAB.

Conducting such assays permits the practitioner to select ligands possessing the desired IC50 values and/or binding preference for a mutant FKBP over wild-type human FKBP12. The Competitive Binding FP Assay permits one to select monomers or ligands which possess the desired IC50 values and/or binding preference for a mutant FKBP or wild-type FKBP relative to a control, such as FK506.

Applications

The ligands and ligand binding domains can be used as described in WO94/18317, WO95/02684, WO96/20951, WO95/41865, e.g. to regulatably activate the transcription of a desired gene, delete a target gene, actuate apoptosis, or trigger other biological events in engineered cells growing in culture or in whole organisms, including in gene therapy applications. The following are non-limiting examples of applications of the subject invention.

1. Regulated gene therapy. In many instances, the ability to switch a therapeutic gene on and off at will or the ability to titrate expression with precision are important for therapeutic efficacy. This invention is particularly well suited for achieving regulated expression of a therapeutic target gene in the context of human gene therapy. One example uses a pair of fusion proteins of this invention (one containing at least one CAB domain, the other containing at least one FKBP domain), a ligand capable of dimerizing the fusion proteins, and a target gene construct to be expressed. One of the fusion proteins comprises a DNA-binding domain, preferably a composite DNA-binding domain as described in Pomerantz et al, supra, as the heterologous action domain. The second fusion protein comprises a transcription activating domain as the heterologous action domain. The improved ligand is capable of binding to both fusion proteins and thus of effectively cross-linking the fusion proteins. DNA molecules encoding and capable of directing the expression of these fusion proteins are introduced into the cells to be engineered. Also introduced into the cells is a target gene linked to a DNA sequence to which the DNA-binding domain is capable of binding. Contacting the engineered cells or their progeny with the improved ligand (by administering it to the animal or patient) leads to assembly of the transcription factor complex and hence to expression of the target gene. The design and use of similar components is disclosed in PCT/US93/01617 and in WO 96/41865 (Clackson et al). In practice, the level of target gene expression should be a function of the number or concentration of fusion transcription factor complexes, which should in turn be a function of the concentration of the improved ligand. Dose (of improved ligand)-responsive gene expression is typically observed.

The improved ligand may be administered to the patient as desired to activate transcription of the target gene. Depending upon the binding affinity of the improved ligand, the response desired, the manner of administration, the biological half-life of the ligand and/or target gene mRNA, the number of engineered cells present, various protocols may be employed. The improved ligand may be administered by various routes, including parenterally or orally. The number of administrations will depend upon the factors described above. The improved ligand may be taken orally as a pill, powder, or dispersion; bucally; sublingually; injected intravascularly, intraperitoneally, intramuscularly, subcutaneously; by inhalation, or the like. The improved ligand (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcription activation by the improved ligand is to be reversed or terminated, a monomeric compound which can compete with the improved ligand may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcription silencer) with a ligand binding domain. In another approach, cells may be eliminated through apoptosis via signalling through Fas or TNF receptor as described elsewhere. See International Patent Applications PCT/US94/01617 and PCT/US94/08008.

The particular dosage of the improved ligand for any application may be determined in accordance with the procedures used for therapeutic dosage monitoring, where maintenance of a particular level of expression is desired over an extended period of times, for example, greater than about two weeks, or where there is repetitive therapy, with individual or repeated doses of improved ligand over short periods of time, with extended intervals, for example, two weeks or more. A dose of the improved ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the improved ligand is chronically administered, once the maintenance dosage of the improved ligand is determined, one could then do assays at extended intervals to be assured that the cellular system is providing the appropriate response and level of the expression product.

It should be appreciated that the system is subject to many variables, such as the cellular response to the improved ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like.

2. Production of recombinant proteins and viruses. Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant AAV viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

3. Biological research. This invention is applicable to a wide range of biological experiments in which precise control over a target gene is desired. These include: (1) expression of a protein or RNA of interest for biochemical purification; (2) regulated expression of a protein or RNA of interest in tissue culture cells (or in vivo, via engineered cells) for the purposes of evaluating its biological function; (3) regulated expression of a protein or RNA of interest in transgenic animals for the purposes of evaluating its biological function; (4) regulating the expression of a gene encoding another regulatory protein, ribozyme or antisense molecule that acts on an endogenous gene for the purposes of evaluating the biological function of that gene. Transgenic animal models and other applications in which the components of this invention may be adapted include those disclosed in PCT/US95/10591.

This invention further provides kits useful for the foregoing applications. Such kits contain DNA constructs encoding and capable of directing the expression of fusion proteins of this invention (and may contain additional domains as discussed above) and, in embodiments involving regulated gene transcription, a target gene construct containing a target gene linked to one or more transcriptional control elements which are activated by the multimerization of the fusion proteins. Alternatively, the target gene construct may contain a cloning site for insertion of a desired target gene by the practitioner. Such kits may also contain a sample of a dimerizing agent capable of dimerizing the two recombinant proteins and activating transcription of the target gene.

Formulations, Dosage and Administration

By virtue of its capacity to promote protein—protein interactions, a ligand of this invention may be used in pharmaceutical compositions and methods for promoting formation of complexes of fusion proteins of this invention in a human or non-human mammal containing genetically engineered cells of this invention.

The preferred method of such treatment or prevention is by administering to the mammal an effective amount of the compound to promote measurable formation of such complexes in the engineered cells, or preferably, to promote measurable actuation of the desired biological event triggered by such complexation, e.g. transcription of a target gene, apoptosis of engineered cells, etc.

Therapeutic/Prophylactic Administration & Pharmaceutical Compositions

The ligands can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and one or more pharmaceutically acceptable carriers and/or other excipients. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2- propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the multimerizer may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the multimerizer, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The invention also provides a pharmaceutical pack or kit comprising one or more containers containing one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The notice or package insert may contain instructions for use of an improved ligand of this invention, consistent with the disclsoure herein.

EXAMPLES

Example 1

Construction of Human Cab Fusion Proteins

All constructs were made in the pcDNA3/m.jy2 vector which was derived from the pcDNA3 vector by mutation of backbone SalI sites and insertion of a new polylinker region. (B. Stockwell, J. Yang). The plasmid contains an ampicillin resistance gene which allows for selection in *E. coli* and a cytomegalovirus promoter which allows for high plasmid gene expression. The pcDNA3/m.jy2 plasmid was chosen instead of PBJ5, a plasmid used in many of the other dimerization systems, because its restriction digest profile eased the cloning of the calcineurin constructs.

Polymerase Chain Reaction

Primers were designed for the 3' and 5' ends of all calcineurin constructs used in this project. The primers integrated specific restriction sites into the ends of each gene to facilitate ligation of the gene into the pcDNA3/m.jy2 vector. The primers were synthesized on a Perkin Elmer Applied Biosystems 394 DNA/RNA Synthesizer Machine and purified using a Perkin Elmer Purification Protocol.

PCR Reactions were carried out on an M5 Research Mini-Cycler. The general PCR protocol included incubation at 95βC for 5 minutes. 30 seconds were then allowed for annealing at 55βC. This was followed by extension for one minute at 72βC and then a one minute incubation at 95βC. The annealing, extension and incubation steps were repeated 25–30 times. The resulting reaction mixture was stored at 4βC until further work up. PCR products were purified using a Qiagen PCR Purification Kit and the protocol therein.

Oligos for Construction of Calcineurin A Fragments:

CNA sequence is in bold hCNA 5' PCR Oligo Start at residue 12

```
         Junk       XhoI
5' cggg ccc ccc ctc gag tct acg acc gac agg gtg gtg aaa gc 3' (SEQ ID NO 4)
Note:
g -> t is a silent mutation that destroys the SalI site.
``` hCNA 5' PCR Oligo Start at residue 340

```
          Junk      XhoI
5' atat aaa tcg ctc gag cca tac tgg ctt cca aat ttc atg g 3' (SEQ ID NO 5)
``` hCNA 5' PCR Oligo Start at Reisude 350

```
          Junk     XhoI
5' atat aaa tcg ctc gag ttt act tgg tcc ctt cca ttt gtt ggg g 3' (SEQ ID NO 6)
``` hCNA 3' PCR Oligo End at Residue 370

```
         Junk    See Note    ApaI    Junk     SalI
5' Cca gta ggg tct aga tct ggg ccc acg ata taa gtc gac gtt gag gac
att tac cag C 3' (SEQ ID NO 7)
Note:
tct aga tct = overlapping XbaI and BglII sites. (SEQ ID NO 8)
``` hCNA 3' PCR Oligo End at Residue 394

```
         See Note  STP       FLAG Peptide          SalI
5' ttaa tct aga tct tca ctt gtc atc gtc atc ttt ata gtc gac ctc
ttt ccg ggc tgc agc tg 3' (SEQ ID NO 9)
Note:
tct aga tct = overlapping XbaI and BglII sites. (SEQ ID NO 8)
```

Oligos Designed for Human Calcineurin B:

(Bold portion is CNB sequence)

hCNB 5' PCR Oligo Start at residue 2

```
      Junk      XhoI
5' atat aaa tcg ctc gag gga aat gag gca agt tat cct ttg g 3'  (SEQ ID NO 10)
``` hCNB 5' PCR Oligo Start at residue 3

```
      Junk      XhoI
5' atat aaa tcg ctc gag aat gag gca agt tat cct ttg g 3'
(SEQ ID NO 11)
``` hCNB 3' PCR Oligo with 3' FLAG peptide and Stop

```
         See Note     ApaI  STP         FLAGPeptide
5' ttaa tct aga tct ggg ccc tca ctt gtc atc gtc atc ttt ata
 SalI
gtc gac cac atc tac cac cat c 3'
(SEQ ID NO 12)
Note:
tct aga tct = overlapping XbaI and BglII sites. (SEQ ID NO 8)
```

Oligos Designed for Constructing CNA-CNB Linkers:

(Bold portion is CNA sequence)

3' PCR Primer for hCNA to Generate 24 Amino Acid Template Linker (to residue 370)

```
      Junk      ApaI   See Note          Linker
5' cga ttt atat ggg ccc tct aga tct aga acc aga acc aga acc aga
                     Linker
acc aga acc aga acc aga acc aga acc aga acc aga acc
acc gtt gag gac att tac cag c 3'
(SEQ ID NO 13)
Note:
tct aga tct = overlapping XbaI and BglII sites. (SEQ ID NO 8)
```

3' PCR Primer for Randomizing the Length of the CNA-CNB Linker (Register 1 oligo)

```
      Junk      See Note   ApaI      Junk        SalI
5' g aat cgc aaa tct aga tct ggg ccc gtc atc ttt ata gtc gac acc
aga acc aga acc 3'
(SEQ ID NO 14)
Note:
tct aga tct = overlapping XbaI and BglII sites. (SEQ ID NO 8)
```

3' PCR Primer for Randomizing the Length of the CNA-CNB Linker (Register 2 oligo)

```
      Junk      See Note   ApaI      Junk        SalI
5' g aat cgc aaa tct aga tct ggg ccc gtc atc ttt ata gtc gac aga
acc aga acc aga 3'
(SEQ ID NO 15)
Note:
tct aga tct = overlapping XbaI and BglII sites. (SEQ ID NO 8)
```

PCR Conditions (for all CNA and CNB Fragments):

| Step | Temperature (° C.) | Time (sec) |
|---|---|---|
| 1. | 95 | 180 |
| 2. | 37 | 30 |
| 3. | 72 | 60 |
| 4. | 95 | 60 |
| 5. | 37 | 30 |
| 6. | 72 | 60 |
| 7. | Goto Step 4 9 times | |
| 8. | 95 | 60 |
| 9. | 55 | 30 |
| 10. | 72 | 60 |
| 11. | Goto Step 8 25 times | |
| 12. | 72 | 300 |
| 13. | 4 | |

PCR Conditions (for Randomization of Linker Length):

| Step | Temperature (° C.) | Time (sec) |
|---|---|---|
| 1. | 95 | 180 |
| 2. | 37 | 30 |
| 3. | 72 | 60 |
| 4. | 95 | 60 |
| 5. | 45 | 30 |
| 6. | 72 | 60 |
| 7. | Goto Step 4 9 times | |
| 8. | 95 | 60 |
| 9. | 55 | 30 |
| 10. | 72 | 60 |
| 11. | Goto step 8 25 times | |
| 12. | 72 | 300 |
| 13. | 4 | |

Example 2

Method of Linking Calcineurin A to Calcineurin B

The method of linking calcineurin A to calcineurin B in the CABS falls into two categories. The first method used fragements of the gene encoding calcineurin A (residues 12–370, 12–394, 340–370, 340–394, 350–370, or 350–394) generated by PCR to contain a 5' Xho1 restriction site directly before the codons for residues 12, 340, or 350 and a 3' Sal1 restriction site directly following the codons for residues 370 or 394. The fragments of the gene encoding calcineurin B (residues 2–170 or 3–170) were also generated by PCR to contain a 5' Xho1 restriction site directly before the codons for residues 2 or 3 and a 3' Sal1 restriction site directly following the codon for residue 170. Ligation of the two fragments were performed such that the fragment of calcineurin A is 5' to calcineurin B and the site of ligation is the result of a Sal1/Xho1 fusion (gtcgag). This results in two additional codons encoding a Valine and a Glutamate between the calcineurin A portion of the CABS and the calcineurin B portion of these CABS.

The second method of linking the CABS was to generate a pool of calcineurin A fragments with linkers, ranging in size from 6 to 24 amino acids, attached directly after residue 370. These fragments were PCR'ed such that they also contained a 5' Xho1 restriction site directly before the codons for residues 12, 340, 350 and a 3' Sal1 restriction site directly following the codons encoding the flexible linker. The calcineurin B fragments were the same as those described in the previous paragraph. The ligation was performed such that the fragment of calcineurin A is 5' to calcineurin B and the site of ligation is the result of a Sal1/Xho1 fusion (gtcgag). This results in two additional codons encoding a Valine and a Glutamate between the calcineurin A-linker portion of the CABS and the calcineurin B portion of these CABS.

Generation of the variously lengthed flexible linkers on calcineurin A was accomplished through a two step PCR procedure developed for this purpose. The following bases were added after the codon for residue 370 of calcineurin A by PCR:

CNA residue 370—

```
GGTGGTTCTGGTTCTGGTGGTTCTGGTTCTGGTTCTGGTTCTGG
TTCTGGTTCTGGTTCTGGTTCTGGTTCT (SEQ ID NO 16)
```

This encodes for the following flexible longest length linker:

GGSSGSGGSGSGSGSGSGSG            (SEQ ID NO 17)

PCR was then performed on the above template with two primers that contained the following complimentary sequence:

```
Primer 1:
5' GTC GAC AGA ACC AGA ACC AGA 3'    (SEQ ID NO 18)

Primer 2:
5' GTC GAC ACC AGA ACC AGA ACC 3'    (SEQ ID NO 19)
``` and a Sal 1 restriction site (gtc gac) (SEQ ID NO 20). Upon PCR with both primers that can anneal in many registers of the template calcineurin A, fragments of calcineurin A containing from 7 to 24 amino acids of the flexible linker were generated. Interestingly, all of the fragments contained the amino acids GGSGS (SEQ ID NO 21) followed by the appropriate number of single alternating Glycines and Serines. The predicted PCR products should have two GGSGS (SEQ ID NO 21) repeats, but we recovered only one in all of the clones. Moreover, this strategy also provided fragments that had longer linkers than what we had predicted because the second PCR step allows the linker to grow.

Example 3

Construction of FKBP and CAB Fusion Proteins

All CNA constructs were derived from human calcineurin A (α isoform). All CNB constructs were derived from human calcineurin B. $CNB_M$ contains an N-terminal methionine, while $CNB_{MG}$ contains both a methionine and a glycine residue. Residues 1–147 from GAL4 are used for the GAL4 DNA binding domain (GE). Residues 413–490 from VP16 are used as the VP16 transactivation domain (VE). Each VE construct contains an N-terminal nuclear localization sequence (NLS) from SV40 large T antigen, while all GE constructs contain an NLS within the GAL4 sequence. All GE constructs contain a FLAG epitope tag and all VE constructs contain a FLU epitope tag. All FKBP constructs contain the entirety of the human coding sequence. The FRB construct contains residues 2025–2114 of the human FRAP protein. The UAS-SEAP reporter gene contains 5 upstream Gal4-binding sites (UAS sites) and a minimal interleukin 2 basic promoter and encodes SEcreted Alkaline Phosphatase, a heat-stable alkaline phosphatase.

The same basic digestion, ligation and transformation procedure was used to obtain each construct. Calcineurin A fragments were put into the pcDNA3/m.jy2 vector by digesting the PCR product with XhoI and XbaI and ligating into vector that had been cut with the same enzymes. CNB was ligated into the vector using XhoI and ApaI restriction sites. FKBP3-VE and FKBP3-GE were ligated from PBJ5 into the pcDNA3/m.jy2 vector using the SacII and EcoRI enzymes. These basic parent vectors allowed for the generation of all future constructs since calcineurin A and calcineurin B fragments could be liberated by digestion with XhoI and SalI or XhoI and ApaI while VE could be liberated with SalI and ApaI. In addition, GE, CNA or CNB containing vectors could be created by digestion with SalI and ApaI. Since XhoI and SalI generate complementary sticky ends, all the calcineurin constructs used in this project could be created from different combinations of the digests described above and from digests of successive generations of constructs.

After vector and insert DNAs were digested with the appropriate restriction enzymes, the products were then run on either a 1% or 2% agarose gel (1% was used for all products greater than 300 basepairs). The desired DNA bands were then isolated using a Qiagen Gel Purification Kit and the protocol therein. Vector and insert bands were ligated from 4 hours to overnight at 16βC in an 11 ml volume with 1 ml T4 DNA ligase and 1 ml NEB ligation buffer and a 2:1 (or greater) ratio of insert to vector. The ligation reaction was then transformed into subcloning efficiency DH5a bacterial cells obtained from GIBCO BRL according to the protocol supplied with the cells. For certain inefficient ligations, such as SalI/ApaI ligations, maximum efficiency DH5a cells were used. Positive transformants were selected for using ampicillin. A few positive colonies from each ligation were chosen for further analysis. The Wizard Mini-Prep Kit and protocol therein were used to isolate plasmid DNA from these positive colonies. The DNA was subjected to restriction digest analysis to screen for false positive clones. DNA from true positive colonies was prepared using a Wizard Midi-Prep Kit and protocol therein. The prepared DNA was quantitated using the relation:

[double stranded DNA]=(50 mg/ml)*(A260)

where A260 equals the absorbance of the DNA sample at 260 nm wavelength light.

Example 4

Reporter-Based Assay for Activation of Transcription

The transcription assay that we utilize has been described in WO94/18317 and in Rivera et al., 1996 supra. The general assay is as follows.

10 million T-antigen transformed Jurkat T-cells growing in log phase at 37 degrees with 5% $CO_2$ in RPMI medium supplemented with 10% FBS, Penicillin and Streptomycin, and Glutamate are centrifuged for 5 minutes at 1000×g. This pellet is washed with RPMI without phenol-red and re-pelleted by centrifugation at 1000×g for 5 minutes. 200 microliters of phenol-free RPMI are used to resuspend each 10 million cells. 200 microliters of these cells are then incubated for 10 minutes at room temperature with 1 microgram of the UAS-SEAP reporter, 1 microgram of the DNA binding domain containing construct, and 5 micrograms of the activation domain containing construct. Electroporation is performed at 250 mV, 129 Ohms on a BTX electroporator. The cells are allowed to recover at room temperature for another 10 minutes. They are then resuspended in 10 mLs of RPMI w/o phenol red supplemented with 10% FBS, penicillin, streptomycin, and Glutamate and returned to the 37 degree incubator with 5% $CO_2$ for 24 hrs.

After recovery, the cells are pelleted by centrifugation at 1000×g for 5 minutes and resuspended in 5 mLs of RPMI w/o phenol red supplemented with 10% FBS, penicillin, streptomycin, and Glutamate. 100 microliters of this cell suspension is plated on a 96 well plate. Appropriate dilutions of the dimerizer from an ethanolic solution (2 micromolar to 0.2 nanomolar) are made in the same media that the cells were resuspended in such that the concentration of ethanol is less than 1%. 100 microliters of these dilutions in media are added to the wells containing cells in the 96 well plate. The cells are again placed in the 37% incubator with 5% $CO_2$ for 24–48 hrs.

After incubation with the dimerizer the 96 well plates containing cells are wrapped in Saran Wrap and heated to 65–75 degrees C. for two hours. After heat treatment, the plates are placed at room temperature until cool. 100 microliters of each of the wells was transferred to a new plate containing 100 microliters of the following solution. For each 96 well plate prepare 11 mLs of 2M diethanolamine pH 10 (with $CO_2$) with 132 microliters of a solution of 1 mL 2M diethanolamine pH 10 (with $CO_2$) containing 25.6 milligrams of 4-MethylumbuliferylPhosphate (MUP). These plates are then returned to 37 degrees for 1–24 hours and are read on a microplate reader using a standard FITC filter set. The maximal reading should not exceed 1–2000 as this indicates that the substrate is nearly used up.

Example 5

Activation of Transcription Using CAB Fusion Proteins

The CABS have been extensively tested in a three-hybrid-like transcription assay as described in Spencer et al, 1993, Science 262:1019–1024, in WO 94/18317, in Rivera et al., 1996, Nature Medicine 2, 1028–1032 and in WO 96/41865 (Clackson et al). As described above, multimeric CABS, single full length or mini CABS or portions of the CABS have been fused C-terminally to the Gal4-DNA binding domain and placed between an N-terminal NLS and a C-terminal VP16 activation domain. Three copies of FKBP act as the other dimerization domain and are fused to either the C-terminus of Gal4 or between an N terminal NLS and the VP16 activation domain. The reporter contains the upstream activating sequence of GAL4 (12 tandem copies) followed by the secreted alkaline phosphatase gene (SEAP). FK506 titration was used to elicit dimerizer dependent transcription activation of SEAP which was detected on a fluorescence plate reader using methylumbyleriferyl-phosphate (MUP) as a substrate. The vector used for expression is a version of pCDNA3 from Pharmacia Biotech that has had its Xho1 and Sal1 restriction sites destroyed and a new polylinker inserted for ease of cloning. The cells used in these experiments are T-antigen transformed Jurkat T-cells.

The summary of our data in this transcription assay is as follows. The full length CABS (residues 12–394 of calcineurin A fused to residue 2 or to residue 3 of Calcinuerin B) are functional when fused to VP16 or to GAL4. They have an EC50 of ~1 nanoMolar.

We identified residues 340–370 of calcineurin A as being sufficient to form a complex with calcineurin B; residues 350–370 fail to complex with calcineurin B. This is also reflected in the fusion proteins using the mini-CABS, which all function to varying degrees with respect to total level of activation but behave almost identically with respect to EC50.

The linker length does seem to be able to modulate the amount of activity elicited by the CABS, but not the EC50s of the CABS, in the following way. The smallest linkers (7 or 8 amino acids) and the longest linkers (16–18 amino acids) tested appear to be the best with a total activation of around 8–10 fold and are comparable to the direct fusion between residues 340–394 of calcineurin A and residues 2 or 3–170 of calcineurin B.

The two versions of calcineurin B differ slightly in two respects. Calcineurin B from residues 3–370 seems to give a higher overall activation by about 10% but also seem to have a slightly higher background association with "free" calcineurin B and calcineurin A. Calcineurin B from residues 2–370 has a slightly lower overall activation but seems to interact less with free calcineurin A or "free" calcineurin B. It should be noted that this interaction with "free" calcineurin A or calcineurin B is extremely minimal. The average EC50 for activation for all of these constructs is between 1 and 3 nanoMolar.

The multimers of minicabs (340–394 of CNA and 3–170 of CNB) have been tested as fusions to VP16. 3, and 4 tandem CABS function identically to the best single CABS mentioned above when recruited to Gal4 fused to 3 FKBPs. 2 tandem CABS function twice as well with regard to total activation (~20 fold) and have an EC50 that is shifted to between 0.1 and 0.3 nanoMolar with FK506.

Example 6

Creation and Testing of miniCAB Proteins

Our analysis suggested that the N-terminal region of the CNA domain of CAB could be removed and the resulting protein could still be expected to bind FK506-FKBP. Four such minimal CAB proteins were created by PCR and ligation. Two of the miniCABs contained CNA residues 340–394 fused to either $CNB_{MG}$ or $CNB_M$(340miniCABs). The other two miniCABs contained CNA residues 350–394 fused to either $CNB_{MG}$ or $CNB_M$(350miniCABs). Each of these miniCABs was also fused to the VP16 transactivation domain.

Both of the 340miniCAB-VE constructs were able to stimulate SEAP activity when cotransfected with $FKBP_3$-GE in an FK506-dependent manner under standard SEAP assay conditions. Consistent with the relative activity of $CNB_{MG}$ and $CNB_M$, 340miniCAB$_{MG}$-VE was able to induce higher SEAP activity than 340miniCAB$_M$-VE. In contrast, neither of the 350miniCABs were able to stimulate SEAP activity in similar experiments. These results indicate that residues 340–394 of CNA represent a minimal domain of CNA that is able to form functional interactions with both CNB and FKBP-FK506 at the resolution detected by the SEAP assay.

The 340miniCAB$_{MG}$-VE construct also stimulates higher SEAP activity (6.5 0.6 fold) than the corresponding full length CAB$_{MG}$-VE (4.0 0.4 fold). The finding that the miniCABs produce higher SEAP activation than the full CABs might be attributable to the smaller miniCAB proteins being more stable or more efficiently translated or folded than the larger full length CAB proteins. The $EC_{50}$ of the miniCABs is about 3 nM, an order of magnitude greater than for full length CAB$_{MG}$-VE. This result is understandable given the fact that the full length CAB-VE is able to make more binding contacts with FK506-FKBP than the 340mini-CABs As with the full length CABs, assays were done to study whether the miniCABs were working through an inter- or intra-molecular mechanism. Like the full length CABs, the 340miniCAB-VEs showed only slight interaction with CNA-GE. In addition, both 340miniCAB-VE's showed only slight interaction with CNB-GE. This is in contrast to full CAB$_{MG}$-VE which shows a high level of interaction with CNB-GE. Perhaps the less bulky CNA domain of the 340miniCAB-VE is less efficient in finding intermolecular binding partners than the larger CNA domain of the full CAB. These are promising results for the use of miniCABs as dimerization domains since they imply that both mini-CAB-VE proteins, unlike full CAB$_{MG}$-VE, do not participate in unwanted intermolecular interactions which could lower the efficiency of the miniCAB proteins or cause them to interfere with the functioning of other proteins. Since the miniCABs do not seem to participate significantly in intermolecular interactions, this implies that the CNA and CNB domains of these proteins work together, and not independently in an intramolecular fashion, to form an FK506-FKBP binding site.

The results obtained imply that the 340miniCAB-VEs function as efficient dimerization domains in an intramolecular fashion, as designed. In addition, the 340miniCAB-VEs lack the catalytic domain of the full length CABs and, at 24 kDa, are approximately 35 kDa smaller.

Improving the Minicab System by Placing Multiple Dimerization Domains in Series

In previous dimerization systems, it had been observed that multiple dimerization domains fused to both the GAL4 DNA binding domain and the VP16 transactivation domain could increase the maximal amount of SEAP activity induced by the CID. For example, it was found that three FKBP molecules fused in tandem led to higher SEAP activity than did one, two or four FKBP molecules in series (Belshaw, P.J. et al. "Controlling Protein Association and Subcellular Localization with a Synthetic Ligand that Induces Heterodimerization of Proteins". PNAS. 1996. 93:4604–4607.) This is why $FKBP_3$ constructs have been used for all the experiments above. The optimal number of dimerization domains in tandem may be different for each domain. Multiple dimerization domains in series in a protein would increase the number of ligand binding sites on that protein. This would increase the effective affinity of a ligand for that protein. Too many dimerization domains in series would add excess bulk to the fusion protein and cause it to have unfavorable steric interactions with its environment. The balance between these factors determines the ideal number of dimerization domains to put in series for a particular construct.

In an effort to improve the miniCAB dimerization system, constructs with one, two, three or four 340miniCABs in series fused to VE were created through ligations of existing constructs (called (340miniCAB)$_n$-VE where n=1, 2, 3, 4). There was a 2 residue linker between each 340miniCAB subunit due to the restriction profile of the miniCAB constructs. The multiple 340miniCAB constructs were only made with $CNB_{MG}$ containing miniCABs since these gave the best signal in the dimerization assay.

Figure 4:
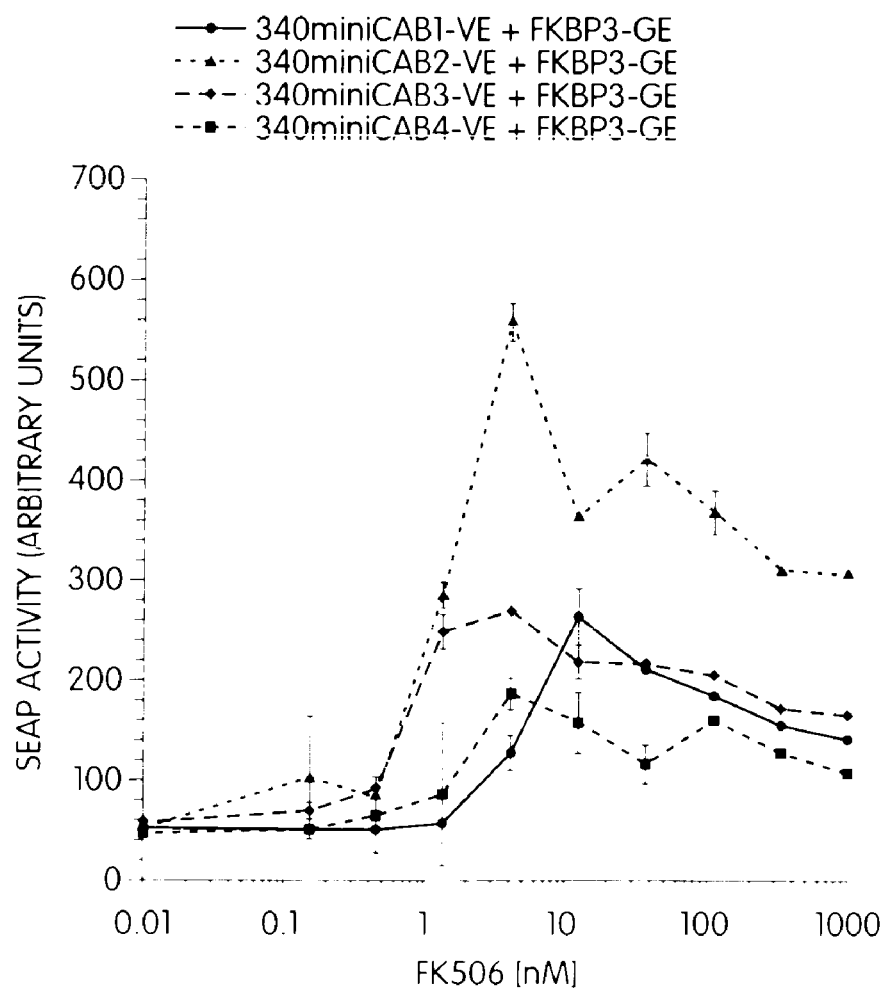
FIG. 4: Effect of varying the number of CAB domains on secreted alkaline phosphatase activity.

FIG. 4 shows that two 340miniCAB domains in series give rise to the highest SEAP activity (9.9 0.4 fold) in the presence of FK506 when cotransfected with FKBP$_3$-GE. One and three 340miniCABs in series result in similar levels of SEAP activity while four miniCABs give a very low signal. The EC$_{50}$ of two and three miniCABs in series is similar with a value of approximately 1.3 nM and is lower than that for one miniCAB. Like 340miniCAB$_{MG}$-VE, (340miniCAB$_{MG}$)$_2$-VE shows little intermolecular association with CNA-GE or CNB$_{MG}$-GE, thereby implying that the activity of this construct is due to its CNA and CNB domains working together in an intramolecular fashion.

Currently, the (340miniCAB$_{MG}$)$_2$ domain represents the most optimized CAB dimerization reagent.

Example 7

Implementing CAB Mediated Dimerization in Contexts Other than CAB-VE

In order to show that CAB truly represents a useful new dimerization domain, it must function in the context of activation domains other than VP16. A simple test of CAB versatility would be to create a new transcription activation system in which CAB-GE could be shown to heterodimerize with FKBP-VE. This is the same as the original CAB-VE system except that the activation domains to which CAB and FKBP are fused have been swapped. To implement the new system, six CAB-GE constructs were made. Two of these were full length CABs with either CNB$_{MG}$ or CNB$_M$. The other four were 340miniCABs and 350miniCABs with either form of CNB. In order to test these proteins, an FKBP-VE fusion protein was needed. As with FKBP$_3$-GE, FKBP$_3$-VE was already available in a PBJ5 vector and was easily transferred to the pcDNA3/m.jy2 vector used for all constructs in this project.

We found that the CAB-GE's work similarly to the CAB-VE constructs. However, the full length CAB$_{MG}$-GE protein only enhance SEAP activity 2.0 fold whereas the full length CAB$_{MG}$-VE protein could enhance it by approximately 4 fold. Both full CAB-GE and CAB-VE are able to stimulate SEAP activity when heterodimerized to FKBP$_3$-GE, demonstrating the versatility of the full CAB domain. In addition, they do not stimulate activity in the absence of FK506. This result implies that the presence of an intact phosphatase active site on the full length CABs is not responsible for enhanced SEAP activity, a concern raised initially by the constitutive association experiments between CNA and CNB described above.

The 340miniCAB-GE constructs enhance SEAP activity to the same level as the 340miniCAB-VE constructs. No difference was seen between 340miniCAB$_{MG}$-GE and 340miniCAB$_M$-GE. Like 340miniCAB-VE, 340miniCAB$_{MG}$-GE does not show significant constitutive activity with CNA or CNB and thus, seems to work through an intramolecular mechanism as opposed to an intermolecular mechanism.

Example 8

Probing the Difference Between Full Length CAB-GE and miniCAB-GE

Further experiments were done to explore why the full length CAB$_{MG}$-GE construct was not working as well as its 340miniCAB$_{MG}$-GE counterpart (a trend also observed with the VE CAB proteins). The normal SEAP assay protocol calls for transfecting a 1:5 ratio of GE construct DNA to VE construct DNA. This ratio has been empirically determined to give the best results for the FK1012 and rapamycin dimerization systems. Presumably, the ratio of transfected DNA affects the ratio of translated GE and VE containing proteins. A series of SEAP assays were performed with full CAB$_{MG}$-GE in which the ratio of transfected GE DNA to VE DNA was changed from 1:5 (normal) to 1:1 to 5:1 while keeping the total amount of transfected DNA constant. As the amount of full CAB$_{MG}$-GE DNA was increased the enhancement of SEAP activity increased as well.

A similar series of experiments was performed for 340miniCAB$_{MG}$-GE, but changes in the GE DNA to VE DNA transfection ratio did not affect maximum induced SEAP activity as significantly as for the full CAB$_{MG}$-GE construct. Interestingly, in the 5:1 GE DNA to VE DNA experiment, the maximum amount of SEAP activity induced by full length CAB$_{MG}$-GE was equal to that produced by 340miniCAB$_{MG}$-GE. Even though protein expression levels were never directly examined, these results suggest that greater expression of full CAB$_{MG}$-GE, assuming more transfected DNA leads to higher levels of expression, increases its performance as a dimerization domain up to the level achieved by 340miniCAB$_{MG}$-GE. This finding supports the previously presented suggestion that miniCABs perform better than full CABs because their smaller size makes them more stable or more efficiently translated or folded than the larger full length CAB proteins.

Example 9

Synthesis of C40 Bumped FK506
Extraction/Purification of FK506

Powder from Prograf™ brand pharmaceutical tacrolimus capsules was suspended in water and FK506 was extracted using 3/7 volume of EtOAc and collected by rotary evaporation. Crude FK506 extract was purified by size exclusion chromatography using a Japan Analytical Industries LC-908 recycling preparative HPLC equipped with tandem J14 and J11 9C13 columns (herafter referred to as "Sizing JAI"). The identity of this material was confirmed by TLC, FAB-MS, and proton NMR.

Synthesis of C40-phenyl-FK506

12 mg of purified FK506 was sealed with a stir bar in a flame-dried 20 ml roundbottom flask and the flask purged with argon. 12 ml of CH2Cl2, freshly distilled over CaH2, was injected and stirred briefly to solubilize the FK506. 0.25 mL of styrene (150 eq.) was injected, along with 2.2 ml CHCl2 containing 3.6 mg (0.3 eq) of the Grubbs catalyst, bis-tricyclohexylphosphine benzylidine ruthenium chloride. The final reaction concentration of FK506 was thus about 1 mM. This reaction mixture was stirred under argon for 24 h at room temperature. Products and unreacted SM were collected by rotary evaporation, solubilized in ethyl acetate, and filtered through Celite. At this point, fresh solvent, styrene, and catalyst were added in the same proportions and the reaction repeated for an additional 24 h.

Purification of C40-phenyl-FK506

Following rotary evaporation and filtration as described above, the product/SM mixture was resuspended in CH2Cl2 and separated by flash chromatography using a stepwise gradient of a) CH2Cl2, b) 18:1:1 CH2Cl2: iPrOH:PhH, c) 12:1:1 CH2Cl2:iPrOH:PhH, and d) 9:2:2 CH2Cl2:iPrOH: PhH. Column fractions were analyzed by TLC and compared with standards to facilitate pooling into three major fractions which were analyzed by FAB-MS. Fraction I contained styrene and stilbene, fraction II contained FK506 and C40-phenyl-FK506, and fraction III contained FK1012 (the FK506 self-metathesis product). The components of fraction II were separated by two rounds of HPLC. First, the mixture was separated by affinity HPLC using a Japan Analytical Industries LC-908 recycling preparative HPLC equipped with two tandem JAIgel GS310 columns (hereafter referred to as "Affinity JAI"). Crude C40-phenyl-FK506 as well as crude recovered FK506 were obtained in this fashion. Second, each crude fraction from the Affinity JAI was purified to homogeneity by Sizing JAI as described above. The identity of each purified compound was confirmed by FAB-MS and proton-NMR analysis.

Synthesis/Purification of Other C40-Derivatized FK506s

In each case, the synthetic route to preparing these derivatives is essentially that described above, using the appropriate terminal olefin compound (usually a substituted styrene) instead of styrene itself. For example, p-phenoxystyrene was used in the synthesis of C40-p-phenoxy-phenyl-FK506, and m-fluorostyrene was using in the synthesis of C40-m-fluorophenyl-FK506. The principal means of following reaction progress was FAB-MS, with emphasis on the appearance of a parent ion peak which corresponds to the desired product. During purification, FAB-MS was also used to quickly identify the components of JAI fractions. In this case, however, emphasis was placed upon the absence of the parent ion peak corresponding to FK506. This focus is necessary since FK506 is competitive with each product in biological applications, so its absolute absence was considered more important than was maximizing product yields. In some cases, the sequence of JAI purification steps were reversed (i.e. Sizing JAI first, then Affinity JAI), or more such steps were added, in pursuit of this goal.

Example 10

Construction of CAB/p65 Fusion Proteins

CAB/p65 fusion proteins were prepared in the pBJ5.2X vector, which contains an SV40 origin of replication for high-copy number in mammalian cells transformed with the large tumor antigen. This version of pBJ5 does not contain a selection cassette for mammalian cells and contains the ampicillin-resistance cassette for selection in bacterial cells. This plasmid contains an SRa promoter for high-level expression in mammalian cells. The polylinker sequence of this plasmid consists of the following elements (HA is the hemagglutinin epitope tag):

NotI/SacII-Kozak-ATG-XhoI-SalI-HA-SpeI-TAA

Primers containing restriction sites were prepared in order to amplify two different fragments of calcineurin A, corresponding the the full-length CAB (fCAB) and the minimal CAB (mCAB). These PCR fragments were subcloned directionally into the polylinker to generate the following constructs:

ATG-XhoI-CnA (12–394)-SalI-SpeI-TAA-EcoRI

ATG-XhoI-CnA (340–394)-SalI-SpeI-TAA-EcoRI

Primers containing restriction sites were prepared in order to amplify the fragment of calcineurin B corresponding to residues 3–170 of this protein. These PCR fragments were subcloned directionally into the constructs already containing calcineurin A fragments, producing the following CAB constructs (S\X represents a fusion of complementart SalI and XhoI restriction sites which can no longer be cut by either enzyme):

ATG-XhoI-CnA (12–394)-(S\X)-Cn B (3–170)-SalI-HA-SpeI-TAA

ATG-XhoI-CnA (340–394)-(S\X)-Cn B (3–170)-SalI-HA-SpeI-TAA

To study the ability of the CABs to mediate transcriptional activation in the context of FKBP:FK506, a (XhoI/SpeI) fragment containing the transcriptional activation domain of the p65 subunit of NF-kB was inserted into (SalI/SpeI) digested mCAB constructs. This fusion results in another (SalI/XhoI) fusion which cannot be cut by either enzyme. A similar strategy is possible to generate multimers of the CAB domain, greatly facilitating the production of these reagents. Since all of the restriction enzymes within the coding region are 6-base cutters, they preserve the reading frame for protein synthesis. The mature CAB should have the following amino acid sequence:

$NH_2$-Met-Leu-Glu-(CnA frag)-Val-Glu-(CnB frag)-Val-Asp-Thr-Ser-COOH (SEQ ID NO 22)

New mCAB-p65 constructs were verified by sequence analysis.

Example 11

Demonstration of FK506-Derivatives as "Bumps" by Calcineurin Inhibition Assay

Figure 7:
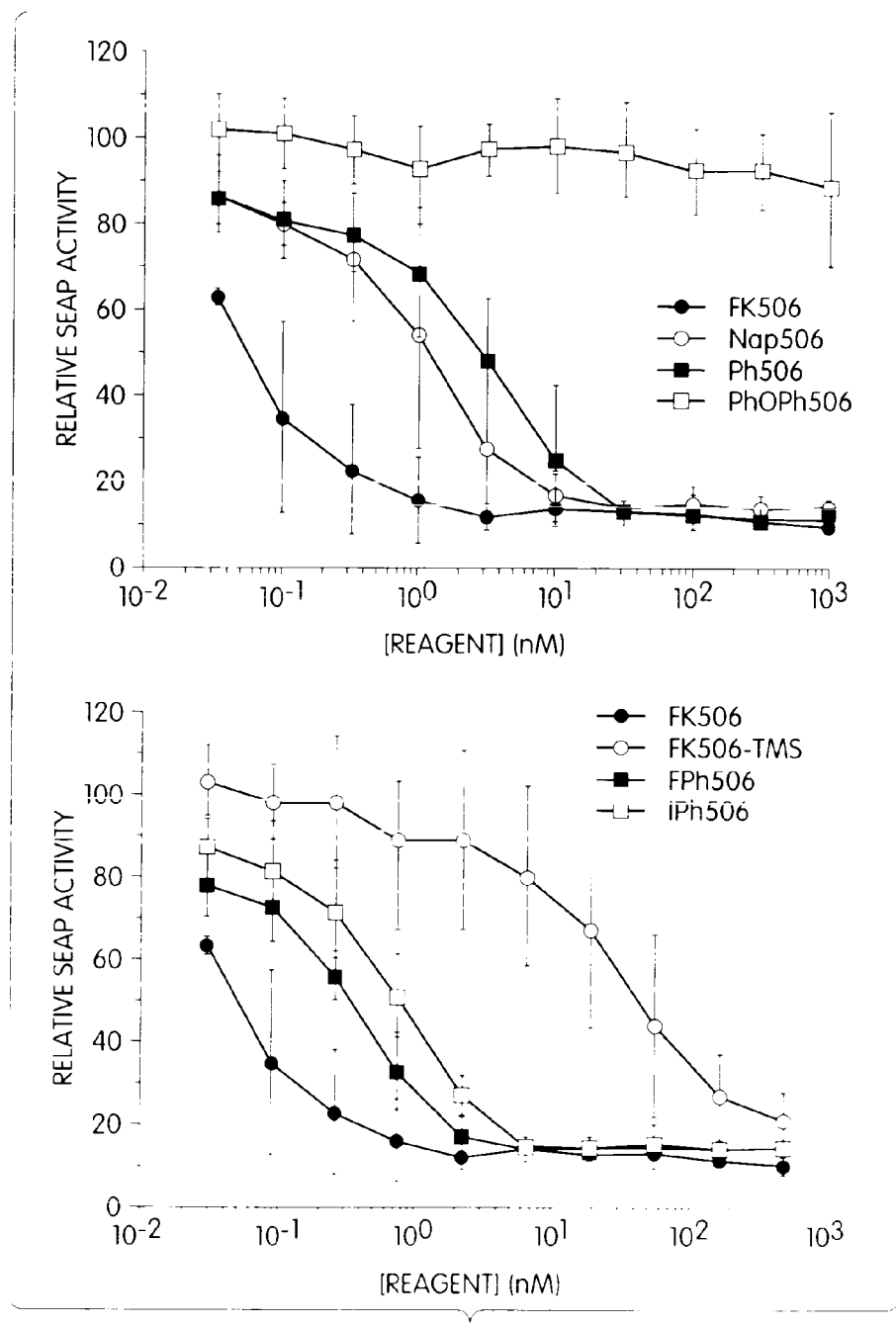
FIG. 7: Effect of C40 derivatization on calcineurin-dependent reporter gene activity. Results represent the average of at least three independent experiments per derivative. Abbreviations: Nap, naphthyl; Ph, phenyl; PhOPh, phenoylphenyl; TMS, trimethylsilyl; FPh, fluorophenyl; Iph, iodophenyl.

To demonstrate that the FK506 derivatives are less effective at binding calcineurin than is FK506 itself, we performed reporter gene assays that are sensitive to the action of FK506 on calcineurin. In particular, we transfected human TAg Jurkat T cells with a reporter construct, NFAT-SEAP, which consists of 12 copies of the NFAT response element fused upstream of the gene for secreted alkaline phosphatase (SEAP). Following transfection, the cells were exposed to phorbol myristate acetate (PMA) and ionomycin (IO), which together are able to activate NFAT-SEAP reporter activity. FK506, by inhibiting calcineurin, antagonizes the effect of PMA+IO in a dose-dependent manner. Specifically, ten million Jurkat cells per condition were transfected with 500 ng of NFAT-SEAP reporter construct by electroporation (40 ms pulse) and aliquoted at $0.3 \times 10^6$/well into a 96-well microtiter plate. PMA (50 ng/mL) and IO (1 µM) were added to all cells, and serial dilutions of FK506, FK506 derivative, or vehicle, were added. Cells were incubated 36 hours in a tissue culture incubator, then heat-inactivated for 2 hours at 65° C. Following heating, 100 µL of cell supernatants were transferred to a replica plate containing 100 µL of assay buffer (120 µM 4-methylumbelliferyl phosphate in 2M diethanolamine bicarbonate, pH 10). Assays were incubated 8 hours before reading on a Fluoroskan plate reader. The results of these experiments are shown in FIG. 7.

We assumed that the reduced ability of the FK506 derivatives (as judged by their higher $IC_{50}$ in this assay) to antagonize reporter gene activity is due to an impairment in the ability of the FKBP:ligand complex to bind calcineurin. Other possibilities for the reduced activity of derivatives in this assay are 1) compound insolubility in tissue culture media, 2) inability of compound to penetrate the cell membrane, or 3) inability of compound to bind to FKBP. To rule out these other possibilities, we tested two of the derivatives for their ability to suppress a rapamycin-dependent effect in mink lung cells (Paul A Clemons and Brent Stockwell, unpublished observations). As both the phenyl and phenoxyphenyl derivatives were able to suppress the effects of rapamycin in this context, we believe that each is soluble, cell-permeant, and able to bind FKBP.

Example 12

Effect of Overexpression of Full-Length CABs (fCABs) on Reporter Gene Activity

Figure 8A:
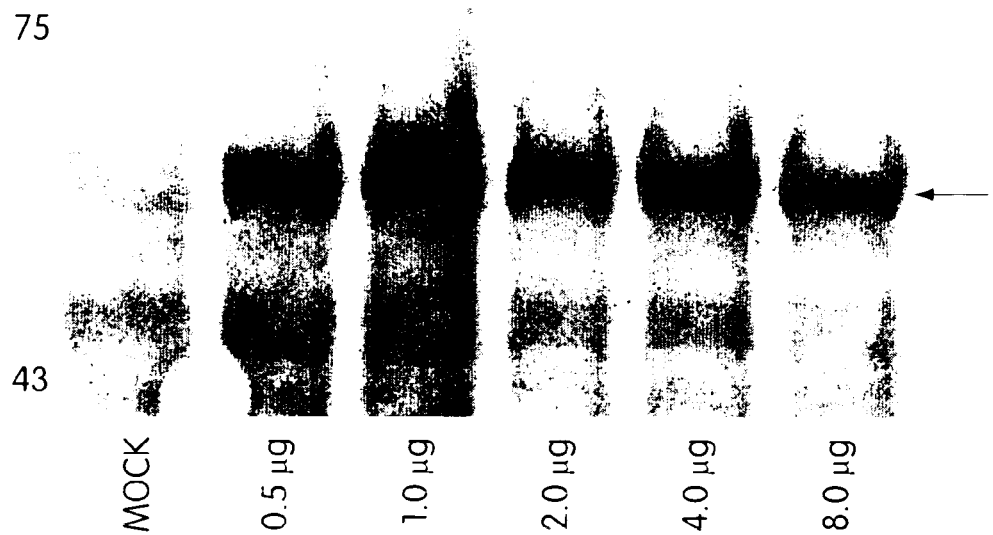
FIG. 8: Effect of high-level fCAB expression on NFAT-SEAP reporter gene activity. SEAP assays were carried out as described above except that aliquots of transfected cells were grown up separately for analysis by Western blotting. A. Western blot using antibodies (3F10, Gibco) directed against the HA epitope tag., and showing the expression of fCAB protein as a function of the concentration of transfected DNA. B. SEAP assay results showing the high constitutive reporter activity in the presence of overexpressed fCAB. Data shown is for 400 ng of transfected fCAB DNA.
Figure 8B:
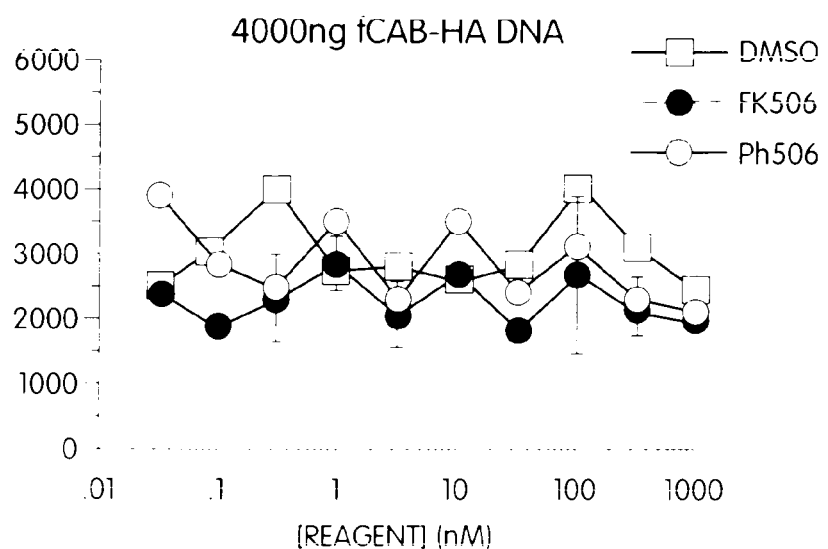

In contrast to the assay described in the previous section, we wanted to test the ability of the bumped compounds to inhibit the phosphatase activity of the full length CABs (fCABs) upon transient transfection of these constructs. Initial experiments involved the co-transfection of 500–5000 ng of fCAB construct DNA along with 500 ng of NFAT-SEAP reporter gene. FIG. 8 shows the results of these experiments, in which a high level of fCAB overexpression overcame the ability of FK506 or its derivatives to inhibit reporter gene activity. Also shown is a Western blot corresponding to each concentration of construct DNA transfected.

Figure 9:
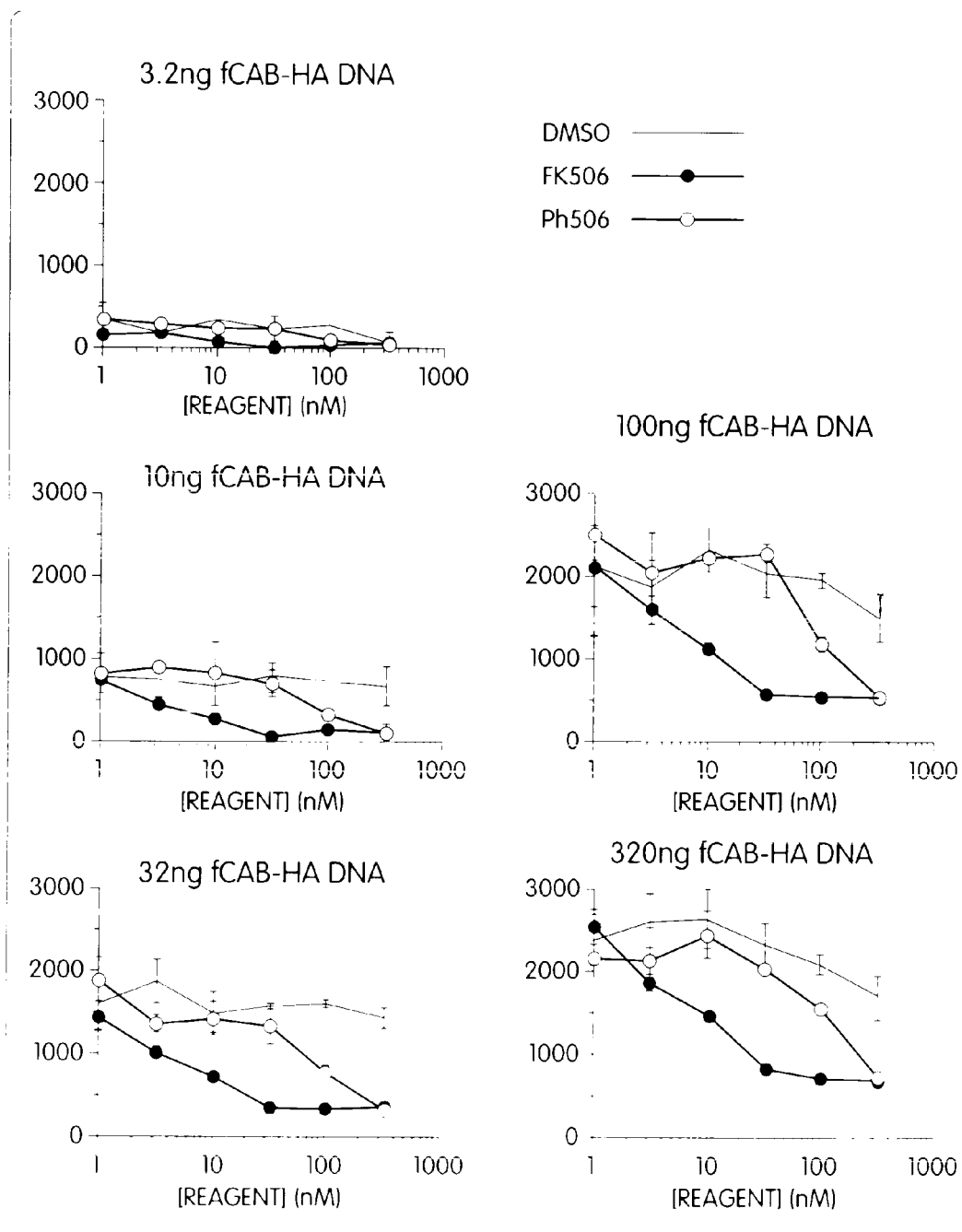
FIG. 9: Tuning of phosphatase assay as a function of fCAB construct DNA concentration. SEAP assays were carried out as described above using the indicated amount of fCAB construct DNA. Data represent the average of two independent experiments.
Figure 10A:
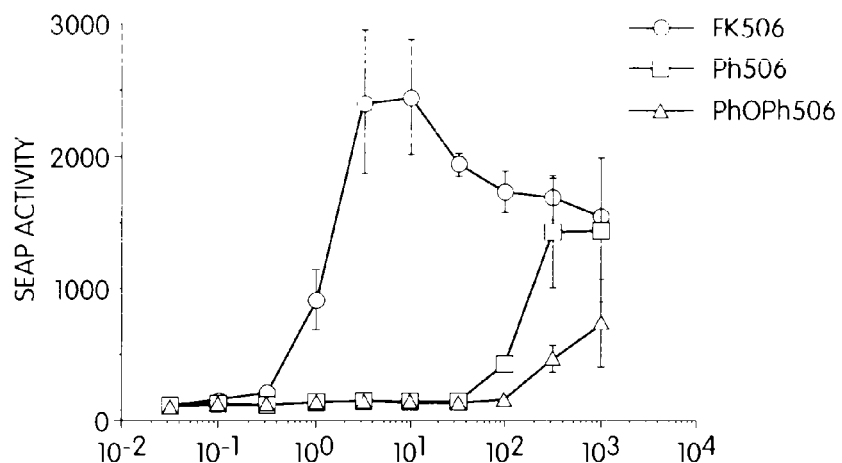
FIG. 10: Development of FK506-mediated transcription assay using CAB-p65 fusion proteins. SEAP assays were carried out as described using the optimized concentrations of each DNA species and the indicated dose of FK506 or FK506 derivative. A. SEAP assay results showing the activation of transcription by FK506 and two derivatives. Data represent the average of three independent experiments. B. SEAP assay results showing the behavior of the dose response with many closely-spaced doses over a narrow concentration range. Data represent the results of three independent experiments.
Figure 10B:
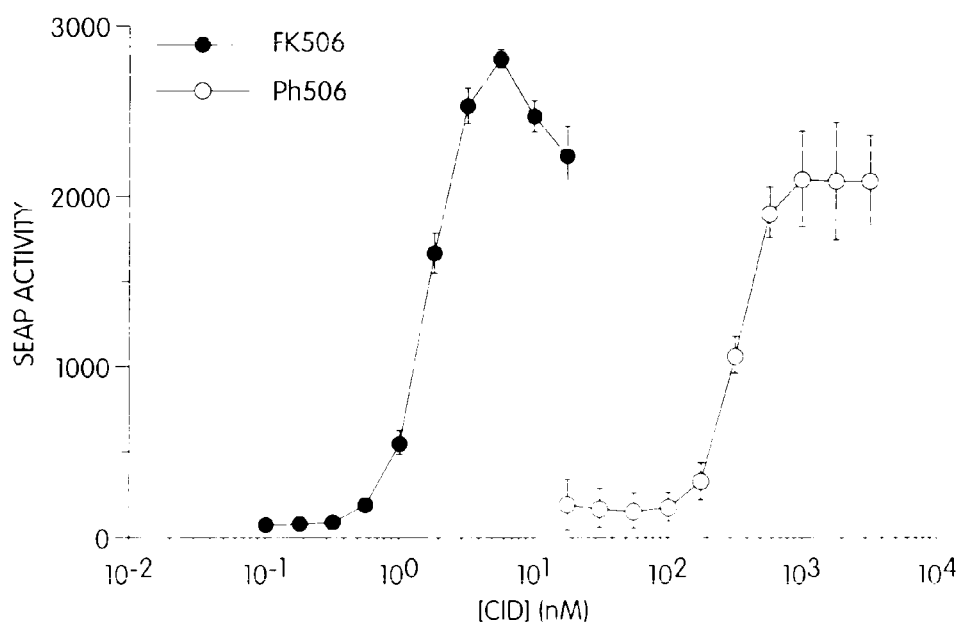

To tune the phosphatase assay in the context of transiently transfected fCABs, we performed SEAP assays as described above while varying the concentration of fCAB construct DNA between 3.2 ng and 320 ng. The results of these experiments are shown in FIG. 9.

Example 13

Optimization of CAB Transcription System Based on mCAB-p65 Constructs

In order to screen for mutants CABs which can restore binding to FK506 derivatives, we prepared fusions of the mCAB module to the N-terminus of the activation domain of p65, as described above. Our rationale for the use of this activation domain was that the original transcription construct, with the mCAB fused to VP16, gave low signal amplitudes in the transcription assay. We hoped that changing activation domains would improve this signal and give a stable $EC_{50}$ for transcriptional activation. Both of these are required for effective screening of pools of mutants using the transcription assay.

Briefly, we transfected human TAg Jurkat T cells with a a reporter construct (GRE-SEAP) containing 12 copies of the Gal4 response element upstream of the gene for SEAP, along with Gal4-$(FKBP)_3$ and the mCAB-p65 fusion. FK506, a derivative, or vehicle were added to cells in a 96-well plate as with the NFAT-SEAP assay. Initial trials gave very promising results, so we undertook to optimize the transcription system by systematic variation of DNA concentrations for each of the three constructs. In three successive experiments, we found the following optimal DNA concentrations for these transfections:

| | |
|---|---|
| GRE-SEAP reporter gene | 500 ng |
| Gal4-$(FKBP)_3$ DB fusion | 1500 ng |
| mCAB-p65 AD fusion | 500 ng |

Following optimization of DNA concentrations, we tested FK506 and two derivatives in the transcription assay. The results of this experiment are shown in FIG. 10A. The amplitudes of activation in these experiments are sufficient to warrant an attempt to screen pools of CAB mutants for compensatory binding.

To address the stability of the dose response in these cells, we carried out a finer titration of FK506 and phenyl-FK506. These data are shown in FIG. 10B, which illustrates this property and indicates that the transcription system comprises a viable assay for screening pools of CAB mutants for compensatory binding.

Example 14

Mutagenesis Strategies for CAB "Hole" Discovery

As described above, we envision the use of the improved transcription system to screen pools of mutants for compensatory binding to FK506 derivatives. Put simply, this involves transfection of mixtures of DNA species corresponding to mCAB-p65 mutants, then looking for leftward shifts in the dose-response curves depicted in FIG. 10.

To mutagenize the mCAB-p65 constructs, we prepared degenerate, internal primer pairs at each of the amino acid positions to be mutagenized. These primers are fully degenerate at the codon corresponding to their respective amino acid position (the positions are the same six positions outlined in the original document). Using each primer and the corresponding (antiparallel) primer outside the coding region (in the vector arms), two degenerate, overlapping PCR products were generated. In a secondary PCR reaction, these two fragments were used as template and amplified by overlap extension using the two external primers. These final products were digested and placed back into the pBJ5.2X host vector. It is these libraries that will be screened in the transcription assay for compensatory mutants.

Another strategy for identifying potential compensatory mutants is one involving a yeast three-hybrid system. In such a system, yeast are transformed with a DNA-binding fusion to one dimerization domain and an activation domain fusion to the other dimerization domain, along with an appropriately responsive reporter which drives expression of a nutritional marker gene. Yeast transformants are screened for the recovery of growth at a concentration of FK506 or derivative which does not permit growth of yeast harboring the "wild-type" mCAB-p65 construct. The advantage of such a system is that many more clones can be screened simultaneously, allowing multiple amino acid positions in the mCAB to be randomized simultaneously. Use of such three-hybrid systems for screening mutagenized libraries of FKBP and FRB domains are described in U.S. Pat. No. 5,830,462 and WO 96/41865.

The system used to screen CAB libraries is based on the MatchMaker LexA Two-Hybrid System from Clonetech (Catalog # K1609-1). It utilizes two vectors, pLex-A and pB42AD, that contain a DNA binding domain from Lex-A and an activation domain (B42), respectively. In addition, the yeast strain EGY48 contains an integrated LEU2 reporter under the control of the $LexA_{op(X6)}$-Leu2 operator enabling one to directly screen for LexA induced reporter activation on LEU2 dropout plates.

The normal polylinker from pB42AD was removed and replaced with the polylinker described below. I have fused single copies of FKBP and the CABS C-terminal to both domains.

LexA-miniCAB-E (E=Flag epitope tag)

B42AD-FKBP-E (E=Flag epitope tag)

Using this system, ~5 million different mutant mCABS can be screened simultaneously on a single petri dish using very small amounts of compounds. Some or all of the residues that will putatively be in contact with the allyl sidechain, or a substituent on the allyl sidechain, of FK506 can be mutated individually or simultaneously by PCR with the oligonucleotides indicated below. These libraries are then ligated into the Lex-A-miniCAB-E construct and electroporated into DH5-alpha e-coli electrocompetent cells from Gibco BRL. The DNA is amplified in DH5-alphas, purified, and transformed into the yeast strain EGY48 that are expressing B42AD-FKBP-E. The library will be further amplified in yeast by growth on -HIS-TRP plates with Glucose as the sugar source (for selection of both the LexA-mCAB and B42AD-FKBP constructs) then plated onto -HIS-TRP-LEU Galactose/Raffinose plates containing 100 nM concentrations of each of the bump compounds. Colonies that grow will be checked by plating onto -HIS-TRP-LEU Galactose/Raffinose plates in the absence of compounds to distinguish between mutants that allow constituitive assocation (ie. False positives) from those that facilitate drug induced association. The colonies that do not grow on the previous control will then be re-plated onto -HIS-TRP-LEU+Galactose/Raffinose with 100 nM of each of the individual bump compounds to be sure that the compounds induce growth. Those that grow will then be compared by plating them onto -HIS-TRP-LEU+Galactose/Raffinose plates with 3 fold dilutions of the bump compounds. The clones that allow the lowest concentration of drug to induce growth will be further analyzed. The DNA from the best postive clones will be rescued or PCR'd to give template for sequencing of the positive hits. These mutants will then be tested in one or more of the assays (ie. transcription assay with mCABS) that we have developed in cell culture for verification of the improvement of affinity of the miniCABS for the bump compound in the context of FKBP. The shuttling of these mutant miniCABS into these other systems can be accomplished by a simple ligation since they all contain a 5' Xho1 site and a 3' Sal 1 site and a 3' Apa1 site.

Preparation of the Constructs:

A. pB42AD constructs.

The pB42AD vector was digested with EcoR1 and Xho1, gel purified and ligated to the following polylinker to give pB42AD-PL3. All of the constructs made with PB42AD are in this pB42AD-PL3 vector.

Polylinker Oligos for pB42AD:

The following two oligonucleotides were phosporylated with polynucleotide kinase, annealed, and ligated into pB42AD that had been digested with EcoR1 and Xho 1 to give a new polylinker with the following restriction sites in order.

```
5' Xho1-Spacer-Sal1-Nco1-BstEII-BspEI-AflII-ApaI-EcoR1 3'

5' tcg acg aat tcg ggc ccc tta agt ccg gag gtc acc cat ggg tcg acg tcg tcg gta gac tcg aga 3'
(SEQ ID NO 23)

5' aat ttc tcg agt cta cga ccg acg tcg acc cat ggg tga cct ccg gac tta agg ggc ccg aat tcg 3'
(SEQ ID NO 24)
```

The miniCABS and FKBP from previously reported constructs were then digested with Xho1 and EcoR1 and ligated directly into pB42AD-PL.

B. pLexA constructs.

The following oligos were used with standard PCR conditions to generate an FKBP fragment with a 5' EcoRI and a 3' BamHI. pLexA and this fragment were digested with EcoRI and BamHI, gel purified, and ligated.

FKBP oligos:

1. FKBP Y2H$^{ex}$ 5' (5' oligo for FKBP with EcoR1 and Xho1 restriction sites

```
              EcoR1    Xho1    Met
5' c ggg ccc ccc gaa ttc ctc gag atg ggc gtg cag gtg gag ac 3'
(SEQ ID NO 25)
```

2. FKBP Y2H$^{sb}$ 3' (3' oligo for FKBP with 3'Sal 1 and BamHI restriction sites. No stop condon)

```
              BamH1   Sal1    E
5' ggg tct gga tcc gtg gac ttc cag ttt tag aag ctc g 3' (SEQ ID NO 26)
```

Construction of the miniCABS for pLexA:

mCABS were PCR'd with standard PCR conditions off of my original miniCAB template with the followin oligos and digested with NcoI and BamHI. This gel purified fragment as ligated to gel purified pLexA digested with BamHI and NcoI.

3. mCAP Y2H$^{ex}$ 5' (5' oligo for mCAB starting at residue 340 of CNA with 5' BamHI and Xho1 sites

```
                    BamH1   XhoI    Pro340
5' a tat aaa tcg gga tc cgt ctc gag cca tac tgg ctt cca aat ttc atg g 3' (SEQ ID NO 27)
```

4. mCAB Y2H$^{sfann}$ 3' (3' oligo for mCAB with 3' SalI, Flag, Stop, Apa1, Not1, and Nco1)

```
               Nco1  Not1        Apa1    stp ----------Flag------------Sal1
5' tct ttaa cca tgg cgg ccg c ggg ccc tca ctt gtc atc gtc atc ttt ata gtc gac cac atc tac
cac cat c 3' (SEQ ID NO 25)
```

C. Mutagenic Oligos for mCABs. The following are the oligonucleotides used to generate the libraries of mutant mCABS. They were constructed with the codon NN(G/C) (N=G, A, T, or C) at each of the following positions that we mutagenized. The numbering scheme from each of the independent proteins in the mCAB is retained.

For the CNB portion an overlap mutagenesis strategy was employed. An N-terminal fragment without mutations was PCR'd from my original miniCAB template. This has a region that will anneal with a C-terminal fragment generated by PCR with the indicated oligonucleotides. These two fragments were mixed and subjected to PCR with standard conditions to generate a fragment with an N-terminal Pflm1 site and a C-terminal Apa1 site. Since this reaction generated a visible fragment of the proper size it was then further amplified with oligo 4. above (mCAB Y2H$^{sfann}$ 3') and the Pflm1 oligo below to generate a significant amount of product. This was then digested with Pflm1 and Nco1 and ligated into pLexA-mCAB-E that had been digested with Pflm1 and Nco1 and gel purified. The CNA portion of the mCABS was mutagenized with the oligos under 2. below by PCR to generate a small fragment of the mCAB with a 3' Pflm1 site and a 5'Xho site. This was ligated into pLexA-mCABE digested with Pflm1 and Xho1. To generate the 5 position library this can be ligated into pLexA-mCABE library with the 3 positions mutagenized.

1. Overlap extension mutagenesis of the CNB portion of the mCABS.

5' oligo for generation of the N-terminal portion of CNB for overlap.

```
                  Pflm1
5' ct tgg tcc ctt cca ttt gtt ggg gaa aaa gtg act gag 3' (SEQ ID NO 29)
```

3' oligo for generation of the N-terminal portion of CNB for overlap.

```
5' ggg aac aat ctg aaa gat aca cag tta cag c 3' (SEQ ID NO 30)
```

5' mutagenic oligo for generation of C-terminal portion of CNB for overlap.

```
                         Val119    Met118         Leu115
5' gctg taa ctg tgt atc ttt cag att gtt ccc (g/c)NN (g/c)NN cat ctt (g/c)NN tac ctg
gaa gag ttc ccc 3' (SEQ ID NO 31)
```

3' mutagenic oligo for generation of C-terminal portion of CNB for overlap.

```
         XbaI BglII ApaI  Stp ---------FLAG---------  SalI    170
5' ttaa tct aga tct ggg ccc tca ctt gtc atc gtc atc ttt ata gtc gac cac atc tac cac
cat c 3' (SEQ ID NO 32)
```

2. Mutagenic oligos for the CNA portion of mCABS.

5' Mutagenic oligo with 5' Xho 1 site.

```
                  XhoI    340
5' atat aaa tcg ctc gag cca tac tgg ctt cca aat ttc atg g 3' (SEQ ID NO 33)
```

3' Mutagenic oligo

```
                       PflM1                      353         352
5' ctc agt cac ttt ttc ccc aac aaa tgg aag (g/c)NN (g/c)NN agt aaa aac atc cat g 3'
(SEQ ID NO 34)
```

Example 15

Use of the Cab Domain in Complex with Multiple Binding Partners

In order to engineer a cell containing both FKBP/FK506/CAB complexes as well as cyclophilin/cyclosporin/CAB complexes, one would first test the ability of the CAB domain to form cyclophilin/cyclosporin/CAB complexes by replacing FKBP directly with cyclophilin in the transcription assay described in example 4. Thus, the cell would be transfected with a first fusion protein containing cyclophilin and a DNA binding domain such as GAL4, and a second fusion protein containing a CAB domain fused to a transcription activation domain such as p65. Reporter gene expression would be detected following addition of cyclosporin to the cells. Such experiments have been described in WO 98/08956, especially in Example 3. Once formation of cyclophilin/cyclosporin/CAB complexes is demonstrated, one would then show that cells containing both cyclophilin and FKBP fusion proteins could form the appropriate complexes upon addition of the correct ligand.

Figure 5:
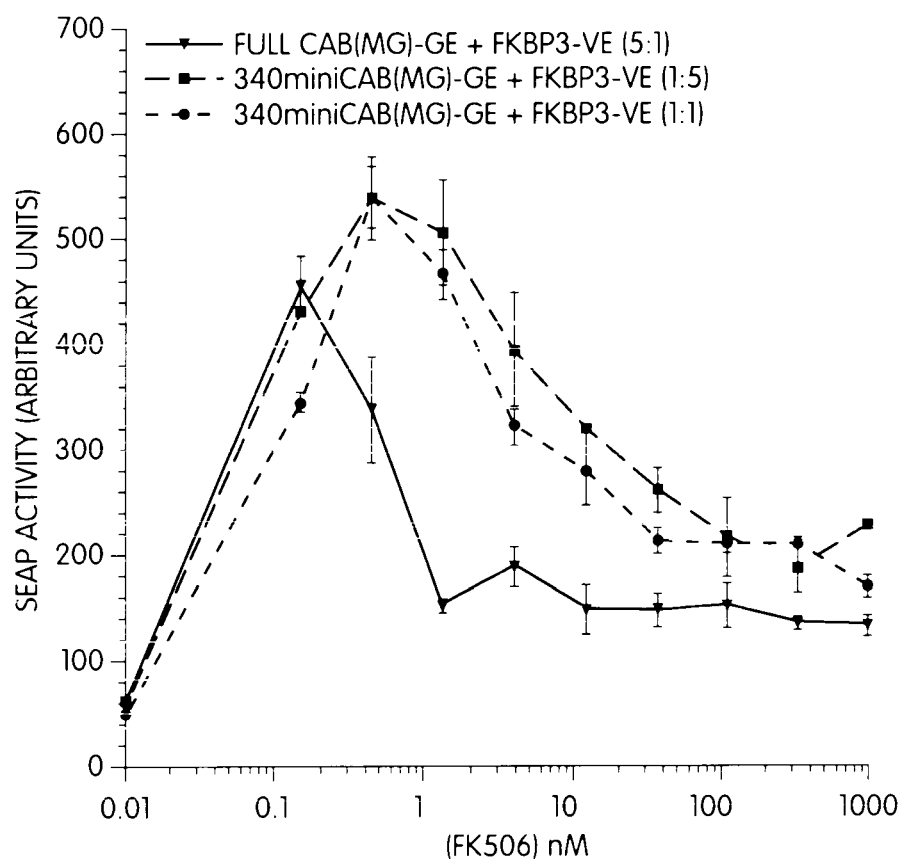
FIG. 5: Secreted alkaline phosphatase activity induced by full length CABs and mini CABs.

A proof of principle experiment for each of the modes of CAB function illustrated in FIG. 5 would involve fluorescent proteins. To demonstrate the recruitment of either FRB or CAB to the same (FKBP) dock, we would make fusions of each of these modules to a different fluorescent protein, such as BFP and GFP, then cotransfect these constructs with a nuclear (or membrane-localized) FKBP construct. Treatment with rapamycin, FK506, or both should result in translocation of either or both of the fluorescence signals to the nucleus (or membrane). To demonstrate the docking of CAB with either FKBP or cyclophilin, we would make fusions of each of these immunophilins to a different localization signal sequence, such as those for nuclear or membrane localization, then cotransfect these constructs with CAB-GFP. Treatment with FK506, cyclosporin, or both, should result in translocation of green fluorescence signal to the appropriate location. These experiments would ideally be backed up immunoprecipitation studies. For example, one could use an antibody to calcineurin or the CAB domain to immunoprecipitate the CAB domain in the presence of FK506 or cyclosporin. One would then run the immunoprecipitates on SDS-page, perform a Western transfer and detect the complex formation by blotting with antibodies to either FKBP or cyclophilin.

A use for this system has been envisioned in the conditional regulation of the protein kinases Akt and PDK1. These kinases are regulated by their proximity to each other and to the membrane in a complex way. Using the first mode of localization discussed above, but replacing each of BFP and GFP with one of these kinases, we could perform order of addition experiments with rapamycin and FK506 in which we monitor treated cells for readouts known to be downstream of one or the other of these kinases. Because these kinases impinge, directly or indirectly, on pathways involving the cellular targets of both rapamycin and FK506, one would preferably have "bump-hole" solutions for each of these immunophilin-ligand complexes in order to carry out these experiments.

The full disclosure of each of the patent documents and scientific papers cited herein is hereby incorporated by reference. Those documents serve to illustrate the state of the art in various aspects of this invention. Numerous modifications and variations of the present invention should be apparent to one of skill in the art. Such modifications and variations, including design choices in selecting a heterologous action domain, improved ligand, fusion protein design, DNA formulation, viral vector or other DNA delivery means, manner and route of transgene administration, etc. are intended to be encompassed by the scope of the invention and of the appended claims.

The invention claimed is:

1. A recombinant nucleic acid encoding a composite protein, which composite protein includes a CAB domain comprising a portion of calcineurin A and a portion of calcineurin B, wherein the CAB domain forms a tripartite complex with an FKBP/CAB ligand and an FKBP domain.

2. The recombinant nucleic acid of claim 1 wherein the calcineurin A portion of the CAB domain comprises a peptide sequence selected from any of the following peptide sequences: residues 12–394 of human calcineurin A, residues 12–370 of human calcineurin A and residues 340–394 of human calcineurin A disclosed in SEQ ID NO: 33.

3. The recombinant nucleic acid of claim 1 wherein the calcineurin B portion of the CAB domain comprises residues 3–170 of human calcineurin B disclosed in SEQ ID NO: 35.

4. The recombinant nucleic acid of claim 1, 2, or 3 wherein said CAB domain comprises a calcineurin A and/or calcineurin B peptide sequence which differs from a calcineurin peptide sequence by up to ten amino acid substitutions, deletions or insertions, wherein the calcineurin peptide sequence is selected from any of the following peptide sequences: residues 12–394 of SEQ ID NO: 33, residues 12–370 of SEQ ID NO: 33, residues 340–394 of SEQ ID NO: 33, or residues 3–170 of SEQ ID NO: 35.

5. A recombinant nucleic acid encoding a fusion protein comprising at least one CAB domain of claim 1 and at least one additional domain that is heterologous thereto.

6. The recombinant nucleic acid of claim 5 wherein the heterologous domain is selected from the group comprising a DNA binding domain, a transcription regulatory domain, a cytoplasmic signal initiation domain, a nuclear localization sequence, and a signaling domain.

7. The recombinant nucleic acid of claim 6 wherein the heterologous domain is lexA DNA binding domain, or a GAL4 DNA binding domain.

8. The recombinant nucleic acid of claim 6 wherein the heterologous domain is p65, VP16 or AP domain.

9. The recombinant nucleic acid of claim 6 wherein the heterologous domain is a KRAB domain or a ssn-6/TUP-1 domain.

10. The recombinant nucleic acid of claim 6 wherein the heterologous domain is an intracellular domain of a mammalian cell surface receptor.

11. A recombinant nucleic acid encoding a fusion protein containing one or more CAB domains which form a tripartite complex with an FKBP domain-containing protein and a FKBP/CAB ligand preferentially over FK506.

12. A vector comprising a recombinant nucleic acid of any of claim 1–3 or 5–11.

13. A vector comprising a recombinant nucleic acid of claim 4.

14. The vector of claim 12 wherein the vector is a viral vector.

15. The vector of claim 14 wherein the viral vector is selected from the group consisting of adenovirus, AAV, herpesvirus, retrovirus, hybrid adenovirus/AAV, poxvirus, and lentivirus.

16. An isolated host cell comprising and expressing a recombinant nucleic acid of any of claim 1–3 or 5–11.

17. A host cell of claim 16 which is an isolated cell of human origin.

18. A host cell of claim 16 which is encapsulated ex vivo within a biocompatible material.

19. An in vitro method for producing genetically engineered host cells comprising introducing into the cells a recombinant nucleic acid of any of claims 1–3 or 5–11 under conditions permitting DNA uptake by cells.

* * * * *

SEQUENCE LISTING

<160> NUMBER OF SEQ ID NOS: 35

<210> SEQ ID NO 1
<211> LENGTH: 14
<212> TYPE: PRT
<213> ORGANISM: HUMAN

<400> SEQUENCE: 1

Met Gly Ser Ser Lys Ser Lys Pro Lys Asp Pro Ser Gln Arg
1               5                   10

```
<210> SEQ ID NO 2
<211> LENGTH: 4
<212> TYPE: PRT
<213> ORGANISM: HUMAN

<400> SEQUENCE: 2

Lys Asp Glu Leu
1

<210> SEQ ID NO 3
<211> LENGTH: 4
<212> TYPE: PRT
<213> ORGANISM: HUMAN

<400> SEQUENCE: 3

His Asp Glu Leu
1

<210> SEQ ID NO 4
<211> LENGTH: 42
<212> TYPE: DNA
<213> ORGANISM: HUMAN

<400> SEQUENCE: 4
cgggcccccc ctcgagtcta cgaccgacag ggtggtgaaa gc            42

<210> SEQ ID NO 5
<211> LENGTH: 41
<212> TYPE: DNA
<213> ORGANISM: HUMAN

<400> SEQUENCE: 5
atataaatcg ctcgagccat actggcttcc aaatttcatg g             41

<210> SEQ ID NO 6
<211> LENGTH: 44
<212> TYPE: DNA
<213> ORGANISM: HUMAN

<400> SEQUENCE: 6
atataaatcg ctcgagttta cttggtccct tccatttgtt gggg          44

<210> SEQ ID NO 7
<211> LENGTH: 58
<212> TYPE: DNA
<213> ORGANISM: HUMAN

<400> SEQUENCE: 7
ccagtagggt ctagatctgg gcccacgata taagtcgacg ttgaggacat ttaccagc    58

<210> SEQ ID NO 8
<211> LENGTH: 63
<212> TYPE: DNA
<213> ORGANISM: HUMAN

<400> SEQUENCE: 8
ttaatctaga tcttcacttg tcatcgtcat ctttatagtc gacctctttc cgggctgcag  60
ctg                                                               63

<210> SEQ ID NO 9
<211> LENGTH: 41
<212> TYPE: DNA
<213> ORGANISM: HUMAN
```

-continued

```
<400> SEQUENCE: 9
atataaatcg ctcgagggaa atgaggcaag ttatcctttg g                    41

<210> SEQ ID NO 10
<211> LENGTH: 38
<212> TYPE: DNA
<213> ORGANISM: HUMAN

<400> SEQUENCE: 10
atataaatcg ctcgagaatg aggcaagtta tcctttgg                        38

<210> SEQ ID NO 11
<211> LENGTH: 66
<212> TYPE: DNA
<213> ORGANISM: HUMAN

<400> SEQUENCE: 11
ttaatctaga tctgggccct cacttgtcat cgtcatcttt atagtcgacc acatctacca  60
ccatca                                                            66

<210> SEQ ID NO 12
<211> LENGTH: 116
<212> TYPE: DNA
<213> ORGANISM: HUMAN

<400> SEQUENCE: 12
cgatttatat gggccctcta gatctagaac cagaaccaga accagaacca gaaccagaac  60
cagaaccaga accagaacca ccagaaccag aaccaccgtt gaggacattt accagc     116

<210> SEQ ID NO 13
<211> LENGTH: 58
<212> TYPE: DNA
<213> ORGANISM: HUMAN

<400> SEQUENCE: 13
gaatcgcaaa tctagatctg ggcccgtcat ctttatagtc gacaccagaa ccagaacc   58

<210> SEQ ID NO 14
<211> LENGTH: 58
<212> TYPE: DNA
<213> ORGANISM: HUMAN

<400> SEQUENCE: 14
gaatcgcaaa tctagatctg ggcccgtcat ctttatagtc gacagaacca gaaccaga   58

<210> SEQ ID NO 15
<211> LENGTH: 72
<212> TYPE: DNA
<213> ORGANISM: HUMAN

<400> SEQUENCE: 15
ggtggttctg gttctggtgg ttctggttct ggttctggtt ctggttctgg ttctggttct  60
ggttctggtt ct                                                     72

<210> SEQ ID NO 16
<211> LENGTH: 24
<212> TYPE: PRT
<213> ORGANISM: HUMAN
```

-continued

```
<400> SEQUENCE: 16

Gly Gly Ser Gly Ser Gly Ser Gly Ser Gly Ser Gly Ser Gly Ser
1               5                   10                  15

Gly Ser Gly Ser Gly Ser Gly Ser
            20

<210> SEQ ID NO 17
<211> LENGTH: 21
<212> TYPE: DNA
<213> ORGANISM: HUMAN

<400> SEQUENCE: 17
gtcgacagaa ccagaaccag a                                              21

<210> SEQ ID NO 18
<211> LENGTH: 21
<212> TYPE: DNA
<213> ORGANISM: HUMAN

<400> SEQUENCE: 18
gtcgacacca gaaccagaac c                                              21

<210> SEQ ID NO 19
<211> LENGTH: 5
<212> TYPE: PRT
<213> ORGANISM: HUMAN

<400> SEQUENCE: 19

Gly Gly Ser Gly Ser
1               5

<210> SEQ ID NO 20
<211> LENGTH: 72
<212> TYPE: DNA
<213> ORGANISM: HUMAN

<400> SEQUENCE: 20
tcgacgaatt cgggccccttt aagtccggag gtcacccatg ggtcgacgtc gacgtcggtc    60
gtcgactcga ga                                                        72

<210> SEQ ID NO 21
<211> LENGTH: 66
<212> TYPE: DNA
<213> ORGANISM: HUMAN

<400> SEQUENCE: 21
aatttctcga gtctacgacc gacgtcgacc catgggtgac ctccggactt aagggggccccg   60 aattcg                                                               66

<210> SEQ ID NO 22
<211> LENGTH: 42
<212> TYPE: DNA
<213> ORGANISM: HUMAN

<400> SEQUENCE: 22
cgggcccccc gaattcctcg agatgggcgt gcaggtggag ac                       42

<210> SEQ ID NO 23
<211> LENGTH: 37
<212> TYPE: DNA
<213> ORGANISM: HUMAN
```

```
<400> SEQUENCE: 23
gggtctggat ccgtggactt ccagttttag aagctcg                              37

<210> SEQ ID NO 24
<211> LENGTH: 49
<212> TYPE: DNA
<213> ORGANISM: HUMAN

<400> SEQUENCE: 24
atataaatcg ggatccgtct cgagccatac tggcttccaa atttcatgg                 49

<210> SEQ ID NO 25
<211> LENGTH: 72
<212> TYPE: DNA
<213> ORGANISM: HUMAN

<400> SEQUENCE: 25
tctttaacca tggcggccgc gggccctcac ttgtcatcgt catctttata gtcgaccaca     60
tctaccacca tc                                                          72

<210> SEQ ID NO 26
<211> LENGTH: 38
<212> TYPE: DNA
<213> ORGANISM: HUMAN

<400> SEQUENCE: 26
cttggtccct tccatttgtt ggggaaaaag tgactgag                             38

<210> SEQ ID NO 27
<211> LENGTH: 31
<212> TYPE: DNA
<213> ORGANISM: HUMAN

<400> SEQUENCE: 27
gggaacaatc tgaaagatac acagttacag c                                    31

<210> SEQ ID NO 28
<211> LENGTH: 64
<212> TYPE: DNA
<213> ORGANISM: HUMAN
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 28
gctgtaactg tgtatctttc agattgttcc csnnsnncat cttsnntacc tggaagagtt     60
cccc                                                                   64

<210> SEQ ID NO 29
<211> LENGTH: 65
<212> TYPE: DNA
<213> ORGANISM: HUMAN
```

```
<400> SEQUENCE: 29
ttaatctaga tctgggccct cacttgtcat cgtcatcttt atagtcgacc acatctacca      60
ccatc                                                                 65

<210> SEQ ID NO 30
<211> LENGTH: 41
<212> TYPE: DNA
<213> ORGANISM: HUMAN

<400> SEQUENCE: 30
atataaatcg ctcgagccat actggcttcc aaatttcatg g                         41

<210> SEQ ID NO 31
<211> LENGTH: 52
<212> TYPE: DNA
<213> ORGANISM: HUMAN
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 31
ctcagtcact ttttccccaa caaatggaag snnsnnagta aaaacatcca tg             52

<210> SEQ ID NO 32
<211> LENGTH: 2450
<212> TYPE: DNA
<213> ORGANISM: HUMAN

<400> SEQUENCE: 32
agagggtccg ccatgttccc cggcggcgcc gccgcttggc tctggtagcc gccgcccccg     60
cccccaaccc cgcccggccc agagcctagc cgagccccgg gcccagcatg gccgccccgg    120
agccggcccg ggctgcaccg ccccccaccc cgcccccgcc gcccccctcc ggggctgacc    180
gcgtcgtcaa agctgtccct ttccccccaa cacatcgctt gacatctgaa gaagtatttg    240
atttggatgg gatacccagg gttgatgttc tgaagaacca cttggtgaaa gaaggtcgag    300
tagatgaaga aattgcgctt agaattatca atgagggtgc tgccatcctt cggagagaga    360
aaaccatgat agaagtagaa gctccaatca cagtgtgtgg tgacatccat ggccaatttt    420
ttgatctgat gaacttttt gaagtaggag atcacctgc taatacacga tacctttttc     480
ttggcgatta tgtggacaga ggttattttta gtatagagca tgttctaggc actgaagaca    540
tatcgattaa tcctcacaat aatattaatg agtgtgtctt atatttatgg gttctgaaga    600
ttctataccc aagcacatta tttcttctga gaggcaacca tgaatgcaga caccttactg    660
aatattttac cttttaagcag gaatgtaaaa ttaagtattc ggaaagagtc tatgaagctt    720
gtatggaagc ttttgatagt ttgcctcttg ctgcactttt aaaccaacag tttctttgtg    780
ttcatggtgg actttcacca gaaatacaca cactggatga tattaggaga ttagatagat    840
tcaaagagcc acctgcattt ggaccaatgt gtgacttgtt atggtccgat ccttctgaag    900
attttgaaaa tgaaaaatca caggaacatt ttagtcacaa tacagttcga ggatgttctt    960 attttttataa ctatccagca gtgtgtgaat ttttgcaaaa caataatttg ttatcgatta   1020
ttagagctca tgaagctcaa gatgcaggct atagaatgta cagaaaaagt caaactacag   1080
ggttcccttc attaataaca attttttcgg cacctaatta cttagatgtc tacaataata   1140
```

-continued

```
aagctgctgt attaaagtat gaaaataatg tgatgaatat tcgacagttt aactgttctc    1200
cacatcctta ctggttgcct aatttttatgg atgtcttcac gtggtcttta ccgtttgttg    1260
gagaaaaagt gacagaaatg ttggtaaatg ttctgagtat ttgctctgat gatgaactaa    1320
tgactgaagg tgaagaccag tttgatggtt cagctgcagc ccggaaagaa atcataagaa    1380
acaaaattcg agcaattggc aagatggcaa gagtcttctc tgttctcagg gaggagagtg    1440
aaagtgtgct gacactcaag ggcctgactc ccacagggat gttgcctagt ggagtgttag    1500
ctggaggacg gcagaccctg caaagtggta atgatgttat gcaacttgct gtgcctcaga    1560
tggactgggg cacacctcac tcttttgcta acaattcaca taatgcatgc agggaattcc    1620
ttctgttttt tagttcctgt ctcagcagct gacctagaca gggtagtgta ttagctagtg    1680
tctcattaat acgtgatcag ggcagaaaac tgatagaatg ggtattcctt tcaattgaaa    1740
ataatggtca gttcctcagc ttttcatgaa atgatatggg agcagctcat atcataatgt    1800
ctgaaatatt tatttattca tctgtctaat tcacccttt cttttaaaag ccccagtttc    1860
agaatgtgaa tcagggatat tcctgttact aaaatggaaa tgtaattcca gtttctttt    1920 ttaattttt aaatttatgt cattgtattg gactatgctt atatttaaaa ctacttaatt    1980
tagagttaac tacctgctta ggccccagaa cattacttat gcccttcagt taccaaaaga    2040
tttgtgcaag gttttgtacc ctggtaaatg atgccaaagt ttgttttctg tggtgtttgt    2100
caaatgttct atgtataatt aactgtctgt aacatgctgt ttccttcctc tgcagatgta    2160
gctgctttcc taaatctgtc tgtctttctt taggttagct gtatgtctgt aaaagtatgt    2220
tcaattaaat tactccatca gacacttgtc tgtcttgcaa tgtagaagca gctttgtagc    2280
accttgtttt gaggtttgct gcatttgttg ctgcactttg tgcattctga acatgaatgt    2340
aacattagat attaagtcat tgttataagg ggttgaattt aaatcctgta agtcaaaatt    2400
gaaagggtgt tattaagtgt gcctttattt tgcatgaaaa taaaaagaat                2450
```

<210> SEQ ID NO 33
<211> LENGTH: 515
<212> TYPE: PRT
<213> ORGANISM: HUMAN

<400> SEQUENCE: 33

```
Met Ala Ala Pro Glu Pro Ala Arg Ala Ala Pro Pro Pro Pro Pro Pro
1               5                   10                  15

Pro Pro Pro Pro Gly Ala Asp Arg Val Val Lys Ala Val Pro Phe
            20                  25                  30

Pro Pro Thr His Arg Leu Thr Ser Glu Glu Val Phe Asp Leu Asp Gly
        35                  40                  45

Ile Pro Arg Val Asp Val Leu Lys Asn His Leu Val Lys Glu Gly Arg
    50                  55                  60

Val Asp Glu Glu Ile Ala Leu Arg Ile Ile Asn Glu Gly Ala Ala Ile
65                  70                  75                  80

Leu Arg Arg Glu Lys Thr Met Ile Glu Val Glu Ala Pro Ile Thr Val
                85                  90                  95

Cys Gly Asp Ile His Gly Gln Phe Phe Asp Leu Met Lys Leu Phe Glu
            100                 105                 110

Val Gly Gly Ser Pro Ala Asn Thr Arg Tyr Leu Phe Leu Gly Asp Tyr
        115                 120                 125

Val Asp Arg Gly Tyr Phe Ser Ile Glu His Val Leu Gly Thr Glu Asp
    130                 135                 140
```

```
Ile Ser Ile Asn Pro His Asn Ile Asn Glu Cys Val Leu Tyr Leu
145                 150                 155                 160

Trp Val Leu Lys Ile Leu Tyr Pro Ser Thr Leu Phe Leu Leu Arg
            165                 170                 175

Gly Asn His Glu Cys Arg His Leu Thr Glu Tyr Phe Thr Phe Lys Gln
        180                 185                 190

Glu Cys Lys Ile Lys Tyr Ser Glu Arg Val Tyr Glu Ala Cys Met Glu
    195                 200                 205

Ala Phe Asp Ser Leu Pro Leu Ala Ala Leu Leu Asn Gln Gln Phe Leu
    210                 215                 220

Cys Val His Gly Gly Leu Ser Pro Glu Ile His Thr Leu Asp Asp Ile
225                 230                 235                 240

Arg Arg Leu Asp Arg Phe Lys Glu Pro Pro Ala Phe Gly Pro Met Cys
                245                 250                 255

Asp Leu Leu Trp Ser Asp Pro Ser Glu Asp Phe Gly Asn Glu Lys Ser
                260                 265                 270

Gln Glu His Phe Ser His Asn Thr Val Arg Gly Cys Ser Tyr Phe Tyr
            275                 280                 285

Asn Tyr Pro Ala Val Cys Glu Phe Leu Gln Asn Asn Asn Leu Leu Ser
290                 295                 300

Ile Ile Arg Ala His Glu Ala Gln Asp Ala Gly Tyr Arg Met Tyr Arg
305                 310                 315                 320

Lys Ser Gln Thr Thr Gly Phe Pro Ser Leu Ile Thr Ile Phe Ser Ala
                325                 330                 335

Pro Asn Tyr Leu Asp Val Tyr Asn Asn Lys Ala Ala Val Leu Lys Tyr
            340                 345                 350

Glu Asn Asn Val Met Asn Ile Arg Gln Phe Asn Cys Ser Pro His Pro
        355                 360                 365

Tyr Trp Leu Pro Asn Phe Met Asp Val Phe Thr Trp Ser Leu Pro Phe
    370                 375                 380

Val Gly Glu Lys Val Thr Glu Met Leu Val Asn Val Leu Ser Ile Cys
385                 390                 395                 400

Ser Asp Asp Glu Leu Met Thr Glu Gly Glu Asp Gln Phe Asp Gly Ser
                405                 410                 415

Ala Ala Ala Arg Lys Glu Ile Ile Arg Asn Lys Ile Arg Ala Ile Gly
                420                 425                 430

Lys Met Ala Arg Val Phe Ser Val Leu Arg Glu Glu Ser Glu Ser Val
            435                 440                 445

Leu Thr Leu Lys Gly Leu Thr Pro Thr Gly Met Leu Pro Ser Gly Val
450                 455                 460

Leu Ala Gly Gly Arg Gln Thr Leu Gln Ser Gly Asn Asp Val Met Gln
465                 470                 475                 480

Leu Ala Val Pro Gln Met Asp Trp Gly Thr Pro His Ser Phe Ala Asn
                485                 490                 495

Asn Ser His Asn Ala Cys Arg Glu Phe Leu Leu Phe Ser Ser Cys
            500                 505                 510

Leu Ser Ser
        515

<210> SEQ ID NO 34
<211> LENGTH: 2548
<212> TYPE: DNA
<213> ORGANISM: SEQUENCE LISTING
```

-continued

```
<400> SEQUENCE: 34 aggctgggggg acaaccagag gccagggaga aagaggagac agaggaagca ccgagggtga       60
ctacgttgtc ttccctagat caattttctt ctggatggct cgtgctgagt ggtagatgag      120
cgaatcgatg agtccagcca ctgtgaacat gcccccaatg atggcgcaca cacctgtcag      180
gaagtgggtg aaggacctgt gcttctccgt cagcttcacc atcatgggcg agagctcata      240
gaggacgaag actccgggaa ggccttggtc gcccaacagc ccattggcaa ccttctcatg      300
tctggtcaca gagaactgat ttgtcctcag tacctctccg tccaccttca tgtacacagt      360
gggcaccacc ttcacaaagt gctgtaacac ctgtgaaggc agcggctccg gcgcgagcgc      420
gaggctgcag cccccgagtt tcccggccgt cttcgccccc tctccccctc ctttcttctt      480
ctctgcctct cctgcctctc gccgctgctc ctcccgcgct ctccggctct gaatgtcgac      540
cttaatttat ttcccctac cctgcccgct ccctcgcgtg cccaatcgcc cggccggcgc      600
gggccccgcg cgccgcctcc ccctcccac gcgcgccccc tccccgccgg cgacccgagg      660
gccgcagctg ggccgccgcc gccgtttcct gcgagccagc ctgagcgcaa cacttctccg      720
agccagcgag ccagcgagcc gccgacccgc cgagcaaaat gggaaatgag gcaagttatc      780
ctttggaaat gtgctcacac tttgatgcgg atgaaattaa aaggctagga aagagattta      840
agaagcttga tttggacaat tctggttctt tgagtgtgga agagttcatg tctctgcctg      900
agttacaaca gaatccttta gtacagcgag taatagatat attcgacaca gatgggaatg      960
gagaagtaga ctttaaagaa ttcattgagg gcgtctctca gttcagtgtc aaaggagata     1020
aggagcagaa attgaggttt gctttccgta tctatgacat ggataaagat ggctatattt     1080
ccaatgggga actcttccag gtattgaaga tgatggtggg gaacaatctg aaagatacac     1140
agttacagca aattgtagac aaaaccataa taaatgcaga taaggatgga gatggaagaa     1200
tatcctttga agaattctgt gctgttgtag gtggcctaga tatccacaaa agatggtgg     1260 tagatgtgtg actcttatca gagagtacca cccaacactt ttgctttctt ctccatctct     1320
gaagatctgc tcaagacgtc cagcaatgct ctctgtgtat ttaaatggaa gtatttttct     1380
ctgtgaagcc acattttcca acatgagcct catgaagcca actaagtgtt attgaactgt     1440
aattctctca ataactcagt gtagcacttt aaagtctgaa ggacagcaac atgaaaagag     1500
catatcaatg tggtggagaa agggaagggg ttggcttttt aatttatttt tcttcatctt     1560
ttataacaag aaagtatcta tatatacata tgtaaatatt tatatataga tatatgtagc     1620
tttctatata tgtagtaggt tggctttaat ttaatatcct tgattcagaa acaaaacaat     1680 agtacaaaa agtgccaagc agaacataaa acatccttac ttttatttca cacagtttta     1740
tatatagata aagactgta caatttgagc cgggtgttaa gccagctatt ttccttttcc     1800
tgtgctttct cctttgagag attgacaaag catttgttaa cgtcctatta tttaccttaa     1860
ttacattttt gtaacaaagg agtctgtaac tttatttata cttatgaata tatccaggga     1920
ctacttctca ttgctgagca gcttttaata cacctctgct tgaggagaaa gtctagttca     1980
ttgctactgc caagagctag ttcttgtgtt catatagtaa ctgcacaggg cttatagctg     2040
cttcattctg ctactttgta actaggagcc attgcattta ttaaatgtcc ctcagtaacg     2100
ttaagtgcta gttgtgattt tatacataaa ggccagaagc tgtctgaggc aatcatgatt     2160
gattgtatgt atcacttact gaagaatacc tgaagtgatc atgtaactac ttataaggga     2220
tatccatttg tttgattaca tgggtaaata atttgtcatt aaacttgtgt ttgaatcatg     2280
aattcccttg tttcaaaaga cttgcagcta atctaaaaaa ctggtgatat ttaatatgca     2340
```

-continued

```
tgtatgtatc taaacaccca catatatttg tggtttaagt gtgagaaatc ttgctaatct    2400
atatgccaca gaagagcaaa attgtatcca aatttatgcc acttaaattt ctttaccacg    2460
agggatagag catgcatact ggtttttttt tcttgatttg cccatataat tggtaatgga    2520
taacttaata aatttgtgtg atataaaa                                       2548
```

<210> SEQ ID NO 35
<211> LENGTH: 170
<212> TYPE: PRT
<213> ORGANISM: HUMAN

<400> SEQUENCE: 35

```
Met Gly Asn Glu Ala Ser Tyr Pro Leu Glu Met Cys Ser His Phe Asp
1               5                   10                  15

Ala Asp Glu Ile Lys Arg Leu Gly Lys Arg Phe Lys Lys Leu Asp Leu
            20                  25                  30

Asp Asn Ser Gly Ser Leu Ser Val Glu Glu Phe Met Ser Leu Pro Glu
        35                  40                  45

Leu Gln Gln Asn Pro Leu Val Gln Arg Val Ile Asp Ile Phe Asp Thr
    50                  55                  60

Asp Gly Asn Gly Glu Val Asp Phe Lys Glu Phe Ile Glu Gly Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Val Leu Lys Met Met Val Gly Asn Asn Leu Lys Asp Thr Gln
        115                 120                 125

Leu Gln Gln Ile Val Asp Lys Thr Ile Ile Asn Ala Asp Lys Asp Gly
    130                 135                 140

Asp Gly Arg Ile Ser Phe Glu Glu Phe Cys Ala Val Val Gly Gly Leu
145                 150                 155                 160

Asp Ile His Lys Lys Met Val Val Asp Val
                165                 170
```